(12) United States Patent
Ogawa

(10) Patent No.: US 10,921,577 B2
(45) Date of Patent: Feb. 16, 2021

(54) ENDOSCOPE DEVICE

(71) Applicant: OLYMPUS CORPORATION, Tokyo (JP)

(72) Inventor: Kiyotomi Ogawa, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 148 days.

(21) Appl. No.: 16/390,103

(22) Filed: Apr. 22, 2019

(65) Prior Publication Data

US 2019/0324261 A1 Oct. 24, 2019

(30) Foreign Application Priority Data

Apr. 23, 2018 (JP) .................................. 2018-082654

(51) Int. Cl.
| | |
|---|---|
| G02B 23/24 | (2006.01) |
| G06T 5/00 | (2006.01) |
| A61B 1/00 | (2006.01) |
| A61B 1/06 | (2006.01) |
| A61B 1/045 | (2006.01) |

(52) U.S. Cl.
CPC ...... *G02B 23/2415* (2013.01); *A61B 1/00009* (2013.01); *A61B 1/00045* (2013.01); *A61B 1/045* (2013.01); *A61B 1/0676* (2013.01); *G02B 23/2461* (2013.01); *G02B 23/2469* (2013.01); *G06T 5/002* (2013.01); *A61B 1/00193* (2013.01); *G06T 2207/10068* (2013.01)

(58) Field of Classification Search
None
See application file for complete search history.

(56) References Cited

U.S. PATENT DOCUMENTS

| | | | |
|---|---|---|---|
| 9,554,028 B2* | 1/2017 | Ichikawa | H04N 5/765 |
| 2004/0186351 A1* | 9/2004 | Imaizumi | A61B 5/0071 |
| | | | 600/160 |
| 2010/0245551 A1* | 9/2010 | Morita | A61B 5/0084 |
| | | | 348/68 |
| 2018/0000330 A1* | 1/2018 | Takeuchi | A61B 1/00006 |
| 2018/0197306 A1* | 7/2018 | Fukunishi | H04N 13/211 |
| 2018/0227476 A1* | 8/2018 | Kobayashi | H04N 13/00 |
| 2018/0234646 A1* | 8/2018 | Kobayashi | H04N 5/37452 |
| 2018/0344136 A1* | 12/2018 | Kikuchi | A61B 1/00009 |
| 2018/0364178 A1* | 12/2018 | Fukunishi | G01N 21/954 |
| 2019/0239725 A1* | 8/2019 | Ogasawara | A61B 1/045 |
| 2019/0239732 A1* | 8/2019 | Ogawa | H04N 5/341 |
| 2019/0320877 A1* | 10/2019 | Sakai | A61B 1/00045 |

FOREIGN PATENT DOCUMENTS

JP 2013105078 A 5/2013

* cited by examiner

*Primary Examiner* — Mohammed Jebari
(74) *Attorney, Agent, or Firm* — Scully, Scott, Murphy & Presser, P.C.

(57) ABSTRACT

In an endoscope device, an imaging device sequentially reads pixel signals from at least some of a plurality of pixels row by row during a first period. A control unit causes a light source to generate illumination light during a second period. The second period is at least a part of a period other than the first period. The control unit causes the light source to stop the generation of the illumination light during a third period. The third period is all of a period other than the second period. The control unit causes a switching unit to start switching of an imaging condition during the third period and complete the switching of the imaging condition during the third period.

20 Claims, 24 Drawing Sheets

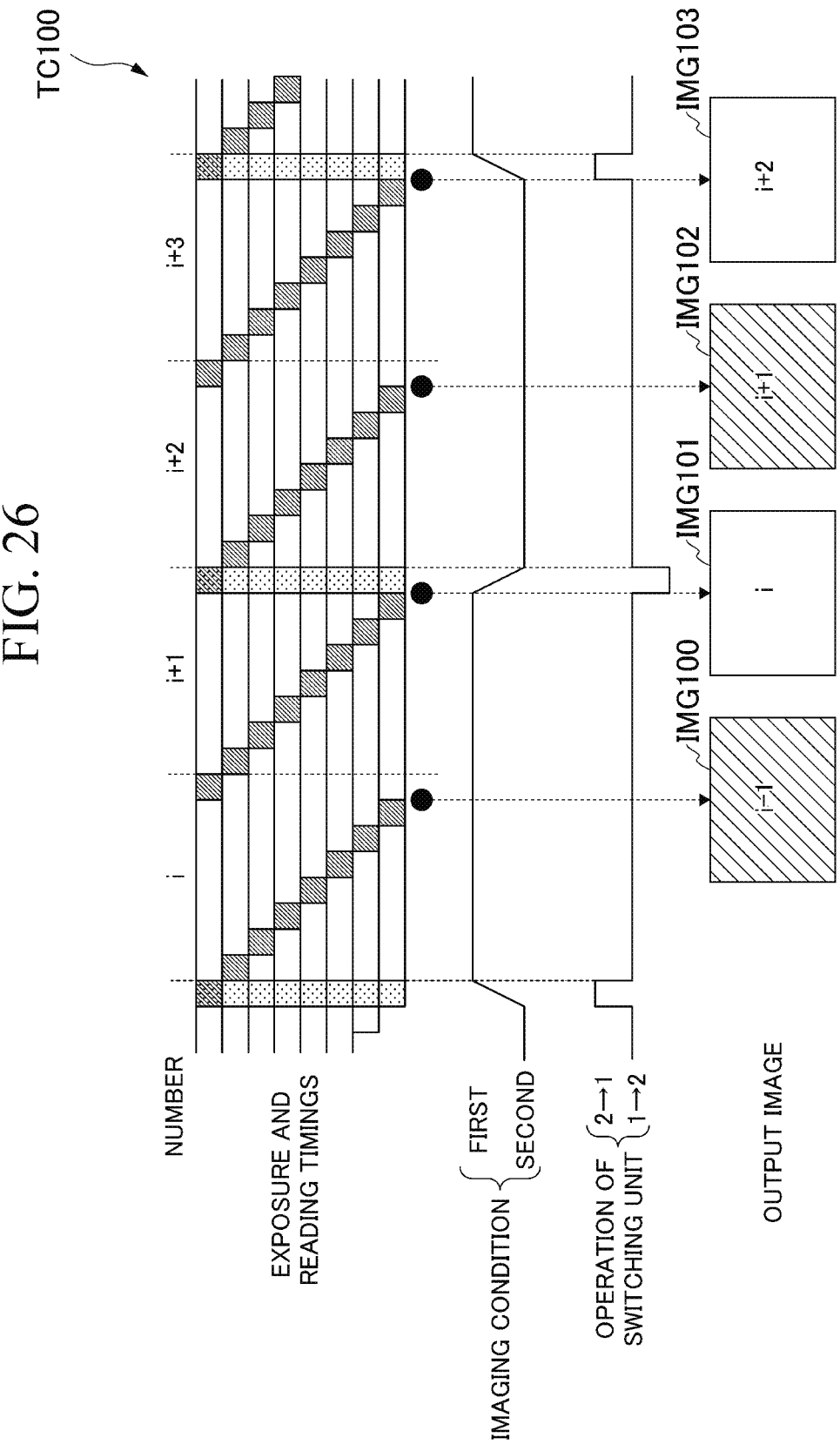

ENDOSCOPE DEVICE

BACKGROUND OF THE INVENTION

Field of the Invention

The present invention relates to an endoscope device.

Priority is claimed on Japanese Patent Application No. 2018-082654, filed Apr. 23, 2018, the content of which is incorporated herein by reference.

Description of Related Art

Industrial endoscopes are widely used for observing internal damage and corrosion in boilers, engines, turbines, chemical plants, and the like. When defects such as damage and corrosion are found, it is necessary to perform switching between countermeasure methods in accordance with a degree thereof. Thus, an industrial endoscope having a measurement function of measuring sizes of damage and corrosion has been developed.

An endoscope device disclosed in Japanese Unexamined Patent Application, First Publication No. 2013-105078 includes an optical system for causing two optical images of a subject to be formed in a common region of an imaging device. Light passing through two optical paths corresponding to two different viewpoints forms two optical images. Hereinafter, the two optical paths are referred to as a first optical path and a second optical path. The endoscope device includes an optical path switching means for performing switching between two optical paths. The endoscope device captures an optical image formed by only light passing through either one of the two optical paths.

The endoscope device performs switching between two imaging conditions and acquires two images. The light passing through the first optical path forms a first optical image. The first optical image is an optical image from a first viewpoint. The endoscope device generates a first image by capturing the first optical image. At this moment, the first imaging condition is implemented. Subsequently, optical paths are switched. The light passing through the second optical path forms a second optical image. The second optical image is an optical image from a second viewpoint. The endoscope device generates a second image by imaging the second optical image. At this moment, the second imaging condition is implemented. The endoscope device measures a shape of a subject using the principle of stereo measurement on the basis of parallaxes provided in the first image and the second image. The first image and the second image are images captured from viewpoints different from each other.

When the tip of the endoscope or the subject moves while the first image and the second image are acquired, a positional relationship between two viewpoints changes and a mismatch between a stereo measurement parameter (such as a baseline length) and positions of two viewpoints occurs. Therefore, the endoscope device cannot accurately measure the shape of the subject. The endoscope device disclosed in Japanese Unexamined Patent Application, First Publication No. 2013-105078 alternately acquires a first image and a second image. When the amount of position shift between two first images is less than a predetermined threshold value, the endoscope device determines that there is no movement of an endoscope tip (tip movement) or movement of a subject (tip movement) during a period in which two first images are acquired and performs a measurement process.

SUMMARY OF THE INVENTION

According to a first aspect of the present invention, an endoscope device includes a light source, an illumination optical system, an observation optical system, an imaging device, a switching unit, and a control unit. The light source generates illumination light. The illumination optical system radiates the illumination light to a subject. The observation optical system forms an optical image of the subject. The imaging device has a plurality of pixels disposed in a matrix and images the subject. The imaging device sequentially reads pixel signals from at least some of the plurality of pixels row by row during a first period. The imaging device generates an image of the subject during each frame period of a plurality of frame periods on the basis of the pixel signals read from at least some of the plurality of pixels. The pixel signals are generated on the basis of the optical image of the subject. The switching unit performs switching between a plurality of imaging conditions so that the imaging device images the subject. The control unit causes the light source to generate the illumination light during a second period. The second period is at least a part of a period other than the first period. The control unit causes the light source to stop the generation of the illumination light during a third period. The third period is all of a period other than the second period and includes the first period. The second period and the third period are alternately iterated. The control unit causes the switching unit to start switching of the imaging condition during the third period and complete the switching of the imaging condition during the third period.

According to a second aspect of the present invention, in the first aspect, the imaging device may read the pixel signals in a time period that is less than or equal to half a length of each frame period of the plurality of frame periods during the first period.

According to a third aspect of the present invention, in the first aspect, the endoscope device may further include an image processing unit configured to execute image processing on a plurality of images generated during the plurality of frame periods. The plurality of imaging conditions may include a first imaging condition and a second imaging condition. The first imaging condition and the second imaging condition may be different from each other. The imaging device may generate a first image of the subject by imaging the subject under the first imaging condition. The imaging device may generate a second image of the subject by imaging the subject under the second imaging condition. The image processing unit may process the first image and the second image.

According to a fourth aspect of the present invention, in the third aspect, the imaging device may generate a plurality of at least one of first images and second images. When the imaging device generates the plurality of first images, the image processing unit may calculate a value indicating whether or not the plurality of first images are suitable for image processing. When the imaging device generates the plurality of second images, the image processing unit may calculate a value indicating whether or not the plurality of second images are suitable for image processing.

According to a fifth aspect of the present invention, in the third aspect, the imaging device may generate a plurality of first images by imaging the subject under the first imaging condition. The imaging device may generate a plurality of second images by imaging the subject under the second imaging condition. The image processing unit may generate a third image by executing a noise reduction process on the plurality of first images. The image processing unit may generate a fourth image by executing the noise reduction process on the plurality of second images. The image processing unit may execute a process different from the noise reduction process on the third image and the fourth image.

According to a sixth aspect of the present invention, in the third aspect, the image processing unit may calculate three-dimensional (3D) coordinates of at least one point on a surface of the subject on the basis of the first image and the second image.

According to a seventh aspect of the present invention, in the fifth aspect, the image processing unit may calculate 3D coordinates of at least one point on a surface of the subject on the basis of the third image and the fourth image.

According to an eighth aspect of the present invention, in the sixth aspect, the endoscope device may further include a data generation unit. The illumination light may be white light. The imaging device may include a red color filter, a green color filter, and a blue color filter. The imaging device may generate a color image as the image of the subject. The color image may have information indicating each of brightness of red, brightness of green, and brightness of blue. The data generation unit may generate data in which 3D coordinates of a plurality of points on the surface of the subject are associated with the information corresponding to the plurality of points.

According to a ninth aspect of the present invention, in the sixth aspect, the observation optical system may include a first optical system and a second optical system. The first optical system and the second optical system may be disposed on an optical front side of the imaging device. The first optical system may form a first optical image of the subject corresponding to a first viewpoint on the imaging device. The second optical system may form a second optical image of the subject corresponding to a second viewpoint different from the first viewpoint on the imaging device. The switching unit may cause light that passes through the first optical system to be incident on the imaging device and block light that passes through the second optical system under the first imaging condition. The switching unit may cause light that passes through the second optical system to be incident on the imaging device and block light that passes through the first optical system under the second imaging condition. The control unit may switch the optical image to be formed on the imaging device between the first optical image and the second optical image by controlling the switching unit. The image processing unit may calculate the 3D coordinates using a passive stereo method on the basis of the first image corresponding to the first optical image and the second image corresponding to the second optical image.

According to a tenth aspect of the present invention, in the first aspect, the endoscope device may further include an image processing unit, a data generation unit, a first light source, and a second light source. The image processing unit may execute image processing on a plurality of images during each frame period of the plurality of frame periods. The first light source and the second light source may serve as the light source. The illumination light may include first illumination light and second illumination light. The first light source may generate white light serving as the first illumination light. The second light source may generate the second illumination light. The illumination optical system may include a pattern generation unit configured to give a spatial pattern including a bright part and a dark part to the second illumination light. The illumination optical system may radiate the second illumination light to which the pattern is given to the subject. The plurality of imaging conditions may include a first imaging condition and a second imaging condition. Under the first imaging condition, the first illumination light may be radiated to the subject and radiation of the second illumination light to the subject may be stopped. Under the second imaging condition, the second illumination light may be radiated to the subject and radiation of the first illumination light to the subject may be stopped. The imaging device may generate a first image of the subject by imaging the subject under the first imaging condition. The imaging device may generate a second image of the subject by imaging the subject under the second imaging condition. The image processing unit may calculate 3D coordinates of a plurality of points on a surface of the subject using an active stereo method on the basis of the second image. The imaging device may include a red color filter, a green color filter, and a blue color filter. The imaging device may generate a color image as the first image. The color image may have information indicating each of brightness of red, brightness of green, and brightness of blue. The data generation unit may generate data in which the 3D coordinates of the plurality of points are associated with the information corresponding to the plurality of points.

According to an eleventh aspect of the present invention, in the tenth aspect, the imaging device may generate a plurality of at least one of first images and second images. When the imaging device generates the plurality of first images, the image processing unit may calculate a value indicating whether or not the plurality of first images are suitable for image processing. When the imaging device generates the plurality of second images, the image processing unit may calculate a value indicating whether or not the plurality of second images are suitable for image processing.

According to a twelfth aspect of the present invention, in the tenth aspect, the imaging device may generate a plurality of second images by imaging the subject under the second imaging condition. The image processing unit may generate a third image by executing a noise reduction process on the plurality of second images. The image processing unit may calculate the 3D coordinates of the plurality of points on the basis of the third image.

According to a thirteenth aspect of the present invention, in the third aspect, the illumination optical system may include a pattern generation unit configured to give a spatial pattern including a bright part and a dark part to the illumination light. The plurality of imaging conditions may further include a third imaging condition. The imaging device may generate a third image of the subject by imaging the subject under the third imaging condition. The switching unit may perform switching between the first imaging condition, the second imaging condition, and the third imaging condition by causing a phase of the pattern of the illumination light to be shifted. A pattern phase under the first imaging condition, a pattern phase under the second imaging condition, and a pattern phase under the third imaging condition may be different from one another. The image processing unit may calculate 3D coordinates of a plurality of points on a surface of the subject using a phase shift method on the basis of at least the first image, the second image, and the third image.

According to a fourteenth aspect of the present invention, in the thirteenth aspect, the endoscope device may further include a data generation unit, a first light source, and a second light source. The first light source and the second light source serve as the light source. The illumination light may include first illumination light and second illumination light. The first light source may generate white light serving as the first illumination light. The second light source may generate the second illumination light. The pattern generation unit may give the pattern to the second illumination light. The plurality of imaging conditions may further include a fourth imaging condition. Under the first imaging condition, the second imaging condition, and the third imaging condition, the second illumination light may be radiated to the subject and radiation of the first illumination light to the subject may be stopped. Under the fourth imaging condition, the first illumination light may be radiated to the subject and radiation of the second illumination light to the subject may be stopped. The imaging device may generate a fourth image of the subject by imaging the subject under the fourth imaging condition. The imaging device may include a red color filter, a green color filter, and a blue color filter. The imaging device may generate a color image as the fourth image. The color image may have information indicating each of brightness of red, brightness of green, and brightness of blue. The data generation unit may generate data in which the 3D coordinates of the plurality of points on the surface of the subject are associated with the information corresponding to the plurality of points.

According to a fifteenth aspect of the present invention, in the fourteenth aspect, the imaging device may generate a plurality of at least one of first images, second images, third images, and fourth images. When the imaging device generates the plurality of first images, the image processing unit may calculate a value indicating whether or not the plurality of first images are suitable for image processing. When the imaging device generates the plurality of second images, the image processing unit may calculate a value indicating whether or not the plurality of second images are suitable for image processing When the imaging device generates the plurality of third images, the image processing unit may calculate a value indicating whether or not the plurality of third images are suitable for image processing. When the imaging device generates the plurality of fourth images, the image processing unit may calculate a value indicating whether or not the plurality of fourth images are suitable for image processing.

According to a sixteenth aspect of the present invention, in the thirteenth aspect, the control unit may cause the switching unit to set the first imaging condition during a plurality of first frame periods. The control unit may cause the switching unit to set the second imaging condition during a plurality of second frame periods. Each second frame period of the plurality of second frame periods may be different from each first frame period of the plurality of first frame periods. The control unit may cause the switching unit to set the third imaging condition during a plurality of third frame periods. Each third frame period of the plurality of third frame periods may be different from each first frame period of the plurality of first frame periods and may be different from each second frame period of the plurality of second frame periods. The image processing unit may generate a fifth image by executing a noise reduction process on a plurality of first images. The image processing unit may generate a sixth image by executing the noise reduction process on a plurality of second images. The image processing unit may generate a seventh image by executing the noise reduction process on a plurality of third images. The image processing unit may calculate the 3D coordinates of the plurality of points on the basis of the fifth image, the sixth image, and the seventh image.

According to a seventeenth aspect of the present invention, in the third aspect, a focus of the observation optical system under the first imaging condition may be different from a focus of the observation optical system under the second imaging condition. The image processing unit may generate a third image by synthesizing the first image and the second image.

According to an eighteenth aspect of the present invention, in the third aspect, the amount of light of the light source under the first imaging condition may be different from the amount of light of the light source under the second imaging condition. The image processing unit may generate a third image by synthesizing the first image and the second image.

According to a nineteenth aspect of the present invention, in the third aspect, the observation optical system may include a first optical system, a second optical system, and the switching unit. The first optical system may be disposed on an optical front side of the imaging device and may form a first optical image of the subject on the imaging device. The second optical system may be disposed on an optical front side of the imaging device and may form a second optical image of the subject on the imaging device. The switching unit may select either one of the first optical system and the second optical system and cause only either one of the first optical image and the second optical image to be formed on the imaging device. A visual field of the first optical system and a visual field of the second optical system may have a common region. The switching control unit may switch the optical image formed on the imaging device by controlling the switching unit. The first optical image may be formed on the imaging device under the first imaging condition. The second optical image may be formed on the imaging device under the second imaging condition. The image processing unit may align a region of the first image corresponding to the common region and a region of the second image corresponding to the common region and generate a third image by synthesizing the first image and the second image.

According to a twentieth aspect of the present invention, in the third aspect, a focus of the observation optical system under the first imaging condition may be different from a focus of the observation optical system under the second imaging condition. The control unit may cause the switching unit to set the first imaging condition during a plurality of first frame periods. The control unit may cause the switching unit to set the second imaging condition during a plurality of second frame periods. Each second frame period of the plurality of second frame periods may be different from each first frame period of the plurality of first frame periods. The image processing unit may generate a fourth image by executing a noise reduction process on a plurality of first images. The image processing unit may generate a fifth image by executing the noise reduction process on a plurality of second images. The image processing unit may generate the third image by synthesizing the fourth image and the fifth image.

BRIEF DESCRIPTION OF THE DRAWINGS

FIG. 26 is a timing chart showing an operation of an imaging device according to a reference form of the present invention.

DETAILED DESCRIPTION OF THE INVENTION

Hereinafter, embodiments of the present invention will be described with reference to the drawings.

First Embodiment

Figure 1:
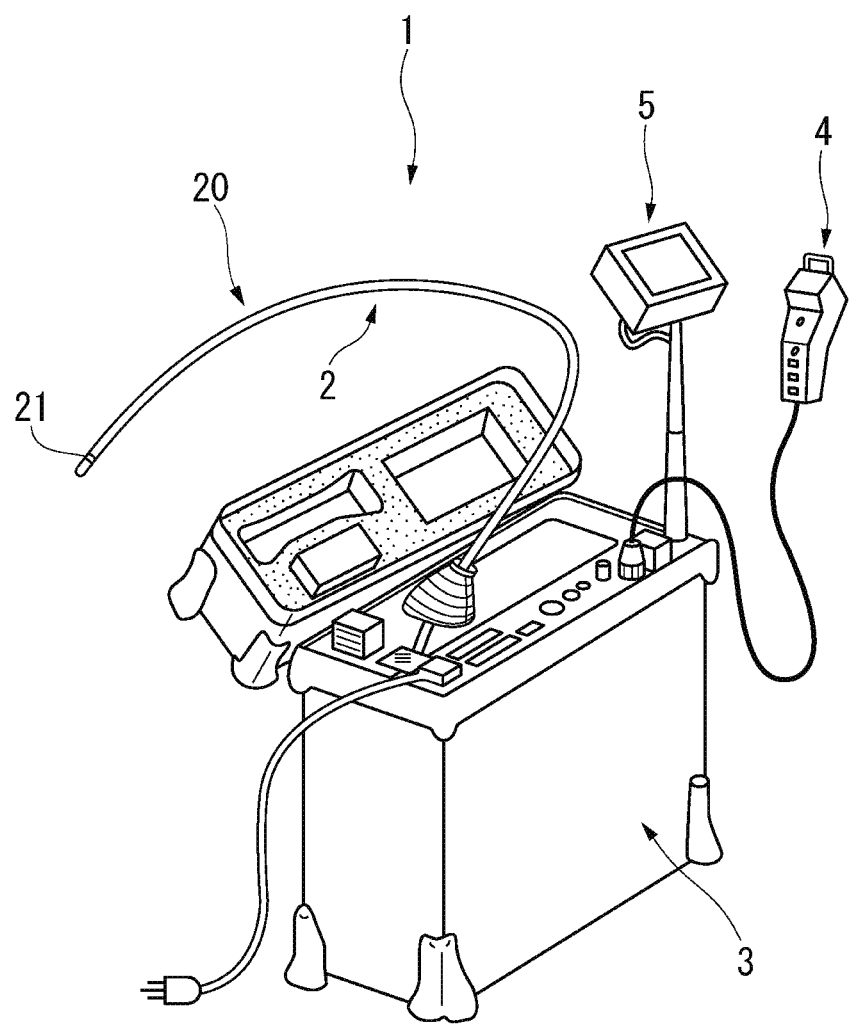
FIG. 1 is a perspective view showing an overall configuration of an endoscope device according to a first embodiment of the present invention.
Figure 2:
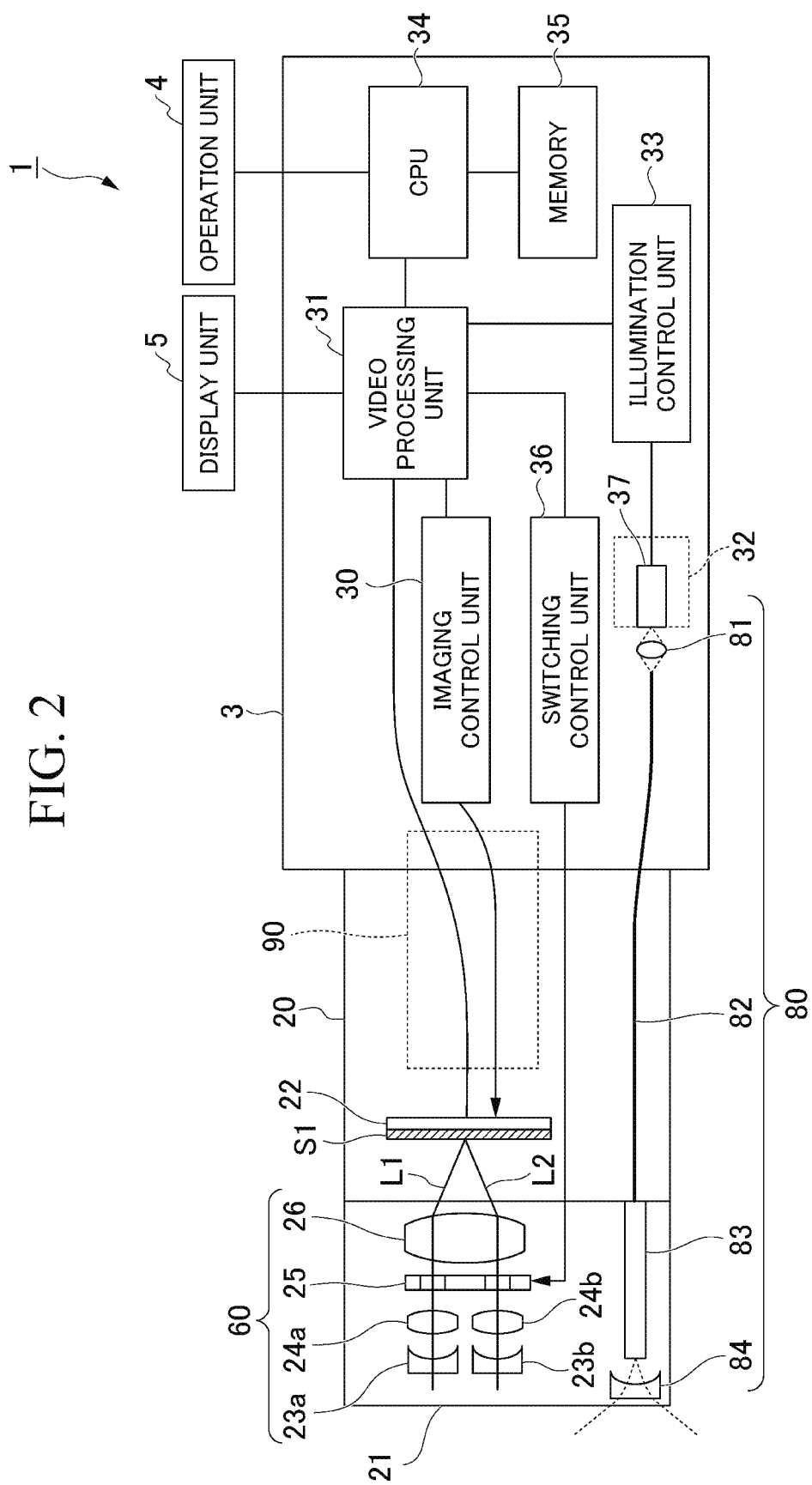
FIG. 2 is a block diagram showing a detailed configuration of the endoscope device according to the first embodiment of the present invention.

FIG. 1 shows an overall configuration of an endoscope device 1 according to a first embodiment of the present invention. FIG. 2 shows an internal configuration of the endoscope device 1. The endoscope device 1 shown in FIG. 1 has an endoscope 2, a main body unit 3, an operation unit 4, and a display unit 5. The endoscope 2 has an elongated insertion unit 20.

The insertion unit 20 is inserted into a physical object to be observed. An optical adapter 21 can be attached to a tip of the insertion unit 20. The optical adapter 21 has an optical system for taking light from a subject into the tip of the insertion unit 20. For example, the endoscope device 1 can acquire two optical images corresponding to a plurality of different viewpoints by attaching the stereo optical adapter to the tip of the insertion unit 20. Using the two optical images, the endoscope device 1 can measure dimensions of the subject by the principle of triangulation. The main body unit 3 has a configuration for controlling the endoscope device 1. The operation unit 4 receives an operation performed by a user. The display unit 5 (a display) displays images acquired by the endoscope device 1, processing menus, and the like.

FIG. 2 shows a detailed configuration of the endoscope device 1. The optical adapter 21 is attached to the tip of the insertion unit 20 shown in FIG. 2. The optical adapter 21 of the first embodiment is a stereo optical adapter for forming a plurality of optical images corresponding to a plurality of viewpoints. The optical adapter 21 has an observation optical system 60. The optical adapter 21 has a part of an illumination optical system 80. The observation optical system 60 has a concave lens 23a, a concave lens 23b, a convex lens 24a, a convex lens 24b, a switching unit 25, and an image forming optical system 26. The illumination optical system 80 includes a condenser lens 81, a light guide 82, a rod lens 83, and a diffusion lens 84. The condenser lens 81 is disposed in the main body unit 3. The light guide 82 is disposed in the main body unit 3 and the insertion unit 20. The rod lens 83 and the diffusion lens 84 are disposed in the optical adapter 21.

The insertion unit 20 has an imaging device 22 (an image sensor). The imaging device 22 is disposed on the tip of the insertion unit 20. The main body unit 3 includes an imaging control unit 30, a video processing unit 31, a light source unit 32, an illumination control unit 33, a CPU 34, a memory 35, and a switching control unit 36.

The light source unit 32 includes a white light source 37.

Figure 4:
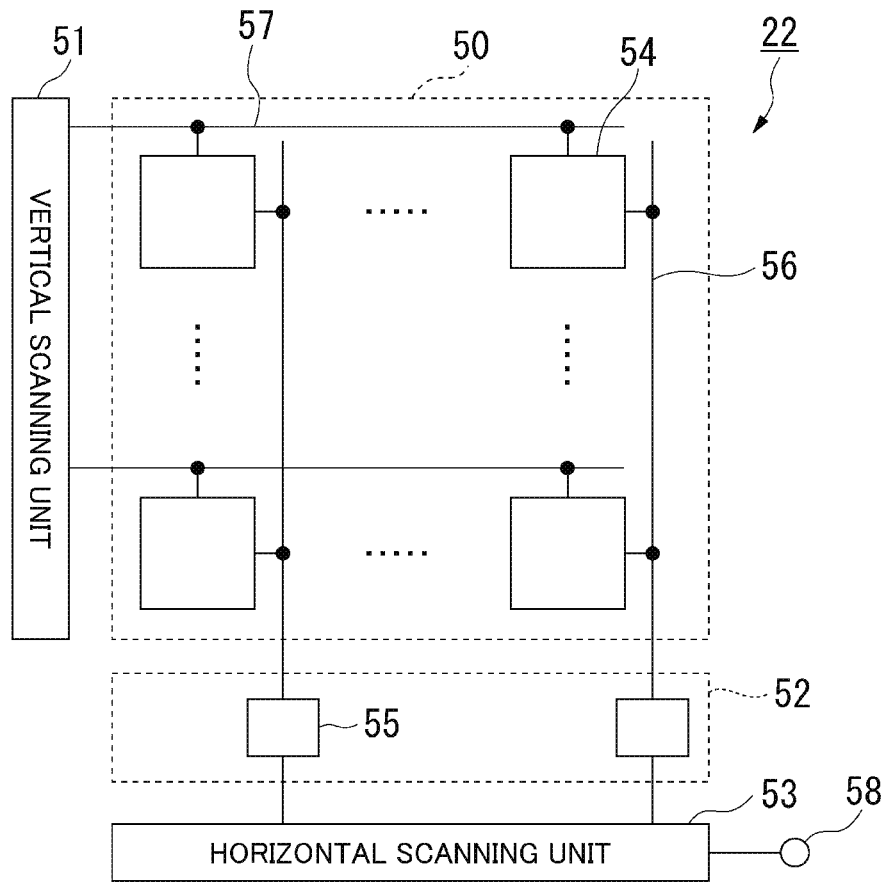
FIG. 4 is a block diagram showing a configuration of an imaging device according to the first embodiment of the present invention.

The outline of the configuration shown in FIG. 2 will be described. The white light source 37 generates illumination light. The illumination optical system 80 radiates the illumination light to the subject. The observation optical system 60 forms an optical image of the subject. The imaging device 22 has a plurality of cells 54 disposed in a matrix and images the subject. A configuration of the cell 54 which is a pixel of the imaging device 22 is shown in FIG. 4. The configuration of the cell 54 will be described below. The switching unit 25 (a switching device) performs switching between a plurality of imaging conditions so that the imaging device 22 images the subject. The imaging control unit 30, the illumination control unit 33, and the switching control unit 36 are control units (controllers).

During a first period, the imaging device 22 sequentially reads pixel signals from at least some of the plurality of cells 54 row by row. The pixel signals are generated on the basis of the optical image of the subject. The imaging device 22 generates an image of the subject during each frame period of a plurality of frame periods on the basis of at least some of pixel signals (pixel signals of valid pixels) read from at least some of the plurality of cells 54. The illumination control unit 33 causes the white light source 37 to generate the illumination light during a second period. The second period is at least a part of a period other than the first period. The illumination control unit 33 causes the white light source 37 to stop the generation of the illumination light during a third period. The third period is all of a period other than the second period and includes the first period. The second period and the third period are alternately iterated. The switching control unit 36 causes the switching unit 25 to start switching of the imaging condition during the third period and causes the switching of the imaging condition to be completed during the third period.

A frame is a set of a plurality of pixel signals included in one image. One image (one frame) is generated during one frame period. The imaging device 22 generates one image on the basis of pixel signals of one frame.

Details of the configuration shown in FIG. 2 will be described. The white light source 37 converts power supplied from the illumination control unit 33 into white light. Thereby, the white light source 37 generates illumination light for illuminating the subject. For example, the white light source is a combination of a semiconductor light-emitting element and a phosphor. The semiconductor light-emitting element is a light-emitting diode (LED), a laser diode (LD) or the like, and emits blue light. The phosphor converts the blue light, which is excitation light, into white light. The semiconductor light-emitting element can perform switching between ON and OFF of light at high speed. The illumination control unit 33 can adjust an exposure time period in the imaging of the subject by adjusting a turning-on period of the semiconductor light-emitting element. Light emission efficiency of the semiconductor light-emitting element is higher than that of another light source such as a halogen lamp. Therefore, power consumption is less than that of other light sources of the same brightness and the endoscope device 1 can be miniaturized.

The illumination control unit 33 supplies electric power to the light source unit 32. The illumination control unit 33 controls a timing at which the white light source 37 is turned on, a timing at which the white light source 37 is turned off, and the amount of light emitted from the white light source 37 on the basis of light source control parameters output from the video processing unit 31. A control mode of the white light source 37 includes a continuous turning-on mode and a pulse turning-on mode. In the continuous turning-on mode, the amount of light is controlled by a magnitude of an electric direct current supplied to the light source unit 32. In the pulse turning-on mode, the amount of light is controlled by a width and a height of an electric current pulse supplied to the light source unit 32. The white light source 37 may be disposed in the optical adapter 21.

The white light emitted from the white light source 37 is concentrated by the condenser lens 81. The white light concentrated by the condenser lens 81 is transmitted to the tip of the insertion unit 20 via the disposed light guide 82. The light guide 82 is an optical fiber bundle formed by bundling the strands of the optical fiber. The white light emitted from the light guide 82 is transmitted through the optical adapter 21 by the rod lens 83. The white light emitted from the rod lens 83 is radiated to the subject by the diffusion lens 84.

The observation optical system 60 takes in light reflected on a surface of the subject illuminated with the white light. The light taken in by the observation optical system 60 is incident on the imaging device 22. The observation optical system 60 forms an optical image of the subject illuminated with the illumination light on the imaging device 22.

The observation optical system 60 includes a first optical system and a second optical system. The first optical system and the second optical system are disposed on an optical front side (a subject side) of the imaging device 22. The first optical system forms a first optical image of the subject corresponding to a first viewpoint on the imaging device 22. The second optical system forms a second optical image of the subject corresponding to a second viewpoint different from the first viewpoint on the imaging device 22.

The concave lens 23a, the convex lens 24a, and the image forming optical system 26 are the first optical system. The first optical system forms the first optical image based on light from the subject in an imaging region S1 of the imaging device 22. An optical path which passes through the first optical system is a first optical path L1. The concave lens 23b, the convex lens 24b, and the image forming optical system 26 are the second optical system. The second optical system forms a second optical image based on the light from the subject in the imaging region S1 of the imaging device 22. The optical path that passes through the second optical system is a second optical path L2.

Under the first imaging condition, the switching unit 25 causes light that passes through the first optical system to be incident on the imaging device 22 and blocks light that passes through the second optical system. Under the second imaging condition, the switching unit 25 causes light that passes through the second optical system to be incident on the imaging device 22 and blocks light that passes through the first optical system. The switching control unit 36 switches the optical image formed on the imaging device 22 between the first optical image and the second optical image by controlling the switching unit 25.

The switching unit 25 forms only either one of the first optical image of the subject and the second optical image of the subject in the imaging region S1 of the imaging device 22 by setting either one of the first optical path L1 and the second optical path L2 as an imaging optical path. The first optical path L1 and the second optical path L2 are different from each other. The first optical image of the subject is formed by light passing through the first optical path L1. The second optical image of the subject is formed by light passing through the second optical path L2.

An optical axis on a subject side of the second optical system is substantially parallel to an optical axis on a subject side of the first optical system. The second optical system has parallax with respect to the first optical system. That is, the first optical system and the second optical system are separated in a parallax direction. The parallax direction is a direction of a straight line that passes through an optical center (a principal point) of the first optical system and an optical center (a principal point) of the second optical system. The parallax direction is substantially orthogonal to the optical axis of each optical system. The light incident on the first optical system passes through the first optical path L1. The light incident on the second optical system passes through the second optical path L2 different from the first optical path L1. The first optical system forms the first optical image of the subject and the second optical system forms the second optical image of the subject.

The switching unit 25 switches the imaging optical path between the first optical path L1 and the second optical path L2. The switching unit 25 causes only light that passes through either one of the first optical path L1 and the second optical path L2 to be transmitted and blocks light that passes through the other. For example, the switching unit 25 includes a shutter (a shielding plate) inserted into only either one of the first optical path L1 and the second optical path L2. When the switching unit 25 causes the light of the first optical path L1 to be transmitted, the shutter is inserted into the second optical path L2 and the light of the second optical path L2 is blocked. When the switching unit 25 causes the light of the second optical path L2 to be transmitted, the shutter is inserted into the first optical path L1 and the light of the first optical path L1 is blocked. The operation of the switching unit 25 is controlled by a control signal from the switching control unit 36. The switching unit 25 may be a liquid crystal shutter including a polarizing plate and a liquid crystal cell. The switching unit 25 is not limited to the above-described configuration.

The image forming optical system 26 forms a subject image based on either one of the light passing through the first optical path L1 and the light passing through the second optical path L2 in the imaging region S1 of the imaging device 22. The subject image formed in the imaging region S1 of the imaging device 22 is based on light passing through only an imaging optical path between the first optical path L1 and the second optical path L2. The imaging optical path is either one of the first optical path L1 and the second optical path L2.

The optical adapter 21 and the insertion unit 20 may be integrated. That is, the configuration inside the optical adapter 21 may be disposed on the tip of the insertion unit 20.

The first optical image of the subject is formed on the basis of the light passing through the first optical path L1. The second optical image of the subject is formed on the basis of light passing through the second optical path L2. The first optical image and the second optical image are incident in the imaging region S1 of the imaging device 22. The imaging device 22 captures the first optical image and the second optical image. The imaging device 22 captures the first optical image formed by the first optical system at a first imaging timing. The imaging device 22 captures the second optical image formed by the second optical system at a second imaging timing. The first imaging timing and the second imaging timing are different from each other.

The imaging device 22 consecutively scans a plurality of rows in the array of the plurality of cells 54 one by one during each frame period of a plurality of frame periods. The imaging device 22 reads pixel signals from the cells 54 in a plurality of rows by consecutively scanning the plurality of rows one by one. The imaging device 22 generates a first image and a second image. The first image is formed on the basis of the first optical image formed in the imaging region S1. The second image is formed on the basis of the second optical image formed in the imaging region S1. The first image and the second image are image data including pixel values based on the pixel signals read from the cells 54 of the plurality of rows. The imaging device 22 outputs the first image and the second image to the video processing unit 31. The operation of the imaging device 22 is controlled by a control signal from the imaging control unit 30.

The plurality of imaging conditions include a first imaging condition and a second imaging condition. The first imaging condition and the second imaging condition are different from each other. Under the first imaging condition, the first optical path L1 is set as the imaging optical path. The imaging device 22 generates a first image of the subject by imaging the subject under the first imaging condition. Under the second imaging condition, the second optical path L2 is set as the imaging optical path. The imaging device 22 generates a second image of the subject by imaging the subject under the second imaging condition.

For example, a line exposure type of CMOS imager is used for the imaging device 22. By adopting a CMOS imager, the configuration of the endoscope device 1 can be simplified and the power consumption of the endoscope device 1 can be reduced.

A signal line 90 is disposed inside the insertion unit 20 and inside the main body unit 3. The signal line 90 is a composite coaxial line formed by bundling a plurality of coaxial cables. A tip side of the signal line 90 is connected to the imaging device 22, and a part of the coaxial cable on a base end side of the signal line 90 is connected to the imaging control unit 30. The imaging control unit 30 supplies electric power for driving to the imaging device 22 via the signal line 90. Also, the imaging control unit 30 outputs an imaging parameter received from the video processing unit 31 to the imaging device 22. Thereby, the imaging control unit 30 controls the imaging device 22.

The remaining coaxial cable on the base end side of the signal line 90 is connected to the video processing unit 31. The image generated by the imaging device 22 is transmitted to the video processing unit 31. The video processing unit 31 executes various types of video processing on the image output from the imaging device 22. For example, the video processing to be executed by the video processing unit 31 is at least one of demosaicing, digital gain adjustment, noise reduction, white balance adjustment, contour correction, and gamma correction. The video processing unit 31 synthesizes an image on which the video processing has been performed and graphic data generated by the CPU 34. Thereby, the video processing unit 31 generates a video signal for display. The video processing unit 31 outputs the generated video signal to the display unit 5.

Further, the video processing unit 31 generates control parameters for performing imaging with appropriate brightness. The video processing unit 31 generates imaging control parameters and illumination control parameters on the basis of an input image or an image on which the video processing has been performed. The imaging control parameters are parameters such as a line reading cycle, a frame rate, and an analog gain of the imaging device 22. The illumination control parameters are parameters such as an ON timing of the illumination light, an OFF timing of the illumination light, and a turning-on intensity. The video processing unit 31 outputs the imaging control parameters to the imaging control unit 30. The imaging control unit 30 controls the imaging device 22 on the basis of the imaging control parameters. The video processing unit 31 outputs the illumination control parameters to the illumination control unit 33. The illumination control unit 33 controls the white light source 37 on the basis of the illumination control parameters.

At least two of the imaging control unit 30, the illumination control unit 33, and the switching control unit 36 may be integrated. The imaging control unit 30, the illumination control unit 33, and the switching control unit 36 may include at least one of a processor and a logic circuit. For example, the processor is at least one of a CPU, a digital signal processor (DSP), and a graphics processing unit (GPU). For example, the logic circuit is at least one of an application specific integrated circuit (ASIC) and a field-programmable gate array (FPGA). The imaging control unit 30, the illumination control unit 33, and the switching control unit 36 can include one or more processors. The imaging control unit 30, the illumination control unit 33, and the switching control unit 36 can include one or more logic circuits.

A computer of the endoscope device 1 may read a program and execute the read program. The program includes commands defining operations of the imaging control unit 30, the illumination control unit 33, and the switching control unit 36. That is, the functions of the imaging control unit 30, the illumination control unit 33, and the switching control unit 36 may be implemented by software. For example, this program may be provided by a "computer-readable recording medium" such as a flash memory. The above-described program may be transmitted from a computer having a storage device or the like in which the program is stored to the endoscope device 1 via a transmission medium or transmission waves in the transmission medium. The "transmission medium" for transmitting the program refers to a medium having an information transmission function, for example, a network (a communication network) such as the Internet or a communication circuit (a communication line) such as a telephone circuit. Also, the above-described program may be a program for implementing some of the above-described functions. Further, the above-described program may be a program capable of implementing the above-described function in combination with a program already recorded on the computer, i.e., a so-called differential file (differential program). A combination of a program already recorded in the computer and a differential program may implement the above-described functions.

The CPU 34 controls each unit in the endoscope device 1. Further, the CPU 34 monitors the state of the operation unit 4. Thereby, the CPU 34 detects operations related to measurement and the like. The CPU 34 may be a DSP or a GPU. The CPU 34 may be an ASIC or an FPGA.

The memory 35 stores the image processed by the video processing unit 31. The memory 35 may store the image output from the imaging device 22. The memory 35 may be detachable from the endoscope device 1. The memory 35 is configured as a volatile or nonvolatile memory. For example, the memory 35 may be any one of a random access memory (RAM), a dynamic random access memory (DRAM), a static random access memory (SRAM), an erasable programmable read only memory (EPROM), an electrically erasable programmable read only memory (EEPROM), and a flash memory. Alternatively, the memory 35 may be a combination of at least two of the above-described memories. The endoscope device 1 may have a hard disk drive for storing images.

The operation unit 4 is a user interface that accepts instructions from the user. The user inputs instructions necessary for controlling various types of operations of the entire endoscope device 1 by operating the operation unit 4. The operation unit 4 outputs a signal indicating an instruction received from the user to the CPU 34. For example, the operation unit 4 is at least one of a button, a switch, a key, a mouse, a joystick, a touch pad, a track ball, and a touch panel.

The display unit 5 displays an image of the subject on the basis of video signals output from the video processing unit 31. Also, the display unit 5 displays operation control details, measurement results, and the like. For example, the operation control details are displayed as a menu. For example, the display unit 5 is at least one of a liquid crystal display and an organic electro luminescence (EL) display. The display unit 5 may be a touch panel display. In this case, the operation unit 4 and the display unit 5 are integrated.

Figure 3:
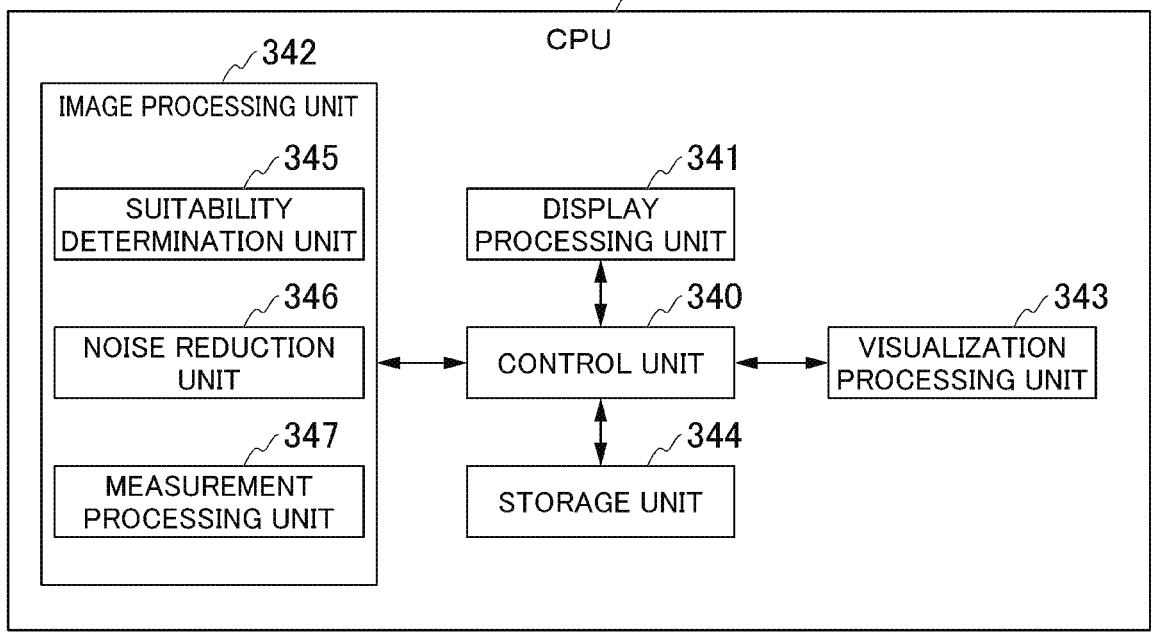
FIG. 3 is a block diagram showing a functional configuration of a CPU according to the first embodiment of the present invention.

FIG. 3 shows a functional configuration of the CPU 34. The functions of the CPU 34 include a control unit 340, a display processing unit 341, an image processing unit 342, a visualization processing unit 343, and a recording unit 344. At least one of blocks shown in FIG. 3 may include a circuit different from the CPU 34.

The control unit 340 controls a process to be executed by each unit. When the user operates the operation unit 4, the control unit 340 accepts an operation performed by the user. The display processing unit 341 generates graphic data for displaying a menu and the like. The graphic data generated by the display processing unit 341 is output to the video processing unit 31. Also, the display processing unit 341 controls the state of an image to be displayed on the display unit 5 by controlling the video processing unit 31.

The image processing unit 342 (an image processor) executes image processing on the basis of the image of the subject. The image processing unit 342 includes a suitability determination unit 345, a noise reduction unit 346, and a measurement processing unit 347.

The image processing unit 342 executes image processing on a plurality of images generated during a plurality of frame periods. The image processing unit 342 processes a plurality of images.

The switching control unit 36 causes the switching unit 25 to set the first imaging condition during a plurality of first frame periods. The switching control unit 36 causes the switching unit 25 to set the second imaging condition during a plurality of second frame periods. Each second frame period of the plurality of second frame periods is different from each first frame period of the plurality of first frame periods.

The imaging device 22 generates a plurality of at least one of first images of the subject and second images of the subject. The suitability determination unit 345 calculates at least one of a value indicating whether or not the plurality of first images are suitable for image processing and a value indicating whether or not the plurality of second images are suitable for the image processing.

The imaging device 22 generates the plurality of first images by imaging the subject under the first imaging condition. The imaging device 22 generates the plurality of second images by imaging the subject under the second imaging condition. The noise reduction unit 346 generates a third image by performing a noise reduction process on the basis of the input of the plurality of first images. The noise reduction unit 346 generates a fourth image by performing a noise reduction process on the basis of the input of the plurality of second images.

The image processing unit 342 performs a process different from the noise reduction process on the third image and the fourth image. Specifically, the measurement processing unit 347 calculates 3D coordinates of a plurality of points on a surface of the subject using a passive stereo method on the basis of the third image and the fourth image.

The measurement processing unit 347 measures at least one of a shape of the subject, dimensions of the subject, and a distance to the subject (a subject distance). For example, the shape of the subject is measured as a 3D point cloud or a mesh polygon. The 3D point cloud is a set of 3D coordinates of a plurality of points on the surface of the subject. The mesh polygon is a set of triangles having each point included in the 3D point cloud as its vertex. The dimensions of the subject are a distance between any two points on the subject, an area of a region including three or more points on the subject, and the like. The subject distance is a distance from the tip of the insertion unit 20 where the imaging device 22 is disposed to the subject. Specifically, the subject distance is a distance from the imaging device 22 to the subject. The subject distance may be a distance from a principal point of the first optical system or a principal point of the second optical system to the subject. The subject distance may be a distance from a surface of the subject side of the lens to the subject. The measurement processing unit 347 performs stereo measurement by triangulation using disparities of the two images. Specifically, the measurement processing unit 347 detects a point corresponding to a measurement point set in the first image or the third image from the second image or the fourth image. This process is referred to as a template matching process. The measurement processing unit 347 calculates 3D coordinates of a point on the subject corresponding to the measurement point coordinates on the basis of the coordinates of the detected point (corresponding point coordinates) and the coordinates of the measurement point (measurement point coordinates). The measurement point is associated with an address of the cell 54 in the imaging region S1 of the imaging device 22. The measurement processing unit 347 may calculate 3D coordinates of only one point on the surface of the subject.

The result of the image processing executed by the image processing unit 342 is output to the visualization processing unit 343. The visualization processing unit 343 is a data generation unit (a data generator). The visualization processing unit 343 generates graphic data that is obtained by visualizing the image processing result. Thereby, the visualization processing unit 343 generates graphic data that is obtained by representing the result of reconstructing a 3D shape of the subject as an image.

Figure 6:
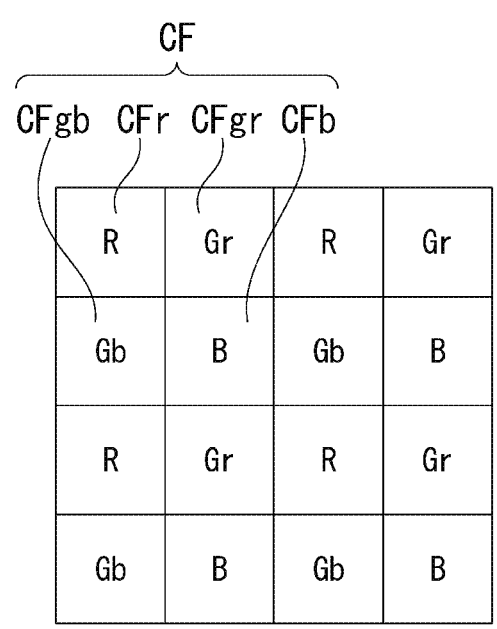
FIG. 6 is a diagram showing an array of color filters according to the first embodiment of the present invention.

In the first embodiment, the illumination light is white light. The imaging device 22 has a red color filter, a green color filter, and a blue color filter. Each color filter is shown in FIG. 6. Each color filter will be described below. The imaging device 22 generates a color image as an image of a subject. The color image includes a plurality of pixels. Each pixel has information indicating each of brightness of red, brightness of green, and brightness of blue as a pixel value. The image processing unit 342 generates 3D shape data (a color 3D point cloud or a mesh polygon with color texture) in which 3D coordinates (a 3D point cloud) of a plurality of points on the surface of the subject are associated with pixel values corresponding to the plurality of points. The visualization processing unit 343 generates graphic data that is obtained by visualizing the 3D shape data. The graphic data corresponds to an image that is obtained by disposing the 3D shape data within a virtual space and photographing the 3D shape data with a virtual camera disposed within the virtual space. In the 3D shape data generated by the image processing unit 342, 3D coordinates of each point included in a plurality of points on the surface of the subject are associated with a pixel value of each point included in the plurality of points. At least one of 3D shape data disposed in the virtual space by the visualization processing unit 343, a position of the camera, an orientation of the camera, and an angle of view of the camera is changed by the user operating the operation unit 4.

The graphic data generated by the visualization processing unit 343 is output to the video processing unit 31. The recording unit 344 records the image of the subject in the memory 35.

The operation unit 4 and the display unit 5 are optional.

FIG. 4 shows a configuration of the imaging device 22. The imaging device 22 shown in FIG. 4 includes a pixel unit 50, a vertical scanning unit 51, a signal processing unit 52, and a horizontal scanning unit 53.

The pixel unit 50 includes a plurality of cells 54 disposed in a matrix. The plurality of cells 54 are disposed in the imaging region S1 of the imaging device 22. Each of the number of rows and the number of columns in the array of the plurality of cells 54 is two or more. The number of rows and the number of columns may not be the same. Each cell 54 of the plurality of cells 54 generates a pixel signal corresponding to the amount of light incident on the cell 54. Each cell 54 of the plurality of cells 54 is connected to the vertical signal line 56. A plurality of vertical signal lines 56 are disposed. Each cell 54 of the plurality of vertical signal lines 56 is disposed for one column in the array of the plurality of cells 54. Each cell 54 of the plurality of cells 54 outputs the generated pixel signal to the vertical signal line 56.

Each cell 54 of the plurality of cells 54 is connected to the control signal line 57. A plurality of control signal lines 57 are disposed. Each control signal line 57 of the plurality of control signal lines 57 is disposed for one row in the array of the plurality of cells 54. Each control signal line 57 of the plurality of control signal lines 57 is connected to the vertical scanning unit 51. Control signals for controlling operations of the plurality of cells 54 are output from the vertical scanning unit 51 to the control signal line 57. The plurality of control signal lines 57 are disposed for cells 54 of one row. In FIG. 4, one control signal line 57 is shown for the cells 54 of one row and the other control signal lines 57 are omitted. Details of the control signals will be described below.

The operations of the plurality of cells 54 are controlled on the basis of the control signals output to the control signal lines 57. The control signals corresponding to the cells 54 of one row are supplied in common to all the cells 54 in the row. Thus, the same operation timing is set for two or more cells 54 disposed in the same row. That is, the two or more cells 54 disposed in the same row operate simultaneously. Details of the configuration of the cell 54 will be described below.

A control signal generated by the imaging control unit 30 is transmitted to the imaging device 22. The vertical scanning unit 51 generates the control signals for controlling the operations of the plurality of cells 54 on the basis of the control signal from the imaging control unit 30. The vertical scanning unit 51 generates control signals corresponding to each row of a plurality of rows in the array of the plurality of cells 54. The vertical scanning unit 51 outputs the generated control signals to the control signal lines 57.

The signal processing unit 52 includes a plurality of signal processing circuits 55. The signal processing circuit 55 is disposed for each column in the array of the plurality of cells 54. The signal processing circuit 55 is connected to the vertical signal line 56. The signal processing circuit 55 performs signal processing on a pixel signal output from the cell 54 to the vertical signal line 56. The signal processing to be performed by the signal processing circuit 55 includes correlated double sampling (CDS), analog gain control (AGC), and the like.

The pixel signal processed by the signal processing circuit 55 is input to the horizontal scanning unit 53. The horizontal scanning unit 53 sequentially selects columns in the array of the plurality of cells 54. The pixel signal corresponding to the column selected by the horizontal scanning unit 53 is output from the output terminal 58.

The imaging device 22 includes the plurality of cells 54 disposed in the matrix. During each frame period of the plurality of frame periods, the imaging device 22 generates pixel signals of the cells 54 based on an optical image of the subject. During each frame period of the plurality of frame periods, the imaging device 22 generates an image of the subject using the pixel signals.

Figure 5:
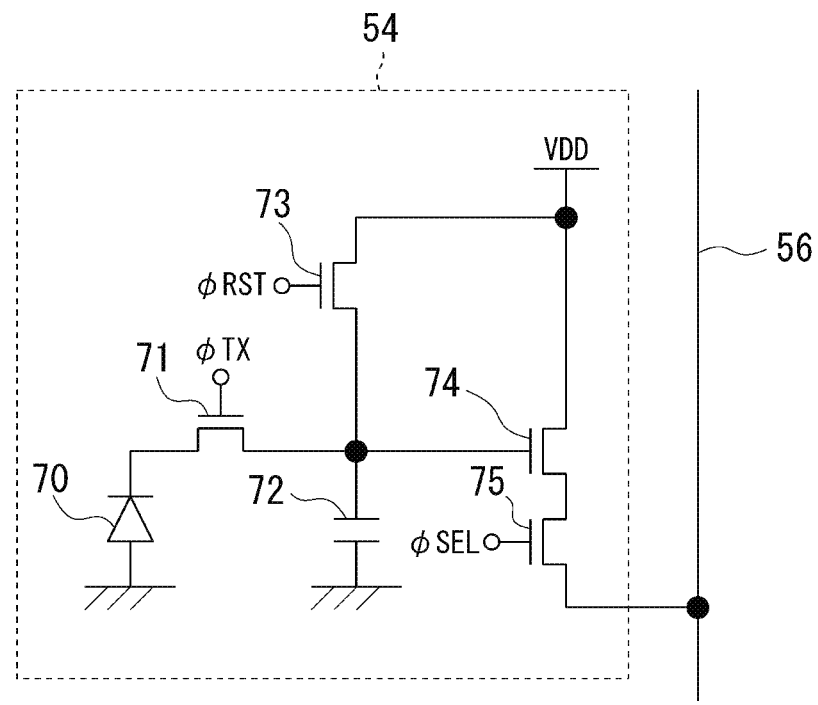
FIG. 5 is a circuit diagram showing a configuration of a pixel according to the first embodiment of the present invention.

FIG. 5 shows a configuration of the cell 54. The cell 54 shown in FIG. 5 includes a photoelectric conversion unit 70, a charge transfer unit 71, a charge holding unit 72, a capacitor reset unit 73, an amplification unit 74, and an output unit 75. The photoelectric conversion unit 70 is a photodiode. The charge holding unit 72 is a capacitor. The charge transfer unit 71, the capacitor reset unit 73, the amplification unit 74, and the output unit 75 are transistors.

The photoelectric conversion unit 70 generates and stores electric charge according to the amount of light incident on the cell 54. The charge transfer unit 71 transfers the electric charge generated and stored by the photoelectric conversion unit 70 to the charge holding unit 72. The charge holding unit 72 holds the electric charge transferred from the photoelectric conversion unit 70. The capacitor reset unit 73 resets the electric charge of the charge holding unit 72 on the basis of a power-supply voltage VDD. The capacitor reset unit 73 is turned on and therefore the capacitor reset unit 73 resets the electric charge of the charge holding unit 72. The amplification unit 74 amplifies a signal based on the electric charge held in the charge holding unit 72. The output unit 75 outputs the signal amplified by the amplification unit 74 as a pixel signal to the vertical signal line 56.

The operation of the charge transfer unit 71 is controlled by a control signal φTX. The operation of the capacitor reset unit 73 is controlled by a control signal φRST. The operation of the output unit 75 is controlled by a control signal φSEL. The control signal φTX, the control signal φRST, and the control signal φSEL are supplied from the vertical scanning unit 51 via the control signal line 57.

The operation of the cell 54 includes a capacitor reset operation, a charge transfer operation, and a signal reading operation. The capacitor reset operation corresponds to the operation of the capacitor reset unit 73. The charge transfer operation corresponds to the operation of the charge transfer unit 71. The signal reading operation corresponds to the operation of the output unit 75. A period from a storage start timing to a transfer timing is a period (an exposure period) during which exposure can be performed in the cell 54. The storage start timing is a timing at which the photoelectric conversion unit 70 starts generation of electric charge based on the light incident on the cell 54 and storage of the electric charge. The transfer timing is a timing at which the charge transfer unit 71 transfers the electric charge stored in the photoelectric conversion unit 70 to the charge holding unit 72. The cell 54 stores electric charge in accordance with the amount of light incident on the cell 54 during the exposure period of the cell 54. In the following description, a state in which the cell 54 has been reset represents a state of the cell 54 at a timing when the exposure period has ended and the charge transfer unit 71 has transferred the electric charge stored in the photoelectric conversion unit 70 to the charge holding unit 72.

The imaging device 22 reads the pixel signal from the cell 54 by outputting the pixel signal from the output unit 75. The imaging device 22 acquires an image by reading the pixel signal from the cell 54. The reading of pixel signals is equivalent to the acquisition of an image.

As shown in FIG. 6, the imaging device 22 includes color filters CF disposed in each cell 54. FIG. 6 shows an array of the color filters CF. The color filters CF include an R filter CFr, a G filter CFgr, a G filter CFgb, and a B filter CFb.

The R filter CFr is a red color filter. The R filter CFr causes red light to be transmitted and blocks other light. The G filter CFgr and the G filter CFgb are green color filters. The G filter CFgr and the G filter CFgb cause green light to be transmitted and block other light. The B filter CFb is a blue color filter. The B filter CFb causes blue light to be transmitted and blocks other light.

The array of the color filters CF shown in FIG. 6 is a Bayer array. In the Bayer array, a basic array is regularly and periodically disposed in the row direction and the column direction. The basic array includes one R filter CFr, two G filters CFgr and CFgb, and one B filter CFb.

The imaging device 22 generates an R signal based on the red light, a G signal based on the green light, and a B signal based on the blue light. The imaging device 22 outputs a color image including pixel values based on the R signal, the G signal, and the B signal.

Figure 7:
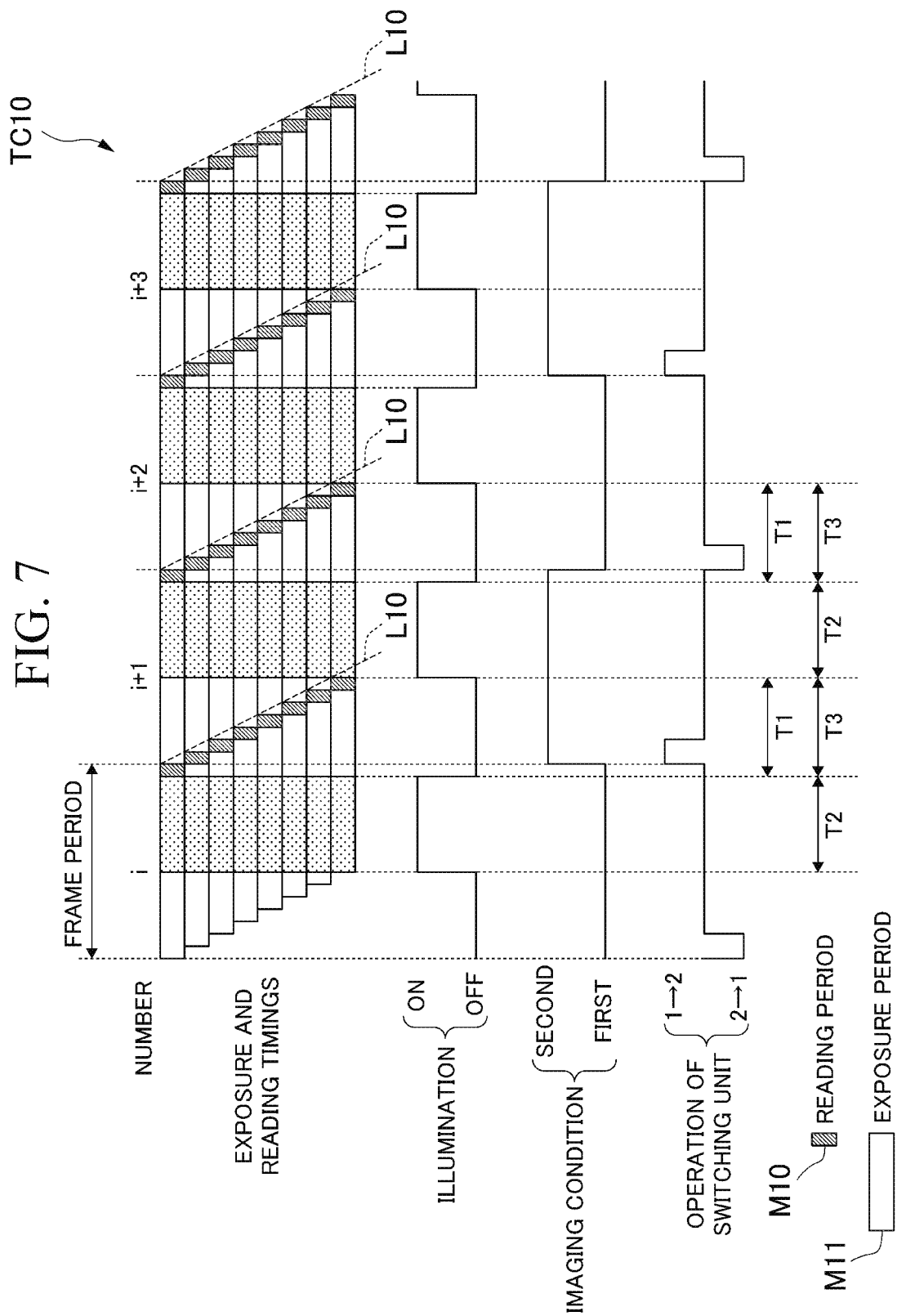
FIG. 7 is a timing chart showing an operation of the imaging device according to the first embodiment of the present invention.

FIG. 7 shows relationships between an operation of the imaging device 22 in a measurement mode, a state of illumination, and a state of an imaging condition. The operation of the imaging device 22 will be described with reference to FIG. 7. In the example shown in FIG. 7, the imaging region S1 of the imaging device 22 has eight rows. The number of rows of the imaging region S1 is not limited to eight.

A timing chart TC10 shows the operation of the imaging device 22. In the timing chart TC10, the horizontal direction represents time and the vertical direction represents a row position of the cell 54. The top row is a first row and the bottom row is an eighth row.

In the timing chart TC10, the state of illumination, i.e., the state of the white light source 37, is shown. The state of the white light source 37 is either one of ON and OFF. In the timing chart TC10, the imaging conditions, i.e., imaging optical paths, are shown. The imaging optical path is either one of the first optical path L1 and the second optical path L2. In the timing chart TC10, the operation of the switching unit 25 is shown. The operation of the switching unit 25 is either one of switching from the first optical path L1 to the second optical path L2 and switching from the second optical path L2 to the first optical path L1.

In the timing chart TC10, a frame rate is 60 fps. A length of each frame period is 1/60 sec. Each frame period includes an exposure period of cells 54 for one row and a reading period of cells 54 for one row. During a reading period of a certain row, the pixel signals of the cells 54 included in the row are read. The reading of the pixel signals includes the charge transfer and the signal reading. In the timing chart TC10, a frame period based on a start timing of the exposure period in the cells 54 of the first row is shown. Frame periods of the second to eighth rows are started with a delay of a predetermined time period from the frame period of a row immediately before each row. The pixel signal stored in the cell 54 during the exposure period of the frame period n is read from the cell 54 during the reading period of the frame period n. The exposure period of the frame period n is the exposure period of each of the first to eighth rows of the frame period n. The reading period of the frame period n is a period from the start of the reading period of the first row of the frame period n to the end of the reading period of the eighth row of the frame period n.

A broken line L10 in FIG. 7 indicates a start timing of the frame period of each row. Although the broken line L10 is omitted in timing charts other than the timing chart TC10, the meaning of the broken line L10 is common in the present specification. A symbol M10 in FIG. 7 indicates a reading period. A symbol M11 in FIG. 7 indicates an exposure period. Although the symbols M10 and M11 are omitted in the timing charts other than the timing chart TC10, the meanings of the symbols M10 and M11 are common in the present specification.

At a start timing of an exposure period of a frame period i, the cells 54 of the first row are reset. Thereby, the exposure period of the cells 54 of the first row is started. During the exposure period, signals based on the light incident on the cells 54 are stored in the cells 54. After the exposure period of the cells 54 of the first row is started, the exposure period of the cells 54 of the second row is started. Likewise, the exposure periods of the cells 54 of the third to eighth rows are sequentially started.

The vertical scanning unit 51 sequentially generates the control signals of the rows and sequentially outputs the generated control signals to the cells 54 of the rows. The imaging device 22 consecutively sequentially resets the cells 54 of the plurality of rows row by row on the basis of the control signals sequentially output from the vertical scanning unit 51. According to this resetting, the imaging device 22 sequentially starts the exposure periods of the cells 54 of a plurality of rows.

During a frame period (i−1) immediately before the frame period i, the imaging optical path of the acquired image is the second optical path L2. When the exposure period of the cells 54 of the first row during the frame period i has been started, switching of the imaging optical path is started. The switching control unit 36 outputs a control signal for switching the imaging optical path to the switching unit 25. Thereby, the switching control unit 36 causes the switching unit 25 to switch the imaging optical path. The switching unit 25 starts switching from the second optical path L2 to the first optical path L1 on the basis of the control signal from the imaging control unit 30. It is only necessary for switching from the second optical path L2 to the first optical path L1 to be started simultaneously with or after the start of the reading of the pixel signals of the cells 54 of the first row during the frame period (i−1) (the start of the reading period of the frame period (i−1)). Also, a timing at which the control signal is output from the imaging control unit 30 may be earlier than that of the start of the reading of the pixel signals of the cells 54 of the first row by a certain time period. The certain time is the same as or shorter than a time difference from an output timing of the control signal to a start timing of switching of the optical path. Thereby, the switching of the optical path is started simultaneously with or after the start of the reading of the pixel signals of the cells 54 of the first row.

When the exposure period of the cells 54 of the third row during the frame period i has been started, the switching unit 25 completes the switching from the second optical path L2 to the first optical path L1. The imaging optical path of the image acquired during the frame period i is the first optical path L1. It is only necessary for switching from the second optical path L2 to the first optical path L1 to be completed simultaneously with or before the start of the exposure period of the cells 54 of the eighth row during the frame period i (the end of the reading period of the frame period (i−1)).

When the exposure period of the cells 54 of the first row during the frame period i has been started, the white light source 37 is already turned off. When the exposure period of the cells 54 of the eighth row during the frame period i has been started, the turning on of the white light source 37 is started. The illumination control unit 33 causes the white light source 37 to be turned on by outputting a turning-on control signal to the white light source 37. The white light source 37 starts the turning on thereof on the basis of a control signal from the illumination control unit 33. The turning on of the white light source 37 may be started after the start of the exposure period of the cells 54 of the eighth row during the frame period i (the end of the reading period of the frame period (i−1)).

When the exposure period of the cells 54 of the first row during the frame period i has ended, the reading period of the cells 54 of the first row during the frame period i is started. The cells 54 of the first row output pixel signals to the vertical signal lines 56. When a predetermined time period has elapsed from a timing at which the reading period of the cells 54 of the first row has been started, the reading period of the cells 54 of the first row ends. At this moment, the cells 54 of the first row are reset and the exposure period of the cells 54 of the first row during the frame period (i+1) is started.

When the reading period of the cells 54 of the first row during the frame period i has been started, the turning-on of the white light source 37 ends. The illumination control unit 33 causes the white light source 37 to be turned off by outputting a turning-off control signal to the white light source 37. The white light source 37 is turned off on the basis of the control signal from the illumination control unit 33. The end of the turning-on of the white light source 37 may be earlier than the start of the reading period of the cells 54 of the first row during the frame period i (the start of the reading period of the frame period i).

In the timing chart TC10 shown in FIG. 7, the illumination control unit 33 causes the white light source 37 to be intermittently turned on. The white light source 37 is intermittently turned on. A period during which the white light source 37 is continuously turned on overlaps the exposure periods of the cells 54 of the plurality of rows. During the period in which the white light source 37 is continuously turned on, the cells 54 of all rows are simultaneously exposed. A period (an imaging period) during which light from the subject is incident on the cells 54 in accordance with the turning-on of the white light source 37 is common in all the cells 54 of all the rows. That is, global exposures (simultaneous exposures) of the cells 54 of the plurality of rows are performed on the basis of control of a turning-on timing of the white light source 37 and a turning-off timing of the white light source 37. A period during which the white light source 37 is continuously turned on does not include the reading period of the cell 54.

When the reading period of the cells 54 of the first row during the frame period i has ended, the reading period of the cells 54 of the second row during the frame period i is started. The cells 54 of the second row output pixel signals to the vertical signal lines 56. When a predetermined time period has elapsed from a timing when the reading period of the cells 54 of the second row has been started, the reading period of the cells 54 of the second row ends. At this moment, the cells 54 of the second row are reset and the exposure period of the cells 54 of the second row during the frame period (i+1) is started. Likewise, the reading periods of the cells 54 of the third to eighth rows are sequentially started, and the pixel signals of the cells 54 of the third row to the eighth row are sequentially read. The cells 54 of the third to eighth rows are sequentially reset and the exposure periods of the cells 54 of the third to eighth rows during the frame period (i+1) are sequentially started.

The vertical scanning unit 51 sequentially generates control signals of the rows and sequentially outputs the generated control signals to the cells 54 of the rows. The imaging device 22 consecutively scans the cells 54 of the plurality of rows row by row on the basis of the control signals sequentially output from the vertical scanning unit 51. According to this scanning, the imaging device 22 sequentially reads pixel signals from the cells 54 of the plurality of rows.

A method of driving the imaging device 22 is a rolling shutter method. In the rolling shutter method, the rows to be read are changed one by one during the reading period of one frame period and the pixel signals are consecutively read from the cells 54 of the rows. In the rolling shutter method, exposure periods are sequentially started row by row and pixel signals are sequentially read row by row. The cells 54 of the row in which pixel signal reading is completed are reset and the exposure period of the next frame period is started.

When the reading period of the cells 54 of the first row during the frame period i has ended, switching of the imaging optical path is started. The switching control unit 36 outputs a control signal for switching of the imaging optical path to the switching unit 25. Thereby, the switching control unit 36 causes the switching unit 25 to switch the imaging optical path. The switching unit 25 starts switching from the first optical path L1 to the second optical path L2 on the basis of a control signal from the imaging control unit 30. It is only necessary for the switching from the first optical path L1 to the second optical path L2 to be started simultaneously with or after the start of the reading of the cells 54 of the first row during the frame period i (the start of the reading period of the frame period i).

When the reading period of the cells 54 of the third row during the frame period i has ended, the switching unit 25 completes switching from the first optical path L1 to the second optical path L2. The imaging optical path of the image acquired during the frame period (i+1) is the second optical path L2. It is only necessary for switching from the first optical path L1 to the second optical path L2 to be completed simultaneously with or before the start of the exposure period of the cells 54 of the eighth row during the frame period (i+1) (the end of the reading period of the frame period i).

When the reading period of the cells 54 of the eighth row during the frame period i has ended, the turning-on of the white light source 37 is started. The illumination control unit 33 causes the white light source 37 to be turned on by outputting a turning-on control signal to the white light source 37. The white light source 37 starts turning-on on the basis of the control signal from the illumination control unit 33. The turning-on of the white light source 37 may be started after the end of the reading period of the cells 54 of the eighth row during the frame period i (the end of the reading period of the frame period i).

During each frame period before the frame period i, the imaging device 22 executes the same operation as the operation during the frame period i. During each frame period before the frame period i, the white light source 37 is intermittently turned on. During each frame period before the frame period i, the switching unit 25 switches the imaging optical path to the first optical path L1 or the second optical path L2.

When the exposure period of the cells 54 of the first row during the frame period (i+1) has ended, the reading period of the cells 54 of the first row during the frame period (i+1) is started. As in the operation during the frame period i, the reading periods of the cells 54 of the first to eighth rows are sequentially started and the pixel signals of the cells 54 of the first to eighth rows are sequentially read. The cells 54 of the first to eighth rows are sequentially reset and the exposure periods of the cells 54 of the first to eighth rows during the frame period (i+2) are sequentially started.

When the reading period of the cells 54 of the first row during the frame period (i+1) has been started, the turning-on of the white light source 37 ends. The illumination control unit 33 causes the white light source 37 to be turned off by outputting a turning-off control signal to the white light source 37. The white light source 37 is turned off on the basis of a control signal from the illumination control unit 33. The turning-on of the white light source 37 may be ended before the start of the reading period of the cells 54 of the first row during the frame period (i+1) (the start of the reading period of the frame period (i+1)).

When the reading period of the cells 54 of the first row during the frame period (i+1) has ended, the switching of the imaging optical path is started. The switching control unit 36 outputs a control signal for switching the imaging optical path to the switching unit 25. Thereby, the switching control unit 36 causes the switching unit 25 to switch the imaging optical path. The switching unit 25 starts switching from the second optical path L2 to the first optical path L1 on the basis of the control signal from the imaging control unit 30. It is only necessary for the switching from the second optical path L2 to the first optical path L1 to be started simultaneously with or after the start of reading of the cells 54 of the first row during the frame period (i+1) (the start of the reading period during the frame period (i+1)).

When the reading period of the cells 54 of the third row during the frame period (i+1) has ended, the switching unit 25 completes switching from the second optical path L2 to the first optical path L1. The imaging optical path of the image acquired during the frame period (i+2) is the first optical path L1. It is only necessary for switching from the second optical path L2 to the first optical path L1 to be completed simultaneously with or before the start of the exposure period of the cells 54 of the eighth row during the frame period (i+2) (the end of the reading period of the frame period (i+1)).

During the frame period (i+2) and the frame period (i+3), the imaging device 22 executes the same operation as the operation during the frame period i.

The white light source 37 is turned on during the exposure period in each of the frame period (i+2) and the frame period (i+3). The white light source 37 is iteratively turned on and off. The white light source 37 is turned on during each frame period and is turned off during each frame period.

The switching unit 25 switches the imaging optical path during the reading period in each of the frame period (i+2) and the frame period (i+3). The switching unit 25 iterates switching from the first optical path L1 to the second optical path L2 and switching from the second optical path L2 to the first optical path L1. The switching unit 25 switches the imaging optical path during each frame period.

While the endoscope device 1 is operating in the measurement mode, the endoscope device 1 consecutively or intermittently iterates the operation during the frame periods i to (i+3).

In the timing chart TC10 shown in FIG. 7, pixel signals are read from the cells 54 of the first to eighth rows. That is, the pixel signals are read from all of the plurality of cells 54. The pixel signals may be read from the cells 54 of only some rows. For example, pixel signals may be read from cells 54 of a row other than a row including only optical black pixels or pixel signals may be read from cells 54 of only a valid row that is a row including valid pixels. When pixel signals are read from the cells 54 of only some rows, a period during which the white light source 37 is continuously turned on may overlap a period during which the cells 54 of only some rows are simultaneously exposed. The numbers of the first to eighth rows indicate an order of reading. The numbers may be different from those of a physical order on an imaging plane. For example, the cells 54 may be physically disposed in descending order from the eighth row. Alternatively, the cells 54 may be disposed in the order of the first row, the fifth row, the second row, the sixth row, the third row, the seventh row, the fourth row, and the eighth row in a predetermined direction.

During a first period T1, the imaging device 22 sequentially reads pixel signals from at least some of the plurality of cells 54 row by row. During the first period T1, the imaging device 22 sequentially reads pixel signals from the cells 54 of simultaneous exposure rows row by row. The simultaneous exposure rows are at least some of the plurality of rows in the array of the plurality of cells 54. The simultaneous exposure rows include cells 54 to be simultaneously exposed by turning on the white light source 37. In the timing chart TC10 shown in FIG. 7, all rows are simultaneous exposure rows and the first period T1 of the frame period n is a period from the start of the reading of the pixel signals in the cells 54 of the first row of the frame period n to the completion of the reading of the pixel signals in the cells 54 of the eighth row (the reading period of the frame period n).

In the timing chart TC10 shown in FIG. 7, the white light source 37 is turned on simultaneously with the completion of reading of pixel signals during one frame period. That is, the white light source 37 is turned on simultaneously with the completion of the first period T1. The white light source 37 is turned off simultaneously with the start of the reading of pixel signals during one frame period. That is, the white light source 37 is turned off simultaneously with the start of the first period T1.

The illumination control unit 33 causes the white light source 37 to generate the illumination light during the second period T2. The white light source 37 is continuously turned on during the second period T2. The second period T2 is at least a part of a period other than the first period T1. In the timing chart TC10 shown in FIG. 7, the second period T2 is all of the period other than the first period T1.

The illumination control unit 33 causes the white light source 37 to stop the generation of the illumination light during the third period T3. The white light source 37 is continuously turned off during the third period T3. The third period T3 is all of a period other than the second period T2. The third period T3 is a period including all of the first period T1. In the timing chart TC10 shown in FIG. 7, the third period T3 is the same as the first period T1.

The second period T2 overlaps the exposure periods of a plurality of rows in the array of the plurality of cells 54. When the reading period of the row finally scanned by the imaging device 22 during one frame period has been completed, the second period T2 is started. When the reading period of the row first scanned by the imaging device 22 during one frame period has been started, the second period T2 is completed.

The switching control unit 36 causes the switching unit 25 to start switching of the imaging optical path during the third period T3 and complete the switching of the imaging optical path during the third period T3. That is, before the next second period T2 is started, the switching control unit 36 causes the switching unit 25 to complete switching of the imaging optical path. In the timing chart TC10 shown in FIG. 7, because the third period T3 is the same as the first period T1, the switching unit 25 starts switching of the imaging optical path during the first period T1 and completes the switching of the imaging optical path during the first period T1.

During the first period T1, the imaging device 22 reads pixel signals of one frame in a time period which is less than or equal to half a length of a sum of the exposure period and the reading period of the cells 54 of a row of each frame period of the plurality of frame periods. That is, the imaging device 22 reads pixel signals of one frame in a time period which is less than or equal to half the length of the frame period. By shortening a time period required for reading the pixel signals of the cells 54, the imaging device 22 can lengthen a period (a simultaneous exposure period) during which at least some of the plurality of cells 54 can be simultaneously exposed. Thus, the sensitivity of imaging is improved. In the timing chart TC10 shown in FIG. 7, the frame period is about 1/60 sec and the simultaneous exposure period corresponding to all the cells 54 is about 1/120 sec.

A time period in which the imaging device 22 reads the pixel signals from the cells 54 of one row is less than or equal to a time period Tr. The time period Tr is represented by the following Eq. (1). A number m is an integer of 2 or more which is the number of simultaneous exposure rows of the imaging device 22. The simultaneous exposure period of cells 54 of m rows includes all of the second period T2 during which the white light source 37 is continuously turned on. In Eq. (1), a time period Tf is a length of the frame period.

$$Tr=Tf/(m\times2) \qquad (1)$$

The second period T2 does not overlap the third period during which switching of the imaging optical path is executed. While the white light source 37 is turned on, the imaging optical path is fixed. That is, while the plurality of cells 54 are being exposed, the imaging optical path is fixed. An image output from the imaging device 22 is generated on the basis of only one of the first optical image and the second optical image.

The measurement processing unit 347 executes a measurement process on the basis of the first image and the second image. The first image is acquired during the first frame period and the second image is acquired during the second frame period. The first frame period and the second frame period are two consecutive frame periods. An interval between a first acquisition timing and a second acquisition timing is the same as one frame period. The first acquisition timing is a timing at which the imaging device 22 acquires the first image. The second acquisition timing is a timing at which the imaging device 22 acquires the second image.

Figure 8:
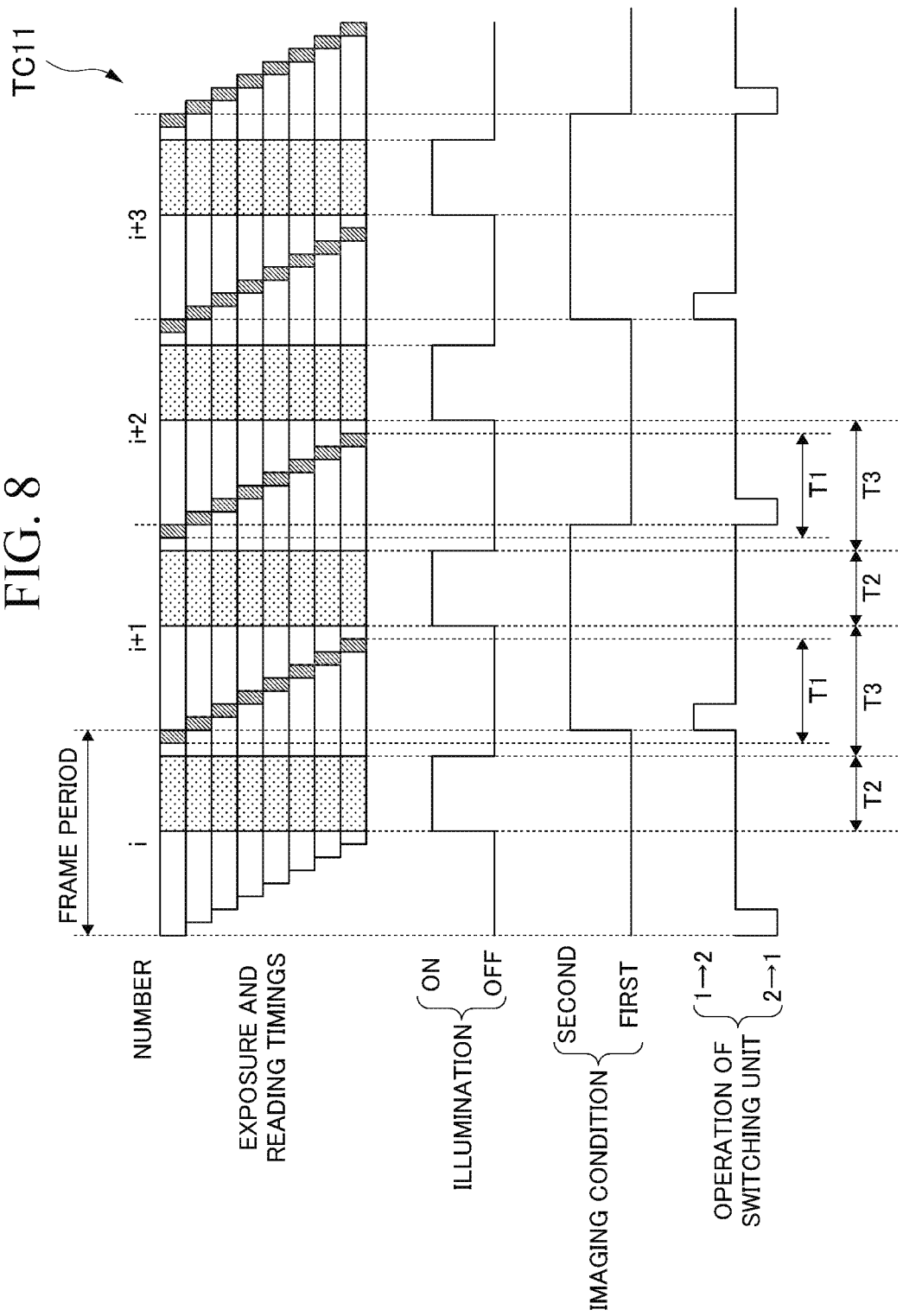
FIG. 8 is a timing chart showing an operation of the imaging device according to the first embodiment of the present invention.

FIG. 8 shows another example of relationships between an operation of the imaging device 22 in the measurement mode, a state of illumination, and a state of an imaging condition. The operation of the imaging device 22 will be described with reference to FIG. 8. Descriptions of parts that are the same as those shown in FIG. 7 will be omitted.

A timing chart TC11 shows the operation of the imaging device 22. The length of the second period T2 is different in the timing chart TC10 and the timing chart TC11.

The white light source 37 is turned on after the completion of reading of pixel signals during one frame period. That is, the white light source 37 is turned on after completion of the first period T1. The white light source 37 is turned off before the start of reading of pixel signals during one frame period. That is, the white light source 37 is turned off before the start of the first period T1.

The second period T2 during which the white light source 37 is continuously turned on is a part of a period other than the first period T1. In the timing chart TC11 shown in FIG. 8, the sum of the length of the first period T1 and the length of the second period T2 is shorter than the length of the frame period.

The third period T3 during which the white light source 37 is continuously turned off is all of the period other than the second period T2. In the timing chart TC11 shown in FIG. 8, the third period T3 is different from the first period T1.

The second period T2 is started after the reading period of the row finally scanned by the imaging device 22 during one frame period is completed. The second period T2 is completed before the reading period of the row first scanned by the imaging device 22 during one frame period is started. The difference between the timing of the start of the second period T2 and the timing of the end of the second period T2 between the timing chart TC10 shown in FIG. 7 and the timing chart TC11 shown in FIG. 8 (the length of the second period T2) is a result of automatic exposure (AE) control to be executed by the video processing unit 31.

Figure 9:
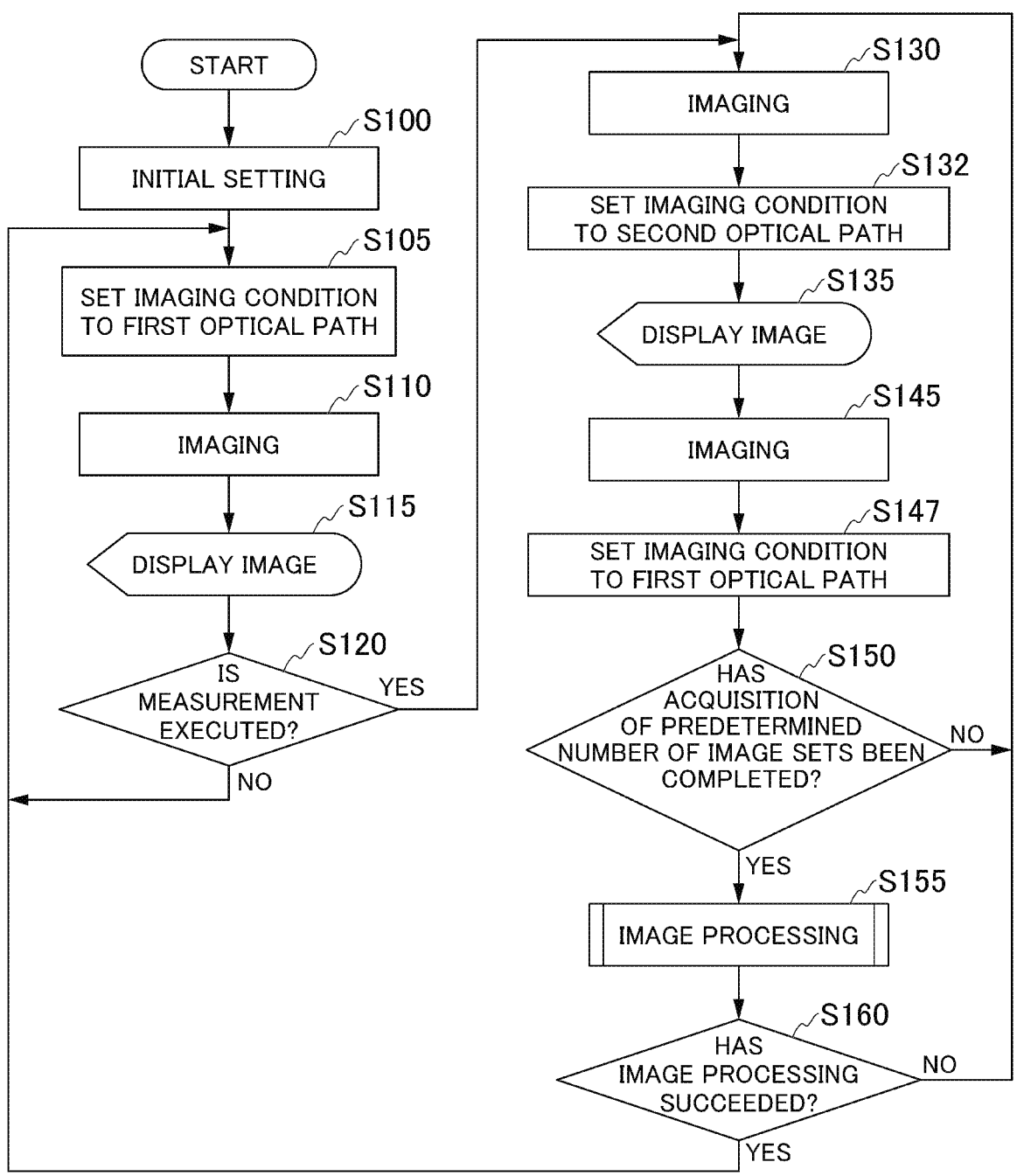
FIG. 9 is a flowchart showing a procedure of an operation of the endoscope device according to the first embodiment of the present invention.

FIG. 9 shows a procedure of the operation of the endoscope device 1. The operation of the endoscope device 1 will be described with reference to FIG. 9.

When the endoscope device 1 has been activated, the endoscope device 1 operates in the observation mode. When the endoscope device 1 has been activated, initial setting is executed. In the initial setting, the imaging control unit 30 sets simultaneous exposure rows in the imaging device 22. The simultaneous exposure rows include cells 54 to be simultaneously exposed in accordance with the turning-on of the white light source 37. In the timing chart TC10 shown in FIG. 7 and the timing chart TC11 shown in FIG. 8, all the rows in the array of the plurality of cells 54 are simultaneously exposed. In the initial setting, the imaging control unit 30 sets the length of the frame period in the imaging device 22. In the initial setting, the imaging control unit 30 sets a length of the first period T1 during which the imaging device 22 reads the pixel signals in the imaging device 22. The illumination control unit 33 causes the white light source 37 to be turned on (step S100).

After step S100, the switching control unit 36 outputs a control signal for switching the imaging optical path to the switching unit 25. Thereby, the switching control unit 36 causes the switching unit 25 to start switching of the imaging optical path. The switching unit 25 starts switching from the second optical path L2 to the first optical path L1 on the basis of the control signal from the switching control unit 36. Thereafter, the switching control unit 36 causes the switching unit 25 to complete the switching of the imaging optical path (step S105). When the imaging optical path is already the first optical path L1 in step S105, the processing in step S105 is unnecessary.

After step S105, the imaging device 22 generates an image of one frame and outputs the generated image. The imaging device 22 consecutively scans the cells 54 of the plurality of rows row by row during each frame period and sequentially reads the pixel signals from the cells 54 of the plurality of rows during each frame period. During each frame period, the imaging device 22 outputs an image based on the pixel signals of the cells 54 of the plurality of rows. Because the imaging optical path is the first optical path L1, the imaging device 22 outputs the first image. The video processing unit 31 processes the first image output from the imaging device 22. The first image processed by the video processing unit 31 is output to the display processing unit 341 and the CPU 34 (step S110).

After step S110, the display processing unit 341 causes the display unit 5 to display the first image generated in step S110. The display unit 5 displays the first image (step S115).

After step S115, the control unit 340 determines whether or not to execute measurement (step S120). For example, when the user has input a measurement instruction by operating the operation unit 4, the control unit 340 determines to perform measurement in step S120. The measurement may be executed at a predetermined cycle. For example, when a predetermined time period has elapsed from the activation of the endoscope device 1, the control unit 340 determines to execute the measurement. Alternatively, when a predetermined time period has elapsed from the execution of the previous measurement, the control unit 340 determines to execute the measurement.

When the control unit 340 determines not to execute the measurement in step S120, the processing in step S105 is executed. Until a measurement instruction is input, the imaging optical path is maintained as the first optical path L1. Until the measurement instruction is input, the imaging device 22 sequentially outputs first images and the display unit 5 sequentially updates and displays the first images.

When the control unit 340 determines to execute the measurement in step S120, the endoscope device 1 operates in the measurement mode. The imaging device 22 generates an image of one frame and outputs the generated image. Because the imaging optical path is the first optical path L1, the imaging device 22 outputs the first image. The illumination control unit 33 causes the white light source 37 to be turned on during the second period. During the third period, the illumination control unit 33 causes the white light source 37 to be turned off (step S130).

After step S130, the switching control unit 36 outputs a control signal for switching the imaging optical path to the switching unit 25. Thereby, the switching control unit 36 causes the switching unit 25 to start switching of the imaging optical path. The switching unit 25 starts switching from the first optical path L1 to the second optical path L2 on the basis of the control signal from the switching control unit 36. Thereafter, the switching control unit 36 causes the switching unit 25 to complete switching of the imaging optical path (step S132). Actually, while the imaging device 22 is reading the pixel signals in step S130, the processing in step S132 is executed.

After step S132, the display processing unit 341 causes the display unit 5 to display the first image generated in step S130. The display unit 5 displays the first image (step S135).

After step S135, the imaging device 22 generates an image of one frame and outputs the generated image. Because the imaging optical path is the second optical path L2, the imaging device 22 outputs a second image. The illumination control unit 33 causes the white light source 37 to be turned on during the second period. During the third period, the illumination control unit 33 causes the white light source 37 to be turned off (step S145).

After step S145, the switching control unit 36 outputs a control signal for switching the imaging optical path to the switching unit 25. Thereby, the switching control unit 36 causes the switching unit 25 to start switching of the imaging optical path. The switching unit 25 starts switching from the second optical path L2 to the first optical path L1 on the basis of the control signal from the switching control unit 36. Thereafter, the switching control unit 36 causes the switching unit 25 to complete switching of the imaging optical path (step S147). Actually, while the imaging device 22 is reading the pixel signal in step S145, the processing in step S147 is executed.

After step S147, the control unit 340 determines whether or not the acquisition of a predetermined number of image sets has been completed. One image set is a combination of one first image and one second image. The first image included in the image set and the second image included in the image set are acquired during consecutive frame periods. For example, the predetermined number is 2 (step S150).

When the control unit 340 determines that the acquisition of a predetermined number of image sets has not been completed in step S150, the processing in step S130 is executed. The imaging optical path is iteratively switched between the first optical path L1 and the second optical path L2 until a predetermined number of image sets are acquired. The imaging device 22 iteratively outputs first images and second images. When the first image and the second image mutually having parallaxes are alternately displayed, visibility deteriorates. Thus, the display unit 5 continuously sequentially updates and displays the first images without displaying the second images.

When the control unit 340 determines that the acquisition of a predetermined number of image sets has been completed in step S150, the image processing unit 342 executes image processing (step S155).

After step S155, the control unit 340 determines whether or not the image processing has succeeded on the basis of a processing result generated in step S155 (step S160). When the control unit 340 determines that the image processing has succeeded in step S160, the processing in step S105 is executed. When the control unit 340 determines that the image processing has failed in step S160, the processing in step S130 is executed.

The image output from the imaging device 22 may not be processed. Therefore, step S155 is optional. The display unit 5 may not display an image. Therefore, steps S115 and S135 are optional.

One image set may be acquired. Therefore, after step S145, the processing in step S155 may be executed. In this case, the processing in step S150 is not executed.

After step S105, the processing in step S130 may be executed. In this case, the processing in steps S110 to S120 is not executed.

Figure 10:
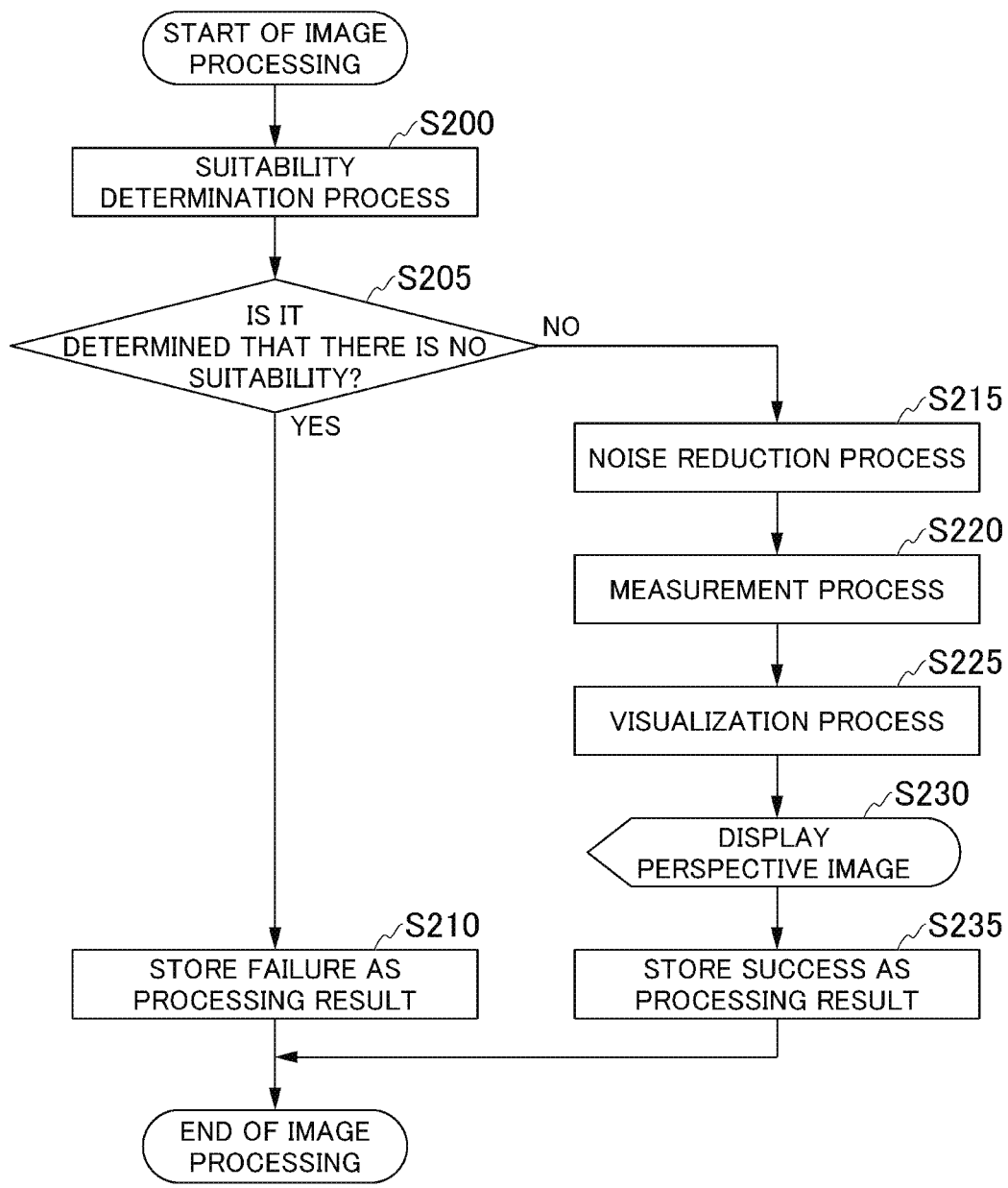
FIG. 10 is a flowchart showing a procedure of the operation of the endoscope device according to the first embodiment of the present invention.

FIG. 10 shows details of the image processing in step S155. The operation of the endoscope device 1 will be described with reference to FIG. 10.

An image set A and an image set B are input to the CPU 34. Each of image set A and image set B includes one first image and one second image.

The suitability determination unit 345 calculates a determination parameter for determining whether or not the image set is suitable for image processing of a subsequent stage. Specifically, the suitability determination unit 345 executes a motion detection process. In the motion detection process, the suitability determination unit 345 calculates a first value indicating first motion between two frames on the basis of a first image of a set A and a first image of a set B. In the motion detection process, the suitability determination unit 345 calculates a second value indicating second motion between two frames on the basis of a second image of the set A and a second image of the set B. For example, the suitability determination unit 345 calculates an absolute value of the difference between pixel values of two images for each pixel of the image. The suitability determination unit 345 calculates a sum of absolute values of differences between pixel values of all pixels of the image. The suitability determination unit 345 calculates a first value and a second value as determination parameters. The first value is a sum of absolute values of differences between pixel values calculated from two first images. The second value is a sum of absolute values of differences between pixel values calculated from two second images. The motion detection method may be another method such as motion vector calculation. Other than the motion detection process, a process of calculating the determination parameters in the suitability determination process may be another method such as a contrast detection process or a brightness determination process. Alternatively, the process of calculating the determination parameters in the suitability determination process may be a combination thereof (step S200).

After step S200, the suitability determination unit 345 determines whether or not the image set is suitable for image processing of the subsequent stage on the basis of the calculated parameters. The suitability determination unit 345 determines whether or not each determination parameter is less than a predetermined value. When the suitability determination unit 345 determines that all determination parameters are less than the predetermined value, the suitability determination unit 345 determines that the image set is suitable (has suitability) for the image processing of the subsequent stage. When the suitability determination unit 345 determines that at least one of the determination parameters is greater than or equal to the predetermined value, the suitability determination unit 345 determines that the image set is not suitable (does not have suitability) for the image processing of the subsequent stage (step S205).

If the suitability determination unit 345 determines that there is no suitability in step S205, the control unit 340 stores a failure as a processing result (step S210). When the suitability determination unit 345 determines that there is no suitability, the image processing unit 342 stops the image processing. Specifically, the noise reduction unit 346 stops the noise reduction process, the measurement processing unit 347 stops the measurement process, and the visualization processing unit 343 stops the visualization process. After step S210, the processing in step S160 is executed.

When the suitability determination unit 345 determines that there is suitability in step S205, the noise reduction unit 346 executes a noise reduction process. In the noise reduction process, the noise reduction unit 346 generates a first NR image (a third image) on the basis of the first image of the set A and the first image of the set B. A pixel value of the first NR image is an addition average of the pixel values between the two first images. In the noise reduction process, the noise reduction unit 346 generates a second NR image (a fourth image) on the basis of the second image of the set A and the second image of the set B. A pixel value of the second NR image is an addition average of the pixel values between the two second images (step S215).

After step S215, the measurement processing unit 347 executes a measurement process. In the measurement process, the measurement processing unit 347 generates a first corrected image by correcting optical distortion of the first NR image. In the measurement process, the measurement processing unit 347 generates a second corrected image by correcting the optical distortion of the second NR image. In the measurement process, the measurement processing unit 347 acquires a disparity distribution in a template matching process using the first NR image and the second NR image. The disparity distribution includes disparity information in each pixel of a plurality of pixels constituting an image. In the measurement process, the measurement processing unit 347 calculates 3D coordinates of each point on the surface of the subject by the principle of triangulation on the basis of the disparity distribution. 3D coordinates are calculated in each pixel of the plurality of pixels. The measurement processing unit 347 generates color 3D data. The color 3D data includes color information of each pixel of the first NR image and 3D coordinates corresponding to each pixel. The color information includes a red pixel value, a green pixel value, and a blue pixel value. In the color 3D data, the color information and the 3D coordinates are associated with each pixel. The color 3D data may include color information of each pixel of the second NR image and 3D coordinates corresponding to each pixel (step S220).

After step S220, the visualization processing unit 343 executes a visualization process. In the visualization process, the visualization processing unit 343 generates a perspective projection image by disposing the color 3D data within a virtual space. The perspective projection image is equivalent to an image generated when a virtual camera disposed within the virtual space has imaged a subject within the virtual space. The CPU 34 outputs the generated perspective projection image to the video processing unit 31. The video processing unit 31 outputs the perspective projection image to the display unit 5 (step S225).

After step S225, the display processing unit 341 causes the display unit 5 to display the perspective projection image generated in step S225. The display unit 5 displays the perspective projection image. The display processing unit 341 may cause the display unit 5 to display the perspective projection image instead of the first image or may cause the display unit 5 to simultaneously display the first image and the perspective projection image (step S230).

After step S230, the control unit 340 stores a success as a processing result (step S235). After step S235, the processing in step S160 is executed.

In step S205, the image processing unit 342 determines whether or not motion has been detected on the basis of at least one of the first value and the second value. The first value indicates motion in the plurality of first images. The second value indicates motion in the plurality of second images. When no motion has been detected, the image processing unit 342 executes the noise reduction process in step S215. When no motion has been detected, the measurement processing unit 347 executes the measurement process in step S220. When no motion has been detected, the visualization processing unit 343 executes the visualization process in step S225.

The suitability determination unit 345 may calculate only either one of the first value and the second value in the motion detection process. The suitability determination unit 345 may determine whether or not motion has been detected on the basis of only either one of the first value and the second value.

The imaging device 22 may generate a plurality of first images and one second image. In this case, the suitability determination unit 345 calculates the first value on the basis of the plurality of first images. The imaging device 22 may generate one first image and a plurality of second images. In this case, the suitability determination unit 345 calculates the second value on the basis of the plurality of second images.

The image processing unit 342 may be configured to process three or more image sets and select the most appropriate set for image processing. Even if motion is detected between two images of two consecutive sets, there is a possibility that motion will not be detected between two images of other two consecutive sets. Thus, a probability of redoing of imaging is lowered by selecting an object to be processed from the three or more image sets. The noise reduction unit 346 can further reduce noise by executing the noise reduction process on the basis of three or more images.

The suitability determination unit 345 is optional. Therefore, the motion detection processing in step S200 may not be executed. The determination in step S205 may not be executed.

The noise reduction unit 346 is optional. Therefore, the noise reduction process in step S215 may not be executed. In this case, the measurement processing unit 347 executes a measurement process using one image set. The measurement processing unit 347 calculates 3D coordinates of a plurality of points on the surface of the subject using the passive stereo method on the basis of the first image corresponding to the first optical image and the second image corresponding to the second optical image.

One image set may be selected from a plurality of image sets and the measurement processing unit 347 may execute the measurement process using the selected image set. For example, the selected image set includes two images having smaller values indicating motion. The selected image set may include two images having higher contrast.

The visualization processing unit 343 is optional. Therefore, the visualization process in step S225 may not be executed.

The display unit 5 may display a value indicating whether or not the image is suitable for image processing, i.e., a result of calculating a value indicating motion. When the image is not suitable for image processing, i.e., only when motion has been detected, the display unit 5 may display the result of calculating the value indicating motion. For example, the calculation result is a message corresponding to a value indicating motion. For example, the message indicates that motion has been detected. When motion has been detected, the endoscope device 1 can notify the user of a warning.

The display of the image in the measurement mode is optional. Therefore, the first image may not be displayed in steps S110 and S135. The perspective projection image may not be displayed in step S230.

The processes to be executed by the image processing unit 342, the visualization processing unit 343, and the display processing unit 341 may be executed outside the endoscope device 1. That is, the above process may be executed by an external computer system such as a PC or a network server connected to the endoscope device 1 in a wireless or wired manner.

The first embodiment of the present invention is compared with a reference form of the present invention with reference to FIG. 26. The endoscope device 1 does not need to execute an operation in the reference form. Hereinafter, the operation of the endoscope device 1 in the reference form will be described for comparison between the first embodiment and the reference form.

A timing chart TC100 shown in FIG. 26 shows the operation of the imaging device 22. Descriptions of parts that are the same as those shown in FIG. 7 will be omitted. The white light source 37 is continuously turned on.

Before the reading period of the cells 54 of the first row during the frame period (i−1) is started, the imaging optical path is the second optical path L2. When the exposure period of the cells 54 of the first row during the frame period (i−1) has ended, the reading period of the cells 54 of the first row during the frame period (i−1) is started. At this moment, switching of the imaging optical path is started. The switching unit 25 starts switching from the second optical path L2 to the first optical path L1.

When the reading period of the cells 54 of the first row during the frame period (i−1) has ended, the switching unit 25 completes switching from the second optical path L2 to the first optical path L1. The imaging optical path is the first optical path L1.

When the exposure period of the cells 54 of the first row during the frame period (i+1) has ended, the reading period of the cells 54 of the first row during the frame period (i+1) is started. At this moment, switching of the imaging optical path is started. The switching unit 25 starts switching from the first optical path L1 to the second optical path L2.

When the reading period of the cells 54 of the first row during the frame period (i+1) has ended, the switching unit 25 completes switching from the first optical path L1 to the second optical path L2. The imaging optical path is the second optical path L2.

When the exposure period of the cells 54 of the first row during the frame period (i+3) has ended, the reading period of the cells 54 of the first row during the frame period (i+3) is started. At this moment, switching of the imaging optical path is started. The switching unit 25 starts switching from the second optical path L2 to the first optical path L1.

When the reading period of the cells 54 of the first row during the frame period (i+3) has ended, the switching unit 25 completes the switching from the second optical path L2 to the first optical path L1. The imaging optical path is the first optical path L1.

In FIG. 26, an image (an output image) output from the imaging device 22 is schematically shown. An image IMG100 includes pixel signals read from cells 54 of eight rows during a reading period in the frame period (i−1). Switching from the second optical path L2 to the first optical path L1 is executed during an exposure period in the frame period (i−1). The image IMG100 includes pixel signals based on the first optical image and pixel signals based on the second optical image. Therefore, the image IMG100 is not suitable for measurement.

The image IMG101 includes pixel signals read from the cells 54 of the eight rows during a reading period in a frame period i. Switching of the imaging optical path is not executed during the exposure period in the frame period i. The image IMG101 includes pixel signals based on the first optical image.

An image IMG102 includes pixel signals read from the cells 54 of the eight rows during the reading period in the frame period (i+1). Switching from the first optical path L1 to the second optical path L2 is executed during the exposure period in the frame period (i+1). The image IMG102 includes pixel signals based on the first optical image and pixel signals based on the second optical image. Therefore, the image IMG102 is not suitable for measurement.

An image IMG103 includes pixel signals read from the cells 54 of the eight rows during the reading period in the frame period (i+2). Switching of the imaging optical path is not executed during the exposure period in the frame period (i+2). The image IMG103 includes pixel signals based on the second optical image.

The measurement processing unit 347 executes a measurement process on the basis of the image IMG101 and the image IMG103. An interval between a first acquisition timing and a second acquisition timing is the same as a period of two frames. The first acquisition timing is a timing at which the imaging device 22 acquires the image IMG101. The second acquisition timing is a timing at which the imaging device 22 acquires the image IMG103.

In the timing chart TC100 shown in FIG. 26, an interval at which two images for measurement are acquired is the same as a period of two frames. On the other hand, in the timing chart TC10 shown in FIG. 7, an interval at which two images for measurement are acquired is the same as a period of one frame. In the timing chart TC10 shown in FIG. 7, compared with the timing chart TC100 shown in FIG. 26, an interval at which two images for measurement are acquired is short.

A method of operating an endoscope device according to each aspect of the present invention includes a first step, a second step, and a third step. In the first step (S130 and S145), the illumination control unit 33 causes the white light source 37 to generate illumination light during the second period. In the second step (S130 and S145), the illumination control unit 33 causes the white light source 37 to stop the generation of the illumination light during the third period. In the third step (S132 and S147), the switching control unit 36 causes the switching unit 25 to start switching of the imaging condition during the third period and complete the switching of the imaging condition during the third period. The switching control unit 36 causes the switching unit 25 to complete switching of the imaging condition before the next second period is started. That is, the switching control unit 36 causes the switching unit 25 to complete the switching of the imaging condition during the third period which is the same as the third period during which switching of the imaging conditions has been started.

The endoscope device 1 can shorten a time interval of imaging under a plurality of imaging conditions. Thus, a time interval at which a plurality of images for image processing are acquired is shortened. Motions between a plurality of images used for image processing are reduced and deterioration in the quality of an image processing result due to an influence of motion is reduced. Furthermore, because the endoscope device 1 performs global exposure, deterioration in the quality of the image processing result due to an influence of rolling distortion is reduced. That is, the quality of the image processing result is improved. Thus, measurement accuracy is improved in the measurement process.

When an image with motion is used for the measurement process, measurement accuracy deteriorates. Only when the motion has not been detected, the measurement processing unit 347 executes the measurement process. Therefore, measurement accuracy is improved.

When an image with motion has been used for the visualization process, the quality of the result obtained by the reconstruction of a 3D shape of a subject deteriorates. Only when no motion has been detected, the visualization processing unit 343 executes the visualization process. Thus, the quality of the result obtained by the reconstruction of the 3D shape of the subject is improved.

The noise reduction unit 346 executes the noise reduction process using a plurality of image sets. Thereby, the accuracy of template matching process is improved. Thus, the measurement accuracy is improved and the quality of the result obtained by the reconstruction of the 3D shape of the subject is improved.

Second Embodiment

A second embodiment of the present invention will be described using the endoscope device 1 shown in FIG. 2. The imaging device 22 captures an image at high speed (in a shorter frame period). When imaging is performed at high speed, some of the cells 54 are not properly exposed. In the image, the quality of the region corresponding to the cell 54 which is not properly exposed deteriorates. In the second embodiment, the quality of the image that is displayed is maintained by limiting a range of the image that is displayed on the display unit 5.

Figure 11:
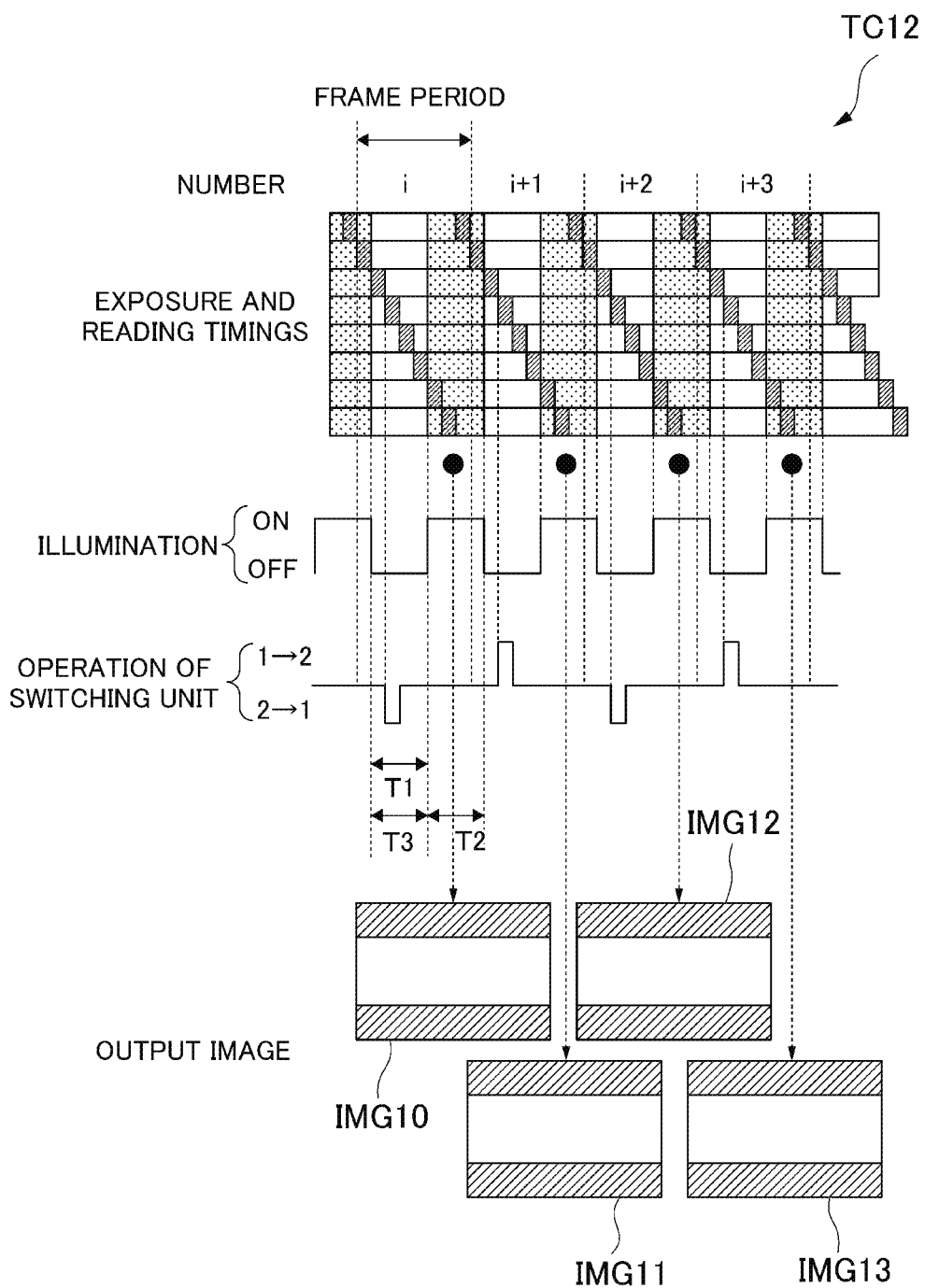
FIG. 11 is a timing chart showing an operation of an imaging device according to a second embodiment of the present invention.

FIG. 11 shows relationships between an operation of the imaging device 22 in a measurement mode, a state of illumination, and a state of an imaging condition. The operation of the imaging device 22 will be described with reference to FIG. 11. Descriptions of parts that are the same as those shown in FIG. 7 will be omitted.

A timing chart TC12 shows an operation of the imaging device 22. In the timing chart TC12, a frame rate is 120 fps. A length of each frame period is 1/120 sec. A time period during which the imaging device 22 reads pixel signals from cells 54 of one row is a time period Tr. The time period Tr is represented by the following Eq. (2). A number m is an integer of 2 or more. An exposure period of cells 54 of m rows overlaps a second period during which the white light source 37 is continuously turned on.

$$Tr=1/(120 \times m) \qquad (2)$$

Reading periods of cells 54 of first to eighth rows during a frame period (i−1) are sequentially started and pixel signals of the cells 54 of the first to eighth rows are sequentially read. The cells 54 of the first to eighth rows are sequentially reset and exposure periods of the cells 54 of the first to eighth rows during a frame period i are sequentially started.

When the reading period of the cells 54 of the first row during the frame period (i−1) has ended, the white light source 37 is already turned on. When the reading period of the cells 54 of the first row during the frame period (i−1) has ended, an imaging optical path is a second optical path L2.

When the reading period of the cells 54 of the second row during the frame period (i−1) has ended, the white light source 37 is turned off.

When the reading period of the cells 54 of the fourth row during the frame period (i−1) has been started, switching of the imaging optical path is started. The switching unit 25 starts switching from the second optical path L2 to a first optical path L1.

When the reading period of the cells 54 of the fourth row during the frame period (i−1) has ended, the switching unit 25 completes switching from the second optical path L2 to the first optical path L1. The imaging optical path is the first optical path L1.

When the reading period of the cells 54 of the sixth row during the frame period (i−1) has ended, the white light source 37 is turned on.

When the reading period of the cells 54 of the eighth row during the frame period (i−1) has ended, the reading period of the cells 54 of the first row during the frame period i is started. The reading periods of the cells 54 of the first to eighth rows during the frame period i are sequentially started and the pixel signals of the cells 54 of the first to eighth rows are sequentially read. The cells 54 of the first to eighth rows are sequentially reset and the exposure periods of the cells 54 of the first to eighth rows during a frame period (i+1) are sequentially started.

When the reading period of the cells 54 of the second row during the frame period i has ended, the white light source 37 is turned off.

When the reading period of the cells 54 of the fourth row during the frame period i has been started, switching of the imaging optical path is started. The switching unit 25 starts switching from the first optical path L1 to the second optical path L2.

When the reading period of the cells 54 of the fourth row during the frame period i has ended, the switching unit 25 completes the switching from the first optical path L1 to the second optical path L2. The imaging optical path is the second optical path L2.

Thereafter, the white light source 37 is periodically turned on. The switching unit 25 periodically switches the imaging optical path.

In the timing chart TC12, during the second period T2, cells 54 of simultaneous exposure rows which are some rows consecutively disposed among a plurality of rows in an array of the plurality of cells 54 are simultaneously exposed. A period during which the cells 54 are exposed by turning on the white light source 37 is common to the cells 54 of the simultaneous exposure rows. The cells 54 of the third to sixth rows which are the simultaneous exposure rows are simultaneously exposed. The second period T2 is common to the cells 54 of the third to sixth rows. The second period T2 does not include the reading periods of the cells 54 of the third to sixth rows.

The second period T2 includes reading periods of the cells 54 of the first row and the second row of a certain frame period and the seventh row and the eighth row of a frame period previous to the certain frame period. A period during which the cells 54 of these rows are exposed by turning on the white light source 37 is shorter than exposure time periods of the cells 54 of the third to sixth rows. Alternatively, both the first optical image and the second optical image are exposed. Accordingly, the cells 54 of the first row, the second row, the seventh row, and the eighth row are not properly exposed.

The simultaneous exposure rows are consecutively disposed in half the plurality of rows in the array of the plurality of cells 54. The simultaneous exposure rows include cells 54 to be simultaneously exposed by turning on the white light source 37. In an upper quarter of the plurality of rows and a lower quarter of the plurality of rows, the cells 54 are not properly exposed.

An image IMG10 includes pixel signals read during the reading period in the frame period (i−1). An image IMG11 includes pixel signals read during the reading period in the frame period i. An image IMG12 includes pixel signals read during the reading period in the frame period (i+1). An image IMG13 includes pixel signals read during the reading period in the frame period (i+2).

The image IMG10 and the image IMG12 are generated on the basis of the second optical image. The image IMG11 and the image IMG13 are generated on the basis of the first optical image. Central regions of the image IMG10, the image IMG11, the image IMG12, and the image IMG13 include pixel signals read from the simultaneously exposed cells 54. Regions of upper quarters of the image IMG10, the image IMG11, the image IMG12, and the image IMG13 include pixel signals read from the cells 54 which are not sufficiently exposed. Regions of lower quarters of the image IMG10, the image IMG11, the image IMG12, and the image IMG13 include pixel signals read from the cells 54 which are not sufficiently exposed. Alternatively, the regions of the upper and lower quarters of the image IMG10, the image IMG11, the image IMG12, and the image IMG13 include pixel signals read from the pixels 54 exposed on the basis of both the first optical image and the second optical image.

The video processing unit 31 executes electronic mask processing. In the electronic mask processing, the video processing unit 31 executes a process of preventing an image of a region corresponding to rows other than the simultaneous exposure rows from being displayed. For example, the video processing unit 31 superimposes a black graphic in the region corresponding to the rows other than the simultaneous exposure rows in the image. In the image displayed by the display unit 5, the region corresponding to the rows other than the simultaneous exposure rows is black.

The video processing unit 31 may replace pixel values of the region corresponding to the rows other than the simultaneous exposure rows in the image with the black value. Also in this case, in the image displayed by the display unit 5, the region corresponding to the rows other than the simultaneous exposure rows is black.

The video processing unit 31 may clip only the image of the region corresponding to the row other than the simultaneous exposure rows from the images corresponding to the plurality of rows. In this case, the image displayed by the display unit 5 includes only the image of the region corresponding to the simultaneous exposure rows.

The simultaneous exposure rows may be changed in accordance with an indication from the user. For example, the user inputs an indication indicating a position of the simultaneous exposure rows by operating the operation unit 4. The imaging control unit 30 sets the simultaneous exposure rows in the imaging device 22 on the basis of the positions indicated by the user.

When the simultaneous exposure rows are changed, the first period T1 is changed. By changing the first period T1, the second period T2 and the third period T3 are changed. The imaging optical paths are switched within the third period T3. When the third period T3 is changed, a timing at which the imaging optical paths are switched may be changed in some cases.

In the image, a region corresponding to the cells 54 which are not sufficiently exposed is not displayed. Therefore, the quality of the image displayed by the display unit 5 is maintained.

In the image, the range in which the pixel signals based on the optical image of the subject are included is narrowed. Because the frame period becomes short, the endoscope device 1 can shorten a time interval of imaging under a plurality of imaging conditions more than in the first embodiment. As a result, the quality of an image processing result in a scene in which there is motion of the camera is improved as compared with the first embodiment.

Third Embodiment

Figure 12:
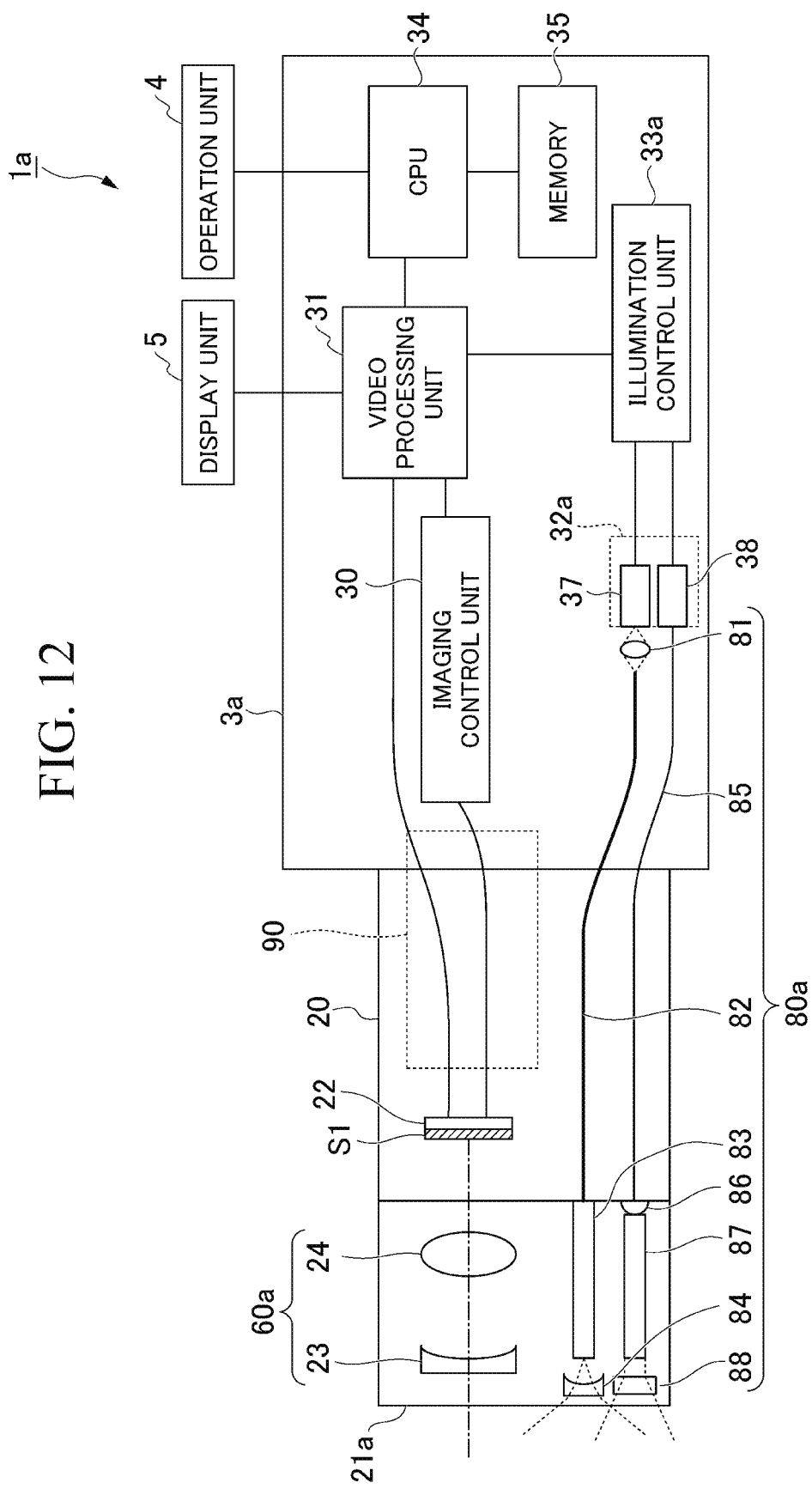
FIG. 12 is a block diagram showing a detailed configuration of an endoscope device according to a third embodiment of the present invention.

FIG. 12 shows a configuration of an endoscope device 1a according to a third embodiment of the present invention. Descriptions of parts that are the same as those shown in FIG. 2 will be omitted.

The main body unit 3 shown in FIG. 2 is changed to a main body unit 3a. The main body unit 3a does not have the switching control unit 36. In the main body unit 3a, the light source unit 32 shown in FIG. 2 is changed to a light source unit 32a. The light source unit 32a has a white light source 37 and a laser diode (LD) 38. In the main body unit 3a, the illumination control unit 33 shown in FIG. 2 is changed to an illumination control unit 33a.

The optical adapter 21 shown in FIG. 2 is changed to an optical adapter 21a. In the optical adapter 21a, the observation optical system 60 shown in FIG. 2 is changed to an observation optical system 60a. The observation optical system 60a includes a concave lens 23 and a convex lens 24.

The illumination optical system 80 shown in FIG. 2 is changed to an illumination optical system 80a. The optical adapter 21a has a part of the illumination optical system 80a. The illumination optical system 80a includes a condenser lens 81, a light guide 82, a rod lens 83, a diffusion lens 84, a fiber 85, a collimator lens 86, a rod lens 87, and a diffractive optical element 88. The condenser lens 81 is disposed in the main body unit 3a. The light guide 82 and the fiber 85 are disposed in the main body unit 3a and the insertion unit 20. The rod lens 83, the diffusion lens 84, the collimator lens 86, the rod lens 87, and the diffractive optical element 88 are disposed in the optical adapter 21a.

The outline of parts different from those of FIG. 2 will be described. The endoscope device 1a has the white light source 37 (a first light source) and the LD 38 (a second light source) as light sources. The illumination light includes first illumination light and second illumination light. The white light source 37 generates white light as the first illumination light. The LD 38 generates the second illumination light. The illumination optical system 80a has a diffractive optical element 88 (a pattern generation unit). The diffractive optical element 88 (the pattern generation unit) gives a spatial pattern including a bright part and a dark part to the second illumination light. The illumination optical system 80a radiates the second illumination light to which the pattern is given to the subject.

The plurality of imaging conditions include a first imaging condition and a second imaging condition. Under the first imaging condition, the first illumination light is radiated to the subject and the irradiation of the second illumination light to the subject is stopped. Under the second imaging condition, the second illumination light is radiated to the subject and the radiation of the first illumination light to the subject is stopped. The imaging device 22 generates a first image of the subject by imaging the subject under the first imaging condition. The imaging device 22 generates a second image of the subject by imaging the subject under the second imaging condition.

The measurement processing unit 347 calculates 3D coordinates of a plurality of points on the surface of the subject using an active stereo method on the basis of the second image. The imaging device 22 has a red color filter, a green color filter, and a blue color filter. The imaging device 22 generates a color image as the first image. The color image includes a plurality of pixels. Each pixel has information indicating each of brightness of red, brightness of green, and brightness of blue as a pixel value. The image processing unit 342 generates 3D shape data in which the 3D coordinates of the plurality of points are associated with pixel values of the plurality of points. The visualization processing unit 343 generates graphic data in which the 3D shape data is visualized.

The imaging device 22 generates a plurality of at least one of first images of the subject and second images of the subject. The suitability determination unit 345 of the CPU 34 calculates at least one of a value indicating whether or not a plurality of first images are suitable for image processing and a value indicating whether or not a plurality of second images are suitable for image processing.

The imaging device 22 generates a plurality of second images by imaging the subject under the second imaging condition. The noise reduction unit 346 of the CPU 34 generates a third image by executing a noise reduction process on the plurality of second images. The noise reduction unit 346 calculates 3D coordinates of a plurality of points on the surface of the subject on the basis of the third image.

Details of parts different from those of FIG. 2 will be described. The LD 38 generates blue laser light as second illumination light. The LD 38 may be disposed in the optical adapter 21*a*. The fiber 85 is a single mode fiber. The fiber 85 is connected to the LD 38. The laser light emitted from the LD 38 is transmitted to the tip of the insertion unit 20 via the fiber 85. The laser light emitted from the fiber 85 is incident on the rod lens 87 as parallel light via the collimator lens 86. The laser light is transmitted by the rod lens 87. The laser light emitted from the rod lens 87 is incident on the diffractive optical element 88. The laser light emitted from the rod lens 87 is parallel light having a uniform phase. The diffractive optical element 88 converts the parallel light into pattern light (the second illumination light) having a random spatial pattern due to an effect of interference. In the pattern light, the bright part and the dark part are spatially randomly disposed. The pattern light emitted from the diffractive optical element 88 is radiated to the subject.

The observation optical system 60*a* is a monocular optical system. The observation optical system 60*a* takes in light reflected on the surface of the subject illuminated with white light or pattern light. The concave lens 23 and the convex lens 24 form an optical image based on the light from the subject in an imaging region S1 of the imaging device 22.

The illumination control unit 33*a* controls the white light source 37 and the LD 38. The illumination control unit 33*a* causes the white light source 37 and the LD 38 to generate illumination light during a second period. The illumination control unit 33*a* causes the white light source 37 and the LD 38 to stop the generation of the illumination light during a third period. The illumination control unit 33*a* functions as a switching unit and a switching control unit. The illumination control unit 33*a* starts switching of the imaging condition during the third period and completes the switching of the imaging condition during the third period.

The illumination control unit 33*a* sets a first imaging condition during a plurality of first frame periods. The illumination control unit 33*a* sets a second imaging condition during a plurality of second frame periods. Each second frame period of the plurality of second frame periods is different from each first frame period of the plurality of first frame periods.

Under the first imaging condition, the illumination control unit 33*a* causes the white light source 37 to be turned on and causes the LD 38 to be turned off. Therefore, the illumination optical system 80*a* radiates the white light to the subject under the first imaging condition. The illumination optical system 80*a* does not radiate the pattern light to the subject under the first imaging condition. Under the first imaging condition, the observation optical system 60*a* takes in light reflected on the surface of the subject illuminated with white light.

Under the second imaging condition, the illumination control unit 33*a* causes the LD 38 to be turned on and causes the white light source 37 to be turned off. Therefore, the illumination optical system 80*a* radiates the pattern light to the subject under the second imaging condition. The illumination optical system 80*a* does not radiate white light to the subject under the second imaging condition. Under the second imaging condition, the observation optical system 60*a* takes in the light reflected on the surface of the subject illuminated with the pattern light.

Figure 13:
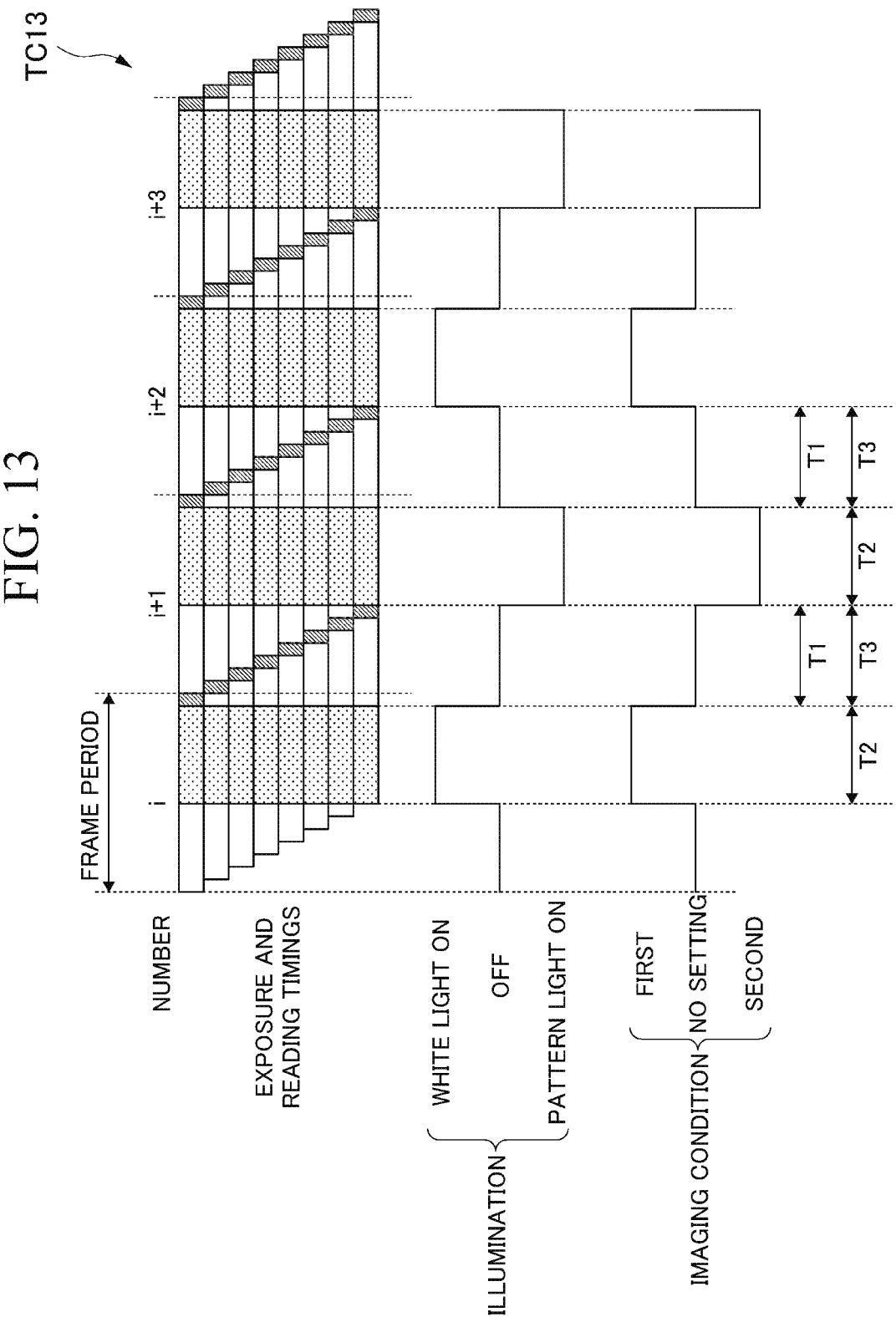
FIG. 13 is a timing chart showing an operation of an imaging device according to the third embodiment of the present invention.

FIG. 13 shows relationships between an operation of the imaging device 22 in a measurement mode, a state of illumination, and a state of an imaging condition. The operation of the imaging device 22 will be described with reference to FIG. 13. Descriptions of parts that are the same as those shown in FIG. 7 will be omitted.

A timing chart TC13 shows the operation of the imaging device 22. Cells 54 of first to eighth rows are sequentially reset and exposure periods of the cells 54 of the first to eighth rows during the frame period i are sequentially started.

When the exposure period of the cells 54 of the first row during the frame period i has been started, the white light source 37 and the LD 38 are already turned off. When the exposure period of the cells 54 of the first row during the frame period i has been started, no imaging condition is set.

When the exposure period of the cells 54 of the eighth row during the frame period i has been started, the turning-on of the white light source 37 is started. The illumination control unit 33*a* causes the white light source 37 to be turned on by outputting a turning-on control signal to the white light source 37. Thereby, the illumination control unit 33*a* sets the imaging condition to the first imaging condition. The white light source 37 starts turning-on on the basis of the control signal from the illumination control unit 33*a*.

When the reading period of the cells 54 of the first row during the frame period i has been started, the turning-on of the white light source 37 ends. The illumination control unit 33*a* causes the white light source 37 to be turned off by outputting a turning-off control signal to the white light source 37. The white light source 37 is turned off on the basis of the control signal from the illumination control unit 33*a*. Thereby, the illumination control unit 33*a* starts switching from the first imaging condition to the second imaging condition.

When the reading period of the cells 54 of the eighth row during the frame period i has ended, the turning-on of the LD 38 is started. The illumination control unit 33*a* causes the LD 38 to be turned on by outputting a turning-on control signal to the LD 38. Thereby, the illumination control unit 33*a* completes the switching from the first imaging condition to the second imaging condition. The LD 38 starts turning-on on the basis of the control signal from the illumination control unit 33*a*.

When the reading period of the cells 54 of the first row during the frame period (i+1) has been started, the turning-on of the LD 38 ends. The illumination control unit 33*a* causes the LD 38 to be turned off by outputting a turning-off control signal to the LD 38. The LD 38 is turned off on the basis of the control signal from the illumination control unit 33*a*. Thereby, the illumination control unit 33*a* starts switching from the second imaging condition to the first imaging condition.

When the reading period of the cells 54 of the eighth row during the frame period (i+1) has ended, the turning-on of the white light source 37 is started. The illumination control unit 33*a* causes the white light source 37 to be turned on by outputting a turning-on control signal to the white light source 37. Thereby, the illumination control unit 33*a* completes the switching from the second imaging condition to the first imaging condition. The white light source 37 starts turning-on on the basis of the control signal from the illumination control unit 33*a*.

The white light source 37 is turned on during the simultaneous exposure period in each of a frame period i and a frame period (i+2). The LD 38 is turned on during the simultaneous exposure period in each of a frame period (i+1) and a frame period (i+3). The white light source 37 and the LD 38 are iteratively turned on and off. The white light source 37 and the LD 38 are alternately turned on.

The illumination control unit 33a iterates switching from the first imaging condition to the second imaging condition and switching from the second imaging condition to the first imaging condition. The illumination control unit 33a executes switching of the imaging condition for each frame period. Alternatively, the illumination control unit 33a may switch the imaging condition to the second imaging condition every n frame periods.

During a first period T1, the imaging device 22 sequentially reads pixel signals from at least some of the plurality of cells 54 row by row. In a timing chart TC13 shown in FIG. 13, the first period T1 is a period from the start of the reading of the pixel signals in the cells 54 of the first row to the completion of the reading of the pixel signals in the cells 54 of the eighth row.

The white light source 37 or the LD 38 is turned on simultaneously with the completion of reading of the pixel signals during one frame period. That is, the white light source 37 or the LD 38 is turned on simultaneously with the completion of the first period T1. The white light source 37 or the LD 38 is turned off simultaneously with the start of the reading of the pixel signals during one frame period. That is, the white light source 37 or the LD 38 is turned off simultaneously with the start of the first period T1.

The illumination control unit 33a causes the white light source 37 or the LD 38 to generate illumination light during the second period T2. The white light source 37 or LD 38 is continuously turned on during the second period T2. In the timing chart TC13 shown in FIG. 13, the second period T2 is at least a part of a period other than the first period T1. In the timing chart TC13 shown in FIG. 13, the second period T2 is all of the period other than the first period T1. A turning-on period of the white light source 37 may be different from a turning-on period of the LD 38.

The illumination control unit 33a causes the white light source 37 or the LD 38 to stop the generation of the illumination light during the third period T3. The white light source 37 or the LD 38 is continuously turned off during the third period T3. The third period T3 is all of a period other than the second period T2. In the timing chart TC13 shown in FIG. 13, the third period T3 is the same as the first period T1. The sum of the length of the third period T3 and the length of the second period T2 is the same as the length of the frame period.

The illumination control unit 33a starts switching of the imaging condition during the third period T3 and completes the switching of the imaging condition during the third period T3. When the third period T3 has been started, the illumination control unit 33a starts the switching of the imaging condition by causing the white light source 37 or the LD 38 to be turned off. When the third period T3 ends, the illumination control unit 33a completes the switching of the imaging condition by causing the white light source 37 or the LD 38 to be turned on. In the timing chart TC13 shown in FIG. 13, because the third period T3 is the same as the first period T1, the illumination control unit 33a starts the switching of the imaging condition during the first period T1 and completes the switching of the imaging condition during the first period T1.

Figure 14:
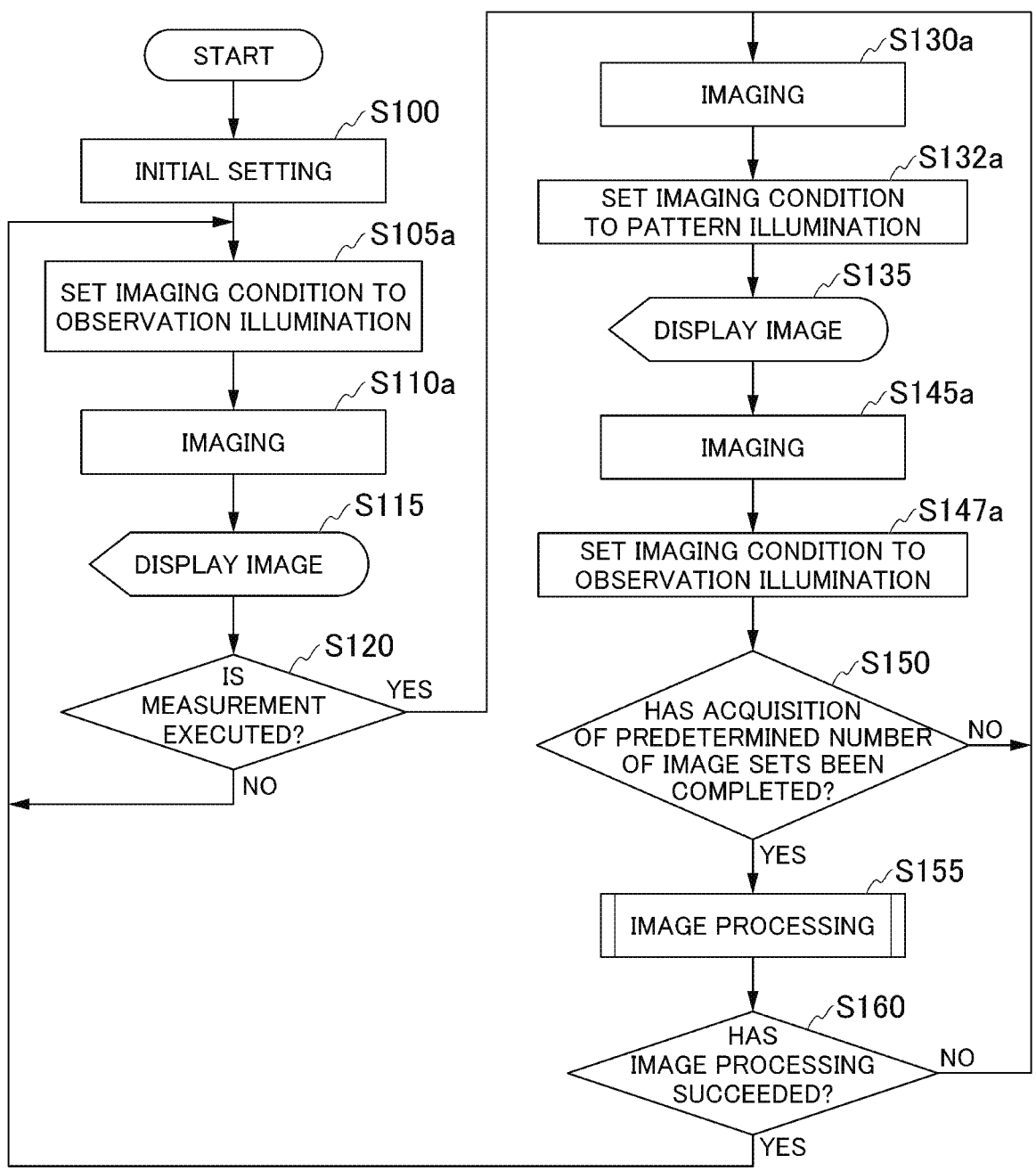
FIG. 14 is a flowchart showing a procedure of an operation of the endoscope device according to the third embodiment of the present invention.

FIG. 14 shows a procedure of the operation of the endoscope device 1a. The operation of the endoscope device 1a will be described with reference to FIG. 14. Descriptions of processing that is the same as that shown in FIG. 9 will be omitted.

After step S100, the illumination control unit 33a sets the imaging condition to observation illumination (a first imaging condition) by causing the white light source 37 to be turned on (step S105a).

After step S105a, the imaging device 22 generates an image of one frame and outputs the generated image. Because the imaging condition is the observation illumination, the imaging device 22 outputs a first image. When the third period is started, the illumination control unit 33a causes the white light source 37 to be turned off (step S110a).

When the control unit 340 has determined to execute the measurement in step S120, the imaging device 22 generates an image of one frame and outputs the generated image. Because the imaging condition is the observation illumination, the imaging device 22 outputs a first image. When the third period is started, the illumination control unit 33a causes the white light source 37 to be turned off (step S130a).

After step S130a, the illumination control unit 33a sets the imaging condition to pattern illumination (a second imaging condition) by causing the LD 38 to be turned on (step S132a). After step S132a, the processing in step S135 is executed.

After step S135, the imaging device 22 generates an image of one frame and outputs the generated image. Because the imaging condition is pattern illumination, the imaging device 22 outputs a second image. When the third period starts, the illumination control unit 33a causes the LD 38 to be turned off (step S145a).

After step S145a, the illumination control unit 33a sets the imaging condition to the observation illumination (the first imaging condition) by causing the white light source 37 to be turned on (step S147a). After step S147a, the processing in step S150 is executed.

When the control unit 340 determines that the acquisition of a predetermined number of image sets has not been completed in step S150, the processing in step S130a is executed. Until a predetermined number of image sets are acquired, the imaging condition is alternately and iteratively switched between the observation illumination and the pattern illumination. The imaging device 22 iteratively outputs the first image and the second image. Visibility deteriorates when the second image based on the pattern light is displayed. Thus, the display unit 5 sequentially updates and displays the first image without displaying the second image. The pattern of switching the imaging conditions is not limited to the above-described pattern. The imaging device 22 may acquire second images after the imaging device 22 acquires first images equal in number to a predetermined number of frames.

When the control unit 340 determines that the image processing has failed in step S160, the processing in step S130a is executed.

The processing shown in FIG. 10 is changed to the following process. An image set A and an image set B are input to the CPU 34. Each of the image set A and image set B includes one first image and one second image generated from two consecutive frame periods.

In the noise reduction process (step S215), the noise reduction unit 346 generates a second NR image (a third image) on the basis of the second image of the set A and the second image of the set B. A pixel value of the second NR image is an addition average of pixel values between the two second images.

In the measurement process (step S220), the measurement processing unit 347 generates a second corrected image by correcting optical distortion of the second NR image. The measurement processing unit 347 stores a reference pattern image. The reference pattern image is an image of a plane irradiated with the pattern light generated by the diffractive optical element 88. In the measurement process, the measurement processing unit 347 acquires a distribution of phase differences in a template matching process using the reference pattern image and the second NR image. The phase difference is a deviation amount of the pattern in the reference pattern image and the second NR image. The distribution of the phase differences includes phase difference information in each cell 54 of the plurality of cells 54. In the measurement process, the measurement processing unit 347 calculates 3D coordinates of each point on the surface of the subject by the principle of triangulation on the basis of the distribution of the phase differences. The measurement processing unit 347 generates color 3D data. The color 3D data includes color information of each pixel of the first image and 3D coordinates corresponding to each pixel.

The visualization processing unit 343 generates a perspective projection image in the visualization process (step S225). The CPU 34 outputs the generated perspective projection image to the video processing unit 31. The video processing unit 31 outputs the perspective projection image to the display unit 5.

The endoscope device 1a can shorten a time interval between the imaging of the subject illuminated with the white light and the imaging of the subject irradiated with the pattern light. Thus, the quality of the image processing result is improved. Measurement accuracy is improved in the measurement process. A deviation of color texture with respect to a reconstructed 3D shape of the subject decreases. Furthermore, because the endoscope device 1a performs global exposure, it is possible to reduce deterioration in the quality of the image processing result due to the influence of rolling distortion.

Second illumination light generated by the LD 38 may be laser light having a wavelength other than that of blue. For example, the wavelength of the second illumination light may be red, green, or infrared wavelength. Also, under the second imaging condition, radiation of first illumination light may not be stopped.

Fourth Embodiment

Figure 15:
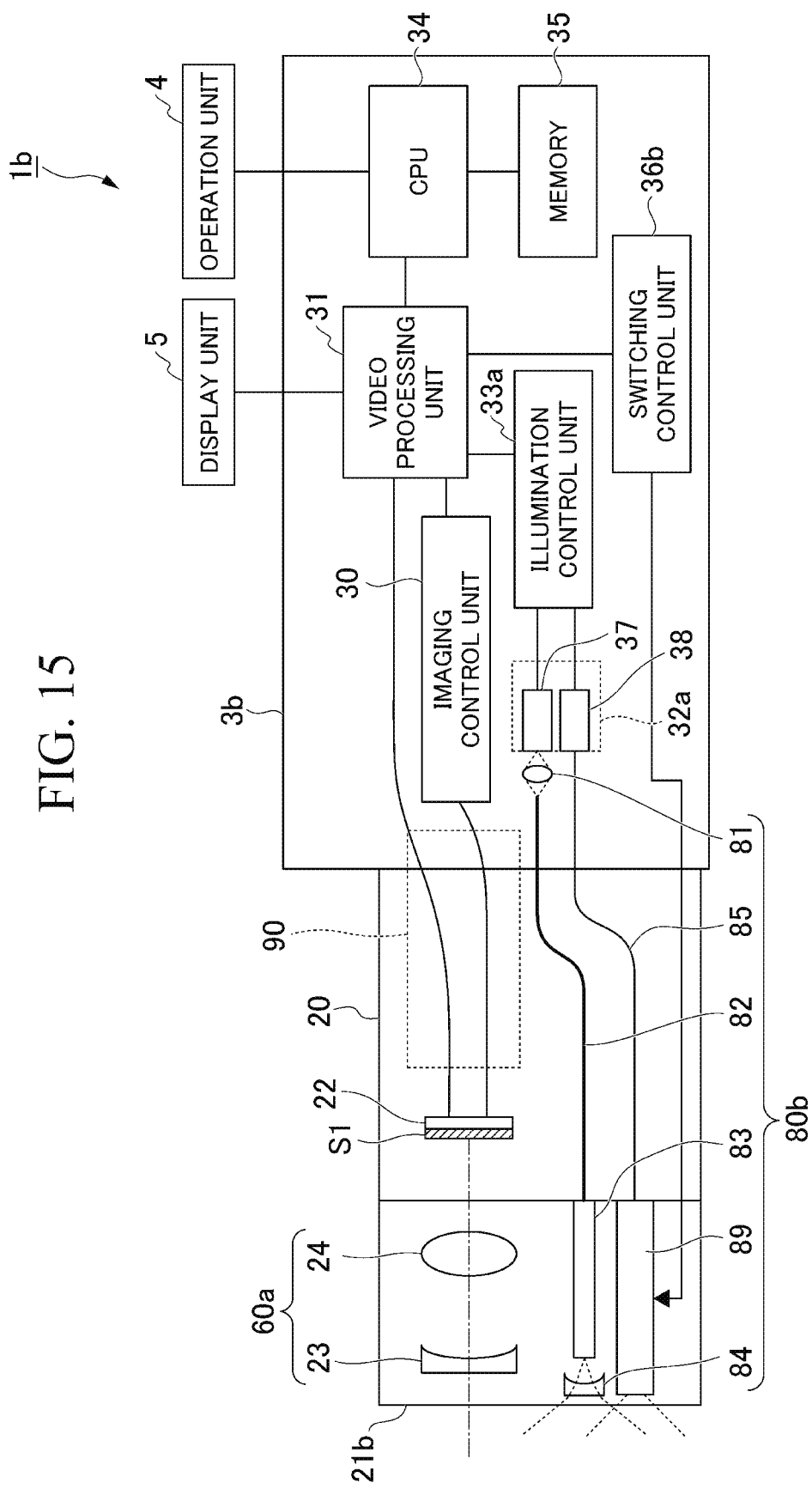
FIG. 15 is a block diagram showing a detailed configuration of an endoscope device according to a fourth embodiment of the present invention.

FIG. 15 shows a configuration of an endoscope device 1b according to a fourth embodiment of the present invention. Descriptions of parts that are the same as those shown in FIG. 12 will be omitted.

The main body unit 3a shown in FIG. 12 is changed to a main body unit 3b. The main body unit 3b includes a switching control unit 36b in addition to the configuration shown in FIG. 12.

The optical adapter 21a shown in FIG. 12 is changed to an optical adapter 21b. The illumination optical system 80a shown in FIG. 12 is changed to an illumination optical system 80b. The optical adapter 21b has a part of the illumination optical system 80b. The illumination optical system 80b includes a condenser lens 81, a light guide 82, a rod lens 83, a diffusion lens 84, a fiber 85, and a stripe generation unit 89 (a pattern generation unit). The condenser lens 81 is disposed in the main body unit 3b. The light guide 82 and the fiber 85 are disposed in the main body unit 3b and an insertion unit 20. The rod lens 83, the diffusion lens 84, and the stripe generation unit 89 are disposed in the optical adapter 21b.

Figure 16:
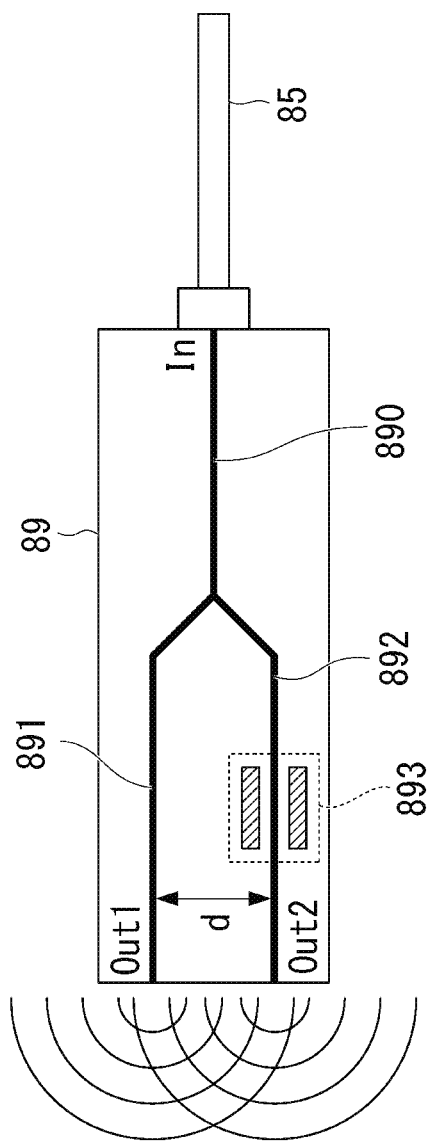
FIG. 16 is a block diagram showing a configuration of a stripe generation unit according to the fourth embodiment of the present invention.
Figure 16:
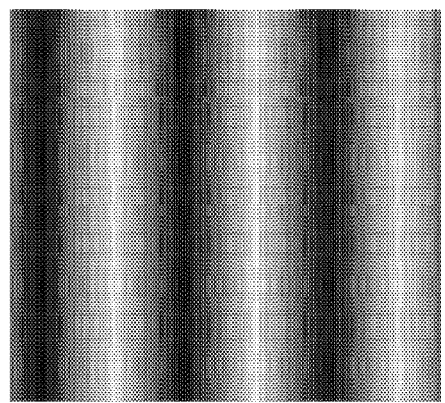

FIG. 16 shows a configuration of the stripe generation unit 89 (the pattern generation unit). The stripe generation unit 89 shown in FIG. 16 has a first optical path 890, a second optical path 891, a third optical path 892, and a phase shift unit 893 (a phase shifter).

The outline of parts different from those of FIG. 12 will be described. The stripe generation unit 89 gives a spatial pattern including a bright part and a dark part to illumination light. A plurality of imaging conditions further include a third imaging condition. The imaging device 22 generates a third image of a subject by imaging the subject under the third imaging condition. The phase shift unit 893 functions as a switching unit. The phase shift unit 893 performs switching between a first imaging condition, a second imaging condition, and the third imaging condition by shifting the phase of the pattern of the illumination light. A phase of a pattern under the first imaging condition, a phase of a pattern under the second imaging condition, and a phase of a pattern under the third imaging condition are different from one another. The measurement processing unit 347 of the CPU 34 calculates 3D coordinates of a plurality of points on the surface of the subject using the phase shift method on the basis of at least the first image, the second image, and the third image.

The endoscope device 1b includes a white light source 37 (a first light source) and an LD 38 (a second light source) as light sources. The illumination light includes first illumination light and second illumination light. The white light source 37 generates white light as the first illumination light. The LD 38 generates the second illumination light. The stripe generation unit 89 applies the pattern to the second illumination light. The plurality of imaging conditions further include a fourth imaging condition. Under the first imaging condition, the second imaging condition, and the third imaging condition, the second illumination light is radiated to the subject and radiation of the first illumination light to the subject is stopped. Under the fourth imaging condition, the first illumination light is radiated to the subject and radiation of the second illumination light to the subject is stopped. The imaging device generates a fourth image of the subject by imaging the subject under the fourth imaging condition. The imaging device 22 has a red color filter, a green color filter, and a blue color filter. The imaging device 22 generates a color image as the fourth image. The color image includes a plurality of pixels. Each pixel has information of each of brightness of red, brightness of green, and brightness of blue as pixel values. The measurement processing unit 347 generates 3D shape data in which 3D coordinates of a plurality of points are associated with pixel values of a plurality of points. The visualization processing unit 343 generates graphic data in which the 3D shape data is visualized.

The imaging device 22 generates a plurality of at least one of first images, a second images, third images, and fourth images. The suitability determination unit 345 determines at least one of a value indicating whether or not the plurality of first images are suitable for image processing, a value indicating whether or not the plurality of second images are suitable for image processing, a value indicating whether or not the plurality of third images are suitable for image processing, and a value indicating whether or not the plurality of fourth images are suitable for image processing.

The switching control unit 36b causes the phase shift unit 893 to set the first imaging condition during the plurality of first frame periods. The switching control unit 36b causes the phase shift unit 893 to set the second imaging condition during the plurality of second frame periods. Each second frame period of the plurality of second frame periods is different from each first frame period of the plurality of first frame periods. The switching control unit 36b causes the phase shift unit 893 to set the third imaging condition during the plurality of third frame periods. Each third frame period of the plurality of third frame periods is different from each first frame period of the plurality of first frame periods and is different from each second frame period of the plurality of second frame periods.

The noise reduction unit 346 generates a fifth image by performing a noise reduction process on the plurality of first images. The noise reduction unit 346 generates a sixth image by executing the noise reduction process on the plurality of second images. The noise reduction unit 346 generates a seventh image by executing a noise reduction process on a plurality of third images. The measurement processing unit 347 calculates 3D coordinates of a plurality of points on the surface of the subject on the basis of the fifth image, the sixth image, and the seventh image.

Details of parts different from those of FIG. 12 will be described. Laser light emitted from the LD 38 is transmitted to a tip of the insertion unit 20 via the fiber 85. The fiber 85 is connected to the stripe generation unit 89. The laser light (the second illumination light) emitted from the fiber 85 is incident on the stripe generation unit 89.

The laser light is incident on a first end In of the stripe generation unit 89. The first optical path 890 is connected to the first end In. The laser light incident on the first end In is transmitted through the first optical path 890. The first optical path 890 branches into a second optical path 891 and a third optical path 892. The second optical path 891 and the third optical path 892 are connected to the first optical path 890. The laser light transmitted through the first optical path 890 is split into first laser light and second laser light. The first laser light is incident to the second optical path 891. The second laser light is incident to the third optical path 892. The first laser light incident to the second optical path 891 is transmitted through the second optical path 891. The second laser light incident to the third optical path 892 is transmitted through the third optical path 892.

The second optical path 891 is connected to a second end Out1. The third optical path 892 is connected to a third end Out2. The length of the second optical path 891 is equal to that of the third optical path 892. The first laser light transmitted through the second optical path 891 is emitted from the second end Out1 and is radiated to the subject. The second laser light transmitted through the third optical path 892 is emitted from the third end Out2 and radiated to the subject.

The second end Out1 and the third end Out2 are separated from each other by a predetermined width d. The first laser light emitted from the second end Out1 and the second laser light emitted from the third end Out2 interfere with each other. One striped pattern is formed by the interference of laser light. The pattern can be approximately regarded to be a stripe pattern emitted from one light source. In the stripe pattern, an elongated bright part and an elongated dark part are alternately arranged.

A cycle of the stripe pattern is a cycle based on the principle of Young's interference stripes. The cycle is a cycle based on the wavelength of the laser light guided to the first end In and the width d. For example, when the wavelength of the laser light guided to the first end In becomes short in a state in which the width d is fixed, the cycle of the stripe pattern becomes short. When the wavelength of the laser light guided to the first end In becomes long in a state in which the width d is fixed, the cycle of the stripe pattern becomes long. When the width d is widened, i.e., when the second end Out1 and the third end Out2 are separated from each other, in a state in which a wavelength band of the laser light guided to the first end In is fixed, the cycle of the stripe pattern becomes short. When the width d is narrowed, i.e., when the second end Out1 and the third end Out2 are close to each other, in a state in which the wavelength band of the laser light guided to the first end In is fixed, the cycle of the stripe pattern becomes long.

A part of the third optical path 892 is disposed inside the phase shift unit 893. The switching control unit 36b disposed in the main body unit 3b supplies a current to the phase shift unit 893. The phase shift unit 893 generates heat on the basis of the current supplied from the switching control unit 36b. A refractive index of the third optical path 892 is changed by the generated heat and an optical path length of the third optical path 892 is changed. The phase shift unit 893 shifts the phase of the second laser light guided to the third optical path 892 on the basis of a change in a temperature. The phase of the first laser light and the phase of the second laser light are different from each other. The first laser light is emitted from the second end Out1 via the second optical path 891. The second laser light is emitted from the third end Out2 via the third optical path 892 having a temperature different from that of the second optical path 891. The phase of the stripe of the stripe pattern is changed by interference in a state in which the phase of the first laser light and the phase of the second laser light are shifted. That is, the phase of the stripes is shifted. A method in which the phase shift unit 893 shifts the phase of the laser light is not limited to a method using a change in a temperature.

The illumination control unit 33a controls the white light source 37 and the LD 38. The illumination control unit 33a causes the white light source 37 and the LD 38 to generate illumination light during the second period. The illumination control unit 33a causes the white light source 37 and the LD 38 to stop the generation of the illumination light during the third period. The illumination control unit 33a functions as a switching unit and a switching control unit. The illumination control unit 33a starts switching of the imaging condition during the third period and completes the switching of the imaging condition during the third period. The switching control unit 36b causes the phase shift unit 893 to start the switching of the imaging condition during the third period and complete the switching of the imaging condition during the third period.

Under the first imaging condition, the illumination control unit 33a causes the LD 38 to be turned on and causes the white light source 37 to be turned off. Therefore, the illumination optical system 80a radiates the pattern light to the subject under the first imaging condition. The illumination optical system 80a does not radiate white light to the subject under the first imaging condition. The switching control unit 36b causes the phase shift unit 893 to set the phase of the pattern light to a first phase. Under the first imaging condition, the observation optical system 60a takes in the light reflected on the surface of the subject illuminated with the pattern light.

Under the second imaging condition, the illumination control unit 33a causes the LD 38 to be turned on and causes the white light source 37 to be turned off. Therefore, the illumination optical system 80a radiates the pattern light to the subject under the second imaging condition. The illumination optical system 80a does not radiate white light to the subject under the second imaging condition. The switching control unit 36b causes the phase shift unit 893 to set the phase of the pattern light to the second phase. The second phase is different from the first phase. Under the second imaging condition, the observation optical system 60a takes in the light reflected on the surface of the subject illuminated with the pattern light.

Under the third imaging condition, the illumination control unit 33a causes the LD 38 to be turned on and causes the white light source 37 to be turned off. Therefore, the illumination optical system 80a radiates the pattern light to the subject under the third imaging condition. The illumination optical system 80a does not radiate white light to the subject under the third imaging condition. The switching control unit 36b causes the phase shift unit 893 to set the phase of the pattern light to the third phase. The third phase is different from the first phase and is different from the second phase. Under the third imaging condition, the observation optical system 60a takes in the light reflected on the surface of the subject illuminated with the pattern light.

The illumination control unit 33a causes the white light source 37 to be turned on and causes the LD 38 to be turned off under the fourth imaging condition. Therefore, the illumination optical system 80a radiates white light to the subject under the fourth imaging condition. The illumination optical system 80a does not radiate the pattern light to the subject under the fourth imaging condition. The observation optical system 60a takes in the light reflected on the surface of the subject illuminated with the white light under the fourth imaging condition.

Figure 17:
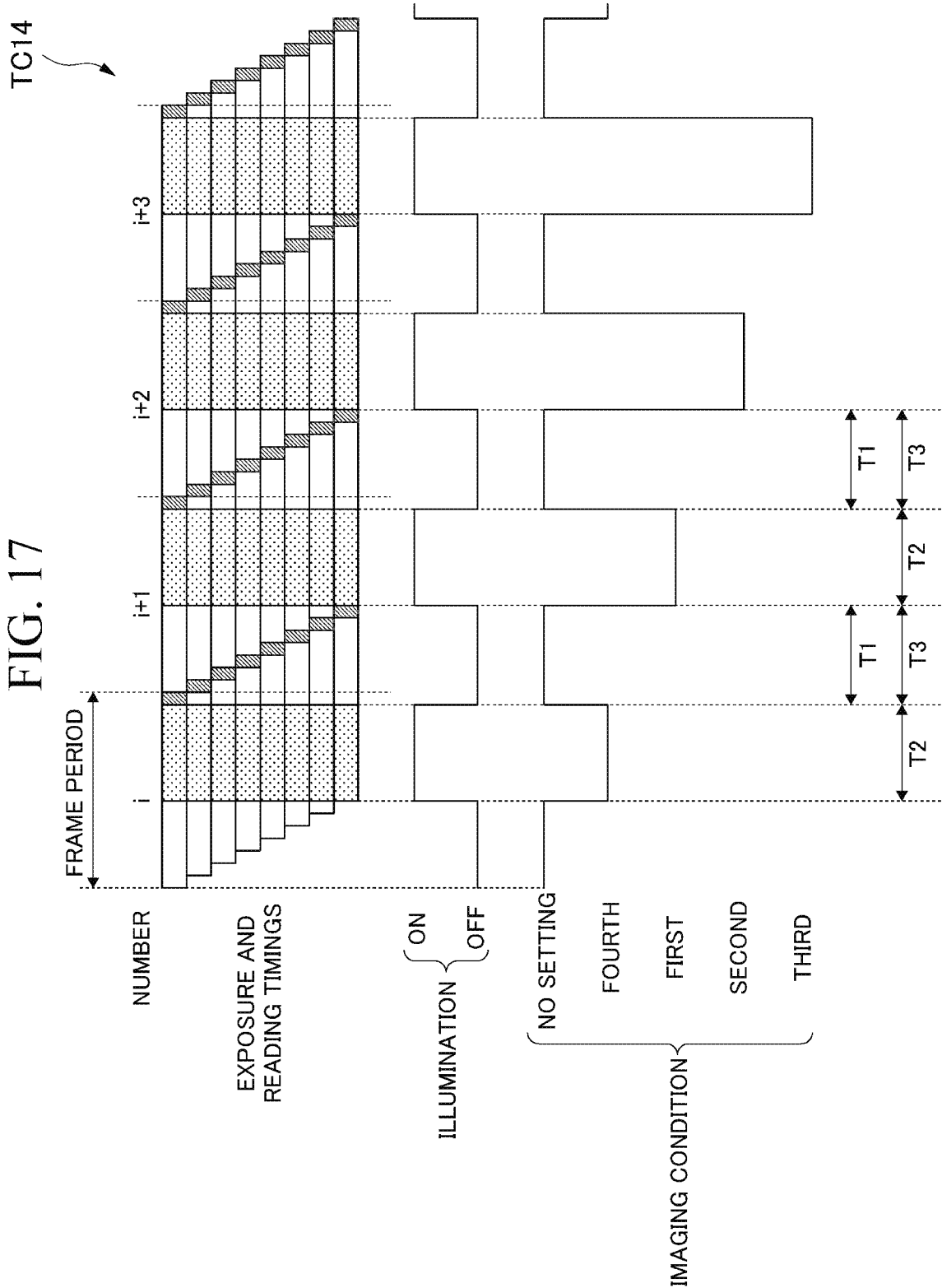
FIG. 17 is a timing chart showing an operation of an imaging device according to the fourth embodiment of the present invention.

FIG. 17 shows relationships between an operation of the imaging device 22 in a measurement mode, a state of illumination, and a state of an imaging condition. The operation of the imaging device 22 will be described with reference to FIG. 17. Descriptions of parts that are the same as those shown in FIG. 7 will be omitted.

A timing chart TC14 shows the operation of the imaging device 22. Cells 54 of first to eighth row are sequentially reset and exposure periods of the cells 54 of the first to eighth rows during a frame period i are sequentially started.

When the exposure period of the cells 54 of the first row during the frame period i has been started, the white light source 37 and the LD 38 are already turned off. When the exposure period of the cells 54 of the first row during the frame period i has been started, no imaging condition is set.

When the exposure period of the cells 54 of the eighth row during the frame period i has been started, the turning-on of the white light source 37 is started. The illumination control unit 33a causes the white light source 37 to be turned on by outputting a turning-on control signal to the white light source 37. Thereby, the illumination control unit 33a sets the imaging condition to the fourth imaging condition. The white light source 37 starts turning-on on the basis of the control signal from the illumination control unit 33a.

When the reading period of the cells 54 of the first row during the frame period i has been started, the turning-on of the white light source 37 ends. The illumination control unit 33a causes the white light source 37 to be turned off by outputting a turning-off control signal to the white light source 37. The white light source 37 is turned off on the basis of the control signal from the illumination control unit 33a. Thereby, the illumination control unit 33a starts switching from the fourth imaging condition to the first imaging condition.

When the reading period of the cells 54 of the eighth row during the frame period i has ended, the turning-on of the LD 38 is started. The illumination control unit 33a causes the LD 38 to be turned on by outputting a turning-on control signal to the LD 38. The LD 38 starts turning-on on the basis of the control signal from the illumination control unit 33a. The switching control unit 36b causes the phase of the pattern light to be set to the first phase by outputting an electric current to the phase shift unit 893. The phase shift unit 893 sets the phase of the pattern light to the first phase on the basis of the electric current from the switching control unit 36b. Thereby, the illumination control unit 33a and the switching control unit 36b complete switching from the fourth imaging condition to the first imaging condition.

When the reading period of the cells 54 of the first row during the frame period (i+1) has been started, the turning-on of the LD 38 ends. The illumination control unit 33a causes the LD 38 to be turned off by outputting a turning-off control signal to the LD 38. The LD 38 is turned off on the basis of the control signal from the illumination control unit 33a. Thereby, the illumination control unit 33a starts switching from the first imaging condition to the second imaging condition.

When the reading period of the cells 54 of the eighth row during the frame period (i+1) has ended, the turning-on of the LD 38 is started. The illumination control unit 33a causes the LD 38 to be turned on by outputting a turning-on control signal to the LD 38. The LD 38 starts turning-on on the basis of the control signal from the illumination control unit 33a. The switching control unit 36b causes the phase of the pattern light to be set to the second phase by outputting an electric current to the phase shift unit 893. The phase shift unit 893 sets the phase of the pattern light to the second phase on the basis of the electric current from the switching control unit 36b. Thereby, the illumination control unit 33a and the switching control unit 36b complete switching from the first imaging condition to the second imaging condition.

When the reading period of the cells 54 of the first row during the frame period (i+2) has been started, the turning-on of the LD 38 ends. The illumination control unit 33a causes the LD 38 to be turned off by outputting a turning-off control signal to the LD 38. The LD 38 is turned off on the basis of the control signal from the illumination control unit 33a. Thereby, the illumination control unit 33a starts switching from the second imaging condition to the third imaging condition.

When the reading period of the cells 54 of the eighth row during the frame period (i+2) has ended, the turning-on of the LD 38 is started. The illumination control unit 33a causes the LD 38 to be turned on by outputting a turning-on control signal to the LD 38. The LD 38 starts turning-on on the basis of the control signal from the illumination control unit 33a. The switching control unit 36b causes the phase of the pattern light to be set to the third phase by outputting an electric current to the phase shift unit 893. The phase shift unit 893 sets the phase of the pattern light to the third phase on the basis of the electric current from the switching control unit 36b. Thereby, the illumination control unit 33a and the switching control unit 36b complete switching from the second imaging condition to the third imaging condition.

When the reading period of the cells 54 of the first row during the frame period (i+3) has been started, the turning-on of the LD 38 ends. The illumination control unit 33a causes the LD 38 to be turned off by outputting a turning-off control signal to the LD 38. The LD 38 is turned off on the basis of the control signal from the illumination control unit 33a. Thereby, the illumination control unit 33a starts switching from the third imaging condition to the fourth imaging condition.

When the reading period of the cells 54 of the eighth row during the frame period (i+3) has ended, the turning-on of the white light source 37 is started. The illumination control unit 33a causes the white light source 37 to be turned on by outputting a turning-on control signal to the white light source 37. The white light source 37 starts turning-on on the basis of the control signal from the illumination control unit 33a. Thereby, the illumination control unit 33a completes switching from the third imaging condition to the fourth imaging condition.

The white light source 37 is turned on during the simultaneous exposure period in the frame period i. The LD 38 is turned on during the simultaneous exposure period in each of the frame period (i+1), the frame period (i+2), and the frame period (i+3). The white light source 37 and the LD 38 are iteratively turned on and off.

The illumination control unit 33a and the switching control unit 36b iterate switching from the fourth imaging condition to the first imaging condition, switching from the first imaging condition to the second imaging condition, switching from the second imaging condition to the third imaging condition, and switching from the third imaging condition to the fourth imaging condition. The illumination control unit 33a and the switching control unit 36b execute switching of the imaging condition during each frame period.

During the first period T1, the imaging device 22 sequentially reads pixel signals from at least some of the plurality of cells 54 row by row. In a timing chart TC14 shown in FIG. 17, the first period T1 is a period from the start of the reading of the pixel signals of the cells 54 of the first row to the completion of the reading of the pixel signals of the cells 54 of the eighth row.

The white light source 37 or the LD 38 is turned on simultaneously with the completion of reading of pixel signals during one frame period. That is, the white light source 37 or the LD 38 is turned on simultaneously with the completion of the first period T1. The white light source 37 or the LD 38 is turned off simultaneously with the start of the reading of the pixel signals during one frame period. That is, the white light source 37 or the LD 38 is turned off simultaneously with the start of the first period T1.

The illumination control unit 33a causes the white light source 37 or the LD 38 to generate the illumination light during the second period T2. The white light source 37 or the LD 38 is continuously turned on during the second period T2. The second period T2 is all of a period other than the first period T1. In the timing chart TC14 shown in FIG. 17, the sum of the length of the first period T1 and the length of the second period T2 is the same as the length of the frame period.

The illumination control unit 33a causes the white light source 37 or the LD 38 to stop the generation of the illumination light during the third period T3. The white light source 37 or the LD 38 is continuously turned off during the third period T3. The third period T3 is all of a period other than the second period T2. In the timing chart TC14 shown in FIG. 17, the third period T3 is the same as the first period T1.

The illumination control unit 33a and the phase shift unit 893 start the switching of the imaging condition during the third period T3 and complete the switching of the imaging condition during the third period T3. The illumination control unit 33a and the phase shift unit 893 complete the switching of the imaging condition before the next second period is started. That is, the illumination control unit 33a and the phase shift unit 893 complete the switching of the imaging condition during the third period that is the same as the third period during which the switching of the imaging condition has been started. When the third period T3 has been started, the illumination control unit 33a starts the switching of the imaging condition by causing the white light source 37 or the LD 38 to be turned off. When the third period T3 ends, the illumination control unit 33a completes the switching of the imaging condition by causing the white light source 37 or the LD 38 to be turned on. When the third period T3 ends, the phase shift unit 893 completes the switching of the imaging condition by changing the phase of the pattern light. Because the third period T3 is the same as the first period T1 in the timing chart TC14 shown in FIG. 17, the illumination control unit 33a and the phase shift unit 893 start the switching of the imaging condition during the first period T1 and complete the switching of the imaging condition during the first period T1.

After the reading period of the cells 54 of the first row during each frame period is started and before the reading period of the cells 54 of the eighth row during each frame period is completed, the phase shift unit 893 may switch the phase of the pattern light.

Figure 18:
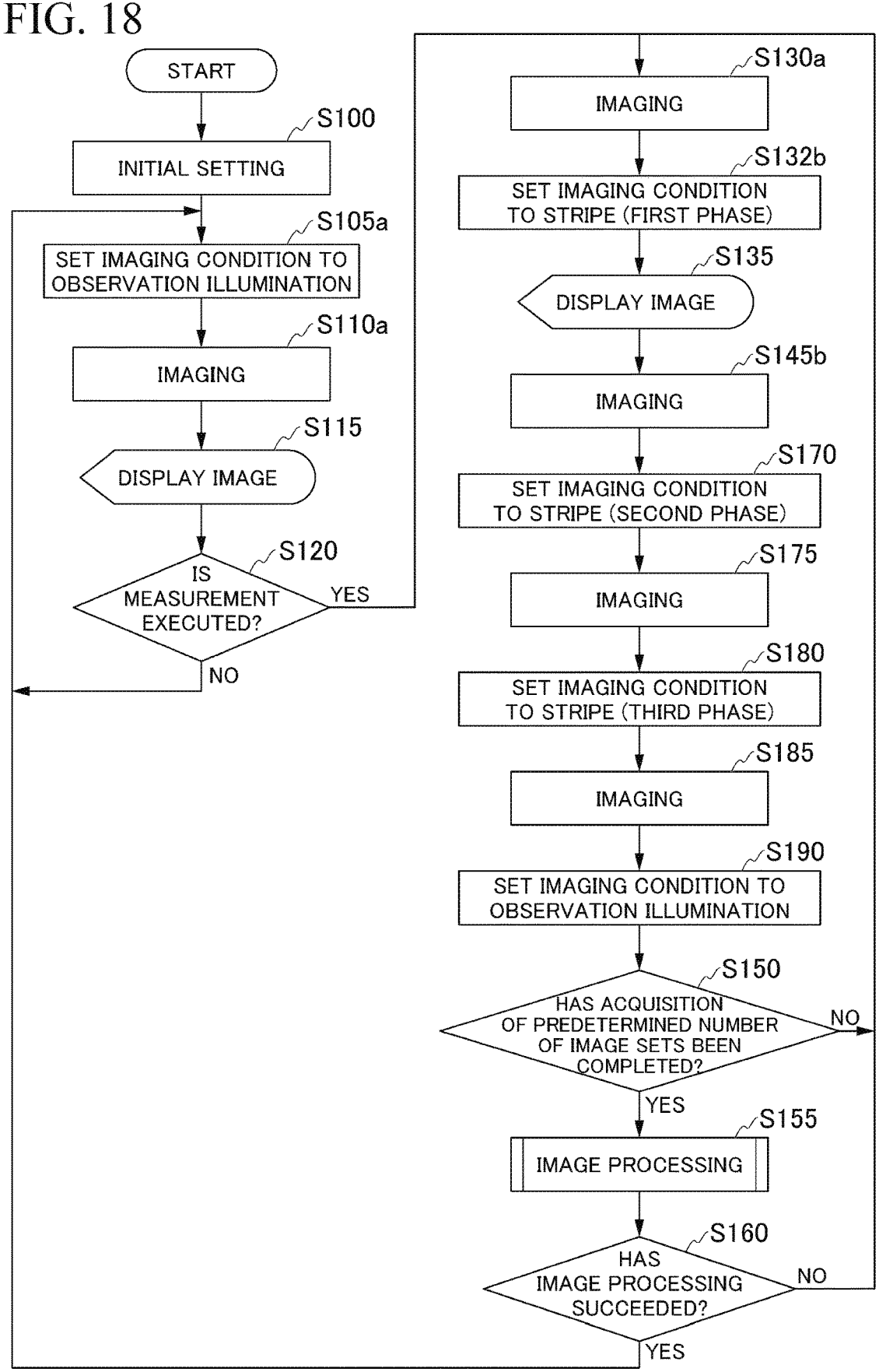
FIG. 18 is a flowchart showing a procedure of an operation of the endoscope device according to the fourth embodiment of the present invention.

FIG. 18 shows a procedure of an operation of the endoscope device 1b. The operation of the endoscope device 1b will be described with reference to FIG. 18. Descriptions of processing that is the same as that shown in FIG. 14 will be omitted.

When the control unit 340 determines to execute the measurement in step S120, the imaging device 22 generates an image of one frame and outputs the generated image. Because the imaging condition is the observation illumination, the imaging device 22 outputs a fourth image. When the third period is started, the illumination control unit 33a causes the white light source 37 to be turned off (step S130a).

After the step S130a, the illumination control unit 33a causes the LD 38 to be turned on and the phase shift unit 893 sets a first phase. Thereby, the illumination control unit 33a and the phase shift unit 893 set the imaging condition to a stripe having the first phase (the first imaging condition) (step S132b).

After step S132b, the imaging device 22 generates an image of one frame and outputs the generated image. Because the imaging condition is a stripe having the first phase, the imaging device 22 outputs a second image. When the third period starts, the illumination control unit 33a causes the LD 38 to be turned off (step S145b).

After step S145b, the illumination control unit 33a causes the LD 38 to be turned on and the phase shift unit 893 sets the second phase. The second phase is a phase obtained by shifting the first phase by $2\pi/3$. Thereby, the illumination control unit 33a and the phase shift unit 893 set the imaging condition to a stripe having the second phase (the second imaging condition) (step S170).

After step S170, the imaging device 22 generates an image of one frame and outputs the generated image. Because the imaging condition is a stripe having the second phase, the imaging device 22 outputs the second image. When the third period starts, the illumination control unit 33a causes the LD 38 to be turned off (step S175).

After step S175, the illumination control unit 33a causes the LD 38 to be turned on and the phase shift unit 893 sets the third phase. The third phase is a phase obtained by shifting the second phase by $2\pi/3$. Thereby, the illumination control unit 33a and the phase shift unit 893 set the imaging condition to a stripe having the third phase (the third imaging condition) (step S180).

After step S180, the imaging device 22 generates an image of one frame and outputs the generated image. Because the imaging condition is a stripe having the third phase, the imaging device 22 outputs the second image. When the third period starts, the illumination control unit 33a causes the LD 38 to be turned off (step S185).

After step S185, the illumination control unit 33a sets the imaging condition to observation illumination (the fourth imaging condition) by causing the white light source 37 to be turned on (step S190). After step S190, the processing in step S150 is executed.

The process shown in FIG. 10 is changed to the following process. An image set A and an image set B are input to the CPU 34. Each of the image set A and the image set B includes one first image, one second image, one third image, and one fourth image.

In a motion detection process (step S200) serving as the suitability determination process, the suitability determination unit 345 calculates a first value indicating first motion between two frames on the basis of the first image of the set A and the first image of the set B. In the motion detection process, the suitability determination unit 345 calculates a second value indicating second motion between two frames based on the second image of the set A and the second image of the set B. In the motion detection process, the suitability determination unit 345 calculates a third value indicating second motion between two frames on the basis of the third image of the set A and the third image of the set B. In the motion detection process, the suitability determination unit 345 calculates a fourth value indicating second motion between two frames on the basis of the fourth image of the set A and the fourth image of the set B. For example, the suitability determination unit 345 calculates an absolute value of the difference between pixel values of two images for each cell 54. The suitability determination unit 345 calculates a sum of absolute values of differences of pixel values of all pixels of the image. The suitability determination unit 345 calculates the first value, the second value, the third value, and the fourth value as determination parameters. The first value is a sum of absolute values of differences between pixel values calculated from the two first images. The second value is a sum of absolute values of differences between pixel values calculated from the two second images. The third value is a sum of absolute values of differences of pixel values calculated from the two third images.

The fourth value is a sum of absolute values of differences between pixel values calculated from the two fourth images. The motion detection method may be another method. The suitability determination method may be another method other than motion detection.

In step S205, the suitability determination unit 345 determines whether or not an image set is suitable for image processing of a subsequent stage. The suitability determination unit 345 determines whether or not each determination parameter is less than a predetermined value. When the suitability determination unit 345 determines that all of the determination parameters are less than the predetermined value, the suitability determination unit 345 determines that the image set is suitable (has suitability) for the image processing of the subsequent stage. When the suitability determination unit 345 determines that at least one of the determination parameters is greater than or equal to the predetermined value, the suitability determination unit 345 determines that the image set is not suitable (does not have any suitability) for image processing of the subsequent stage.

In the noise reduction process (step S215), the noise reduction unit 346 generates a first NR image (a fifth image) on the basis of the first image of the set A and the first image of the set B. A pixel value of the first NR image is an addition average of pixel values between the two first images. In the noise reduction process, the noise reduction unit 346 generates a second NR image (a sixth image) on the basis of the second image of the set A and the second image of the set B. A pixel value of the second NR image is an addition average of pixel values between the two second images. In the noise reduction process, the noise reduction unit 346 generates a third NR image (a seventh image) on the basis of the third image of the set A and the third image of the set B. A pixel value of the third NR image is an addition average of pixel values between the two third images.

In the measurement process (step S220), the measurement processing unit 347 generates a first corrected image by correcting optical distortion of the first NR image. In the measurement process, the measurement processing unit 347 generates a second corrected image by correcting optical distortion of the second NR image. In the measurement process, the measurement processing unit 347 generates a third corrected image by correcting optical distortion of the third NR image. In the measurement process, the measurement processing unit 347 calculates 3D coordinates of each point on the surface of the subject by a phase shift method using the first NR image, the second NR image, and the third NR image. The measurement processing unit 347 generates color 3D data. The color 3D data includes color information of each pixel of the fourth image and 3D coordinates corresponding to each pixel.

The visualization processing unit 343 generates a perspective projection image in the visualization process (step S225). The CPU 34 outputs the generated perspective projection image to the video processing unit 31. The video processing unit 31 outputs the perspective projection image to the display unit 5.

In the above example, the phase shift unit 893 sets three phases. The amount of change in the phase in switching of the imaging condition is 2π/3. The phase shift unit 893 may set four or more phases. When the four or more phases are set, the amount of change in the phase in switching of the imaging condition is π/2 or less. When the four or more phases are set, one or more images are acquired in addition to the three images (the first image, the second image, and the third image) corresponding to three phases.

The suitability determination unit 345 may calculate only any one of the first value, the second value, the third value, and the fourth value in the motion detection process. The suitability determination unit 345 may determine whether or not motion has been detected on the basis of only any one of the first value, the second value, the third value, and the fourth value. In the motion detection process, the suitability determination unit 345 may calculate only two of the first value, the second value, the third value, and the fourth value. The suitability determination unit 345 may determine whether or not motion has been detected on the basis of only any two of the first value, the second value, the third value, and the fourth value. The suitability determination unit 345 may calculate only three of the first value, the second value, the third value, and the fourth value in the motion detection process. The suitability determination unit 345 may determine whether or not motion has been detected on the basis of only any three of the first value, the second value, the third value, and the fourth value.

The imaging device 22 may generate a plurality of images under any one of the four imaging conditions and generate one image under the remaining three imaging conditions. In this case, the suitability determination unit 345 calculates any one of the first value, the second value, the third value, and the fourth value on the basis of a plurality of images generated under one imaging condition. The imaging device 22 may generate a plurality of images under any two of the four imaging conditions and generate one image under the remaining two imaging conditions. In this case, the suitability determination unit 345 calculates any two of the first value, the second value, the third value, and the fourth value on the basis of the plurality of images generated under the two imaging conditions. The imaging device 22 may generate a plurality of images under any three of the four imaging conditions and generate one image under the remaining one imaging condition. In this case, the suitability determination unit 345 calculates any three of the first value, the second value, the third value, and the fourth value on the basis of the plurality of images generated under the three imaging conditions.

The image processing unit 342 may process three or more image sets and select a set most suitable for image processing. Even if motion is detected between two images of two consecutive sets, there is a possibility that motion will not be detected between the other two images of the two consecutive sets. Thus, a probability of redoing of imaging decreases by selecting an object to be processed from three or more image sets. The noise reduction unit 346 can further reduce noise by executing the noise reduction process on the basis of the three or more images.

The white light source 37, the condenser lens 81, the light guide 82, the rod lens 83, and the diffusion lens 84 are optional. The illumination control unit 33a and the phase shift unit 893 may switch the imaging condition between only the first imaging condition, the second imaging condition, and the third imaging condition.

A means for generating a stripe pattern on the basis of second illumination light and a means for shifting a phase of the stripe pattern may be based on a method other than interference of laser light. For example, a method of projecting light emitted from an LED array and shifting the phase of the stripe pattern by switching an turning-on pattern of the LED array may be applied to the fourth embodiment.

The endoscope device 1b can shorten time intervals of three imaging operations on the subject to which pattern light having three types of phases is radiated. Also, the endoscope device 1b can shorten a time interval between imaging of the subject irradiated with the white light and imaging of the subject irradiated with the pattern light. Thus, as in the first embodiment, the quality of an image processing result is improved. Measurement accuracy is improved in measurement process. A deviation of color texture with respect to a reconstructed 3D shape of the subject becomes small. Furthermore, because the endoscope device 1b performs global exposure, it is possible to reduce deterioration in the quality of the image processing result due to an influence of rolling distortion.

Second illumination light generated by the LD 38 may be laser light having a wavelength other than that of blue. For example, the wavelength of the second illumination light may be a red, green, or infrared wavelength. Also, under at least one of the first imaging condition, the second imaging condition, and the third imaging condition, radiation of the first illumination light may not be stopped.

Fifth Embodiment

Figure 19:
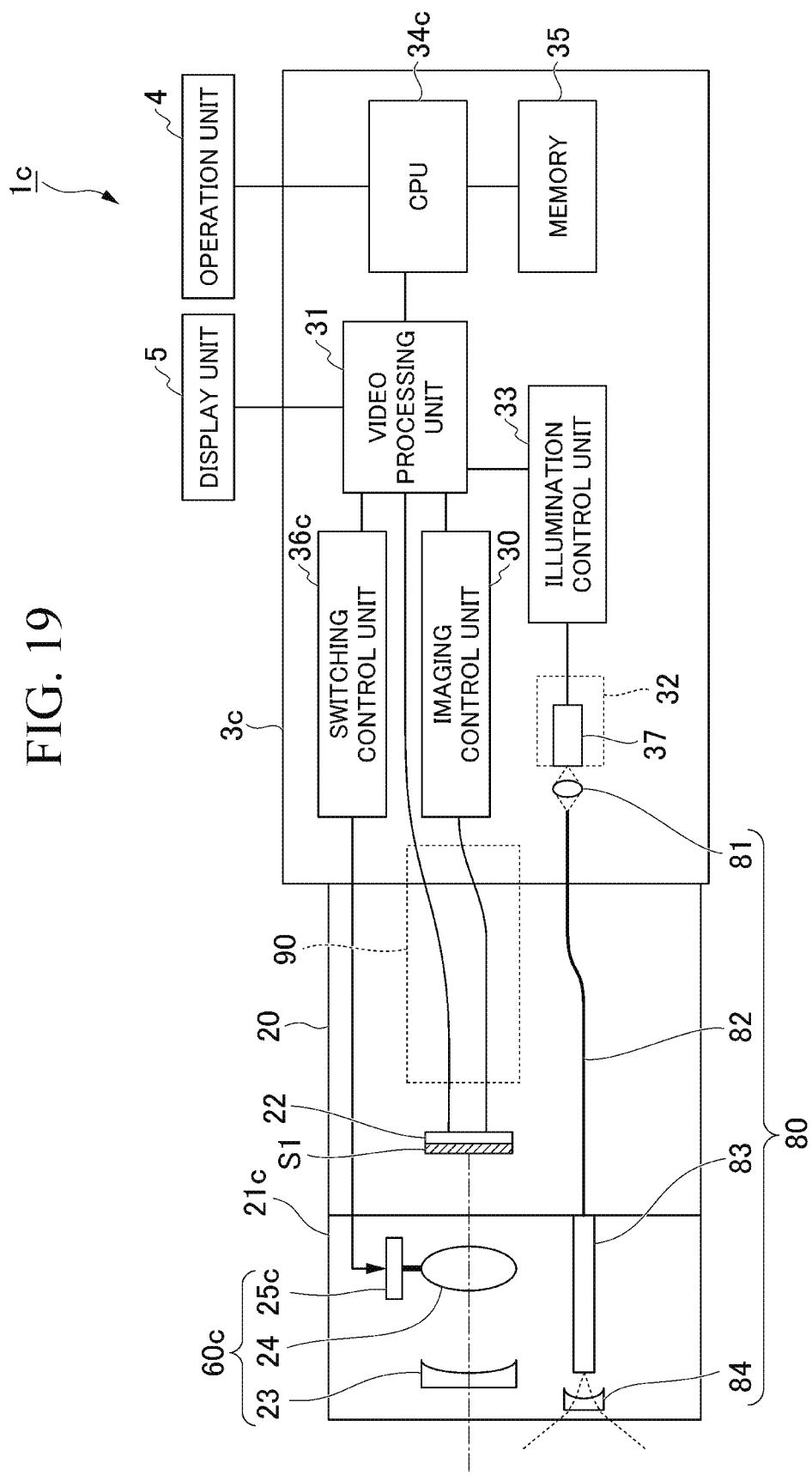
FIG. 19 is a block diagram showing a detailed configuration of an endoscope device according to a fifth embodiment of the present invention.

FIG. 19 shows a configuration of an endoscope device 1c according to a fifth embodiment of the present invention. Descriptions of parts that are the same as those shown in FIG. 2 will be omitted.

The main body unit 3 shown in FIG. 2 is changed to a main body unit 3c. In the main body unit 3c, the switching control unit 36 shown in FIG. 2 is changed to a switching control unit 36c. In the main body unit 3c, the CPU 34 shown in FIG. 2 is changed to a CPU 34c.

The optical adapter 21 shown in FIG. 2 is changed to an optical adapter 21c. In the optical adapter 21c, the observation optical system 60 shown in FIG. 2 is changed to an observation optical system 60c. The observation optical system 60c includes a concave lens 23, a convex lens 24, and a switching unit 25c. The concave lens 23 is the same as the concave lens 23 shown in FIG. 12. The convex lens 24 is the same as the convex lens 24 shown in FIG. 12.

Figure 20:
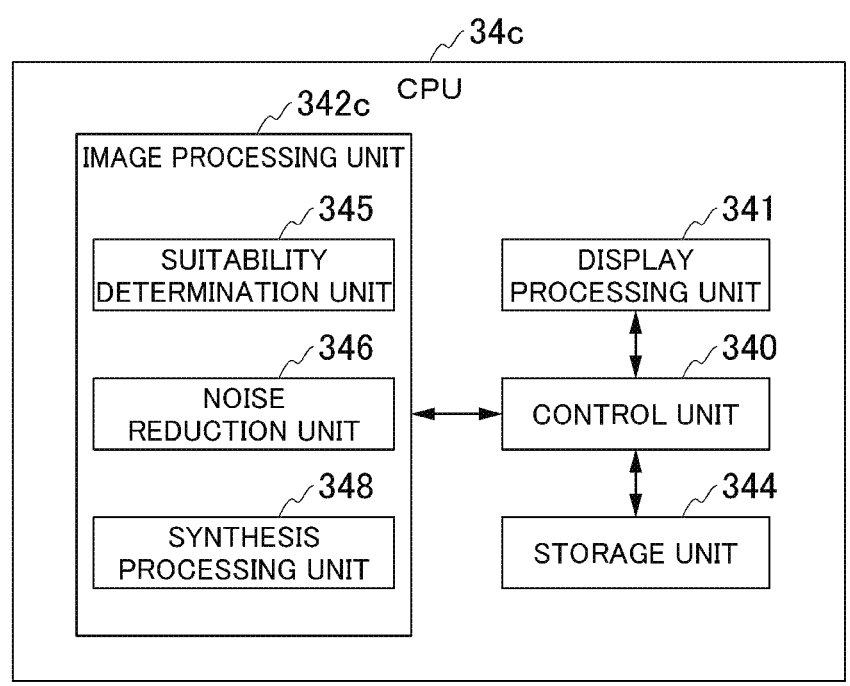
FIG. 20 is a block diagram showing a functional configuration of a central processing unit (CPU) according to the fifth embodiment of the present invention.

FIG. 20 shows a functional configuration of the CPU 34c. Descriptions of parts that are the same as those shown in FIG. 3 will be omitted. The CPU 34c does not have the visualization processing unit 343 shown in FIG. 3. The image processing unit 342 shown in FIG. 3 is changed to an image processing unit 342c. The image processing unit 342c includes a suitability determination unit 345, a noise reduction unit 346, and a synthesis processing unit 348.

The outline of parts different from those of FIG. 2 will be described. A focus of the observation optical system 60c under a first imaging condition is different from a focus of the observation optical system 60c under a second imaging condition. The synthesis processing unit 348 generates a third image by synthesizing a first image and a second image.

The switching control unit 36c causes the switching unit 25c to start switching of the imaging condition during a third period and complete the switching of the imaging condition during the third period.

The switching control unit 36c causes the switching unit 25c to set the first imaging condition during a plurality of first frame periods. The switching control unit 36c causes the switching unit 25c to set the second imaging condition during a plurality of second frame periods. Each second frame period of the plurality of second frame periods is different from each first frame period of the plurality of first frame periods. The noise reduction unit 346 generates a fourth image by performing a noise reduction process on a plurality of first images. The noise reduction unit 346 generates a fifth image by performing the noise reduction process on a plurality of second images. The synthesis processing unit 348 generates the third image by synthesizing the fourth image and the fifth image.

Details of parts different from those of FIG. 2 will be described. The switching unit 25c has a direct-acting solenoid. A mover of the solenoid is connected to the convex lens 24. The switching control unit 36c supplies electric power to the switching unit 25c. The switching control unit 36c causes the switching unit 25c to switch a position of the solenoid. The switching unit 25c switches the focus of the observation optical system 60c by switching the position of the solenoid. For example, a first focus under the first imaging condition is a far point and a second focus under the second imaging condition is a near point. The first focus under the first imaging condition may be a near point and the second focus under the second imaging condition may be a far point. The synthesis processing unit 348 synthesizes a plurality of images having different focuses to perform depth synthesis. According to the depth synthesis, a depth of field of an image increases.

Figure 21:
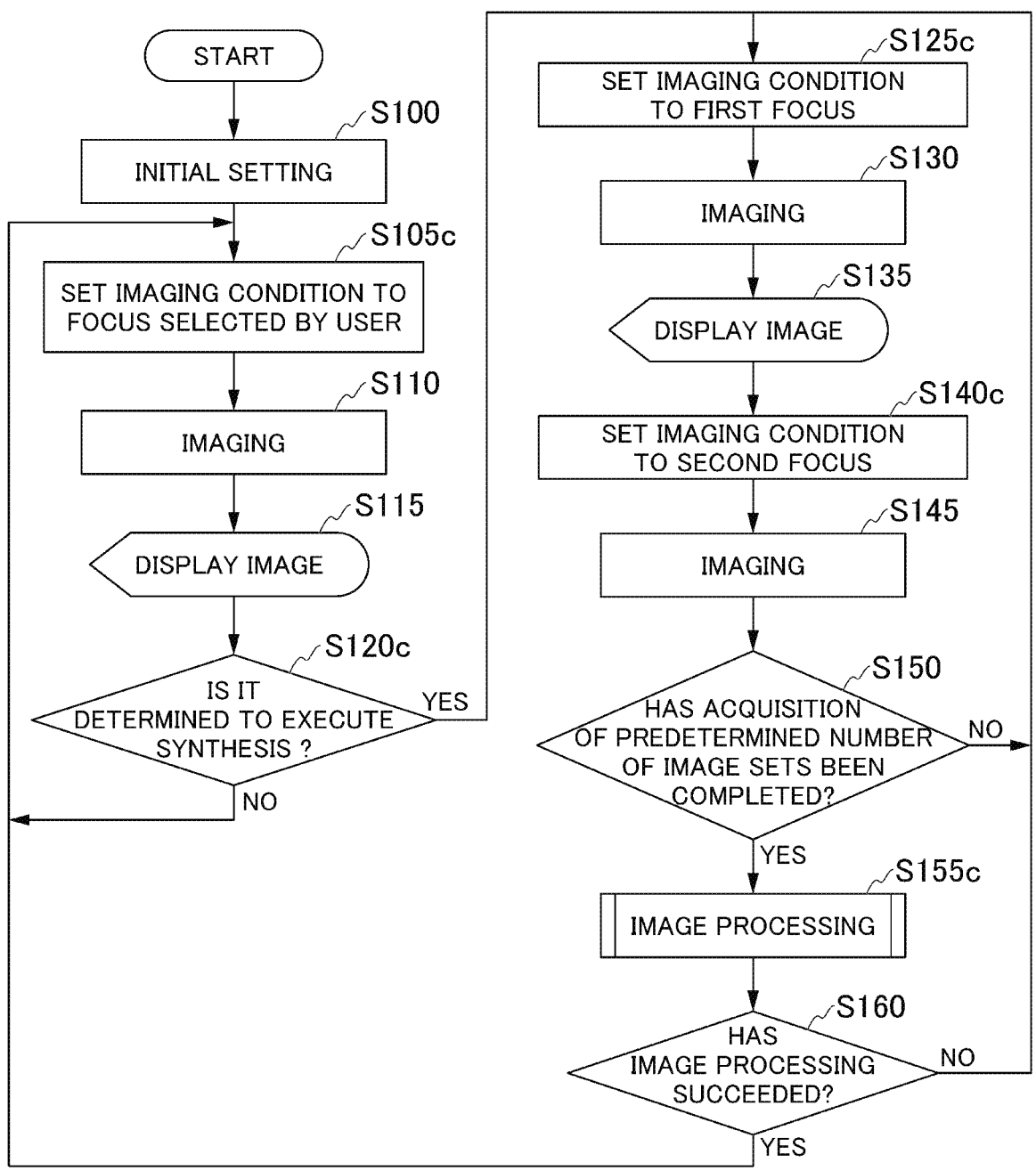
FIG. 21 is a flowchart showing a procedure of an operation of the endoscope device according to the fifth embodiment of the present invention.

FIG. 21 shows a procedure of the operation of the endoscope device 1c. The operation of the endoscope device 1c will be described with reference to FIG. 21. Descriptions of processing that is the same as that shown in FIG. 9 will be omitted.

After step S100, the switching control unit 36c outputs a focus switching control signal to the switching unit 25c. For example, the user inputs a focus indication by operating the operation unit 4. For example, the focus indicated by the user is one of a first focus and a second focus. The switching control unit 36c outputs a control signal indicating the focus indicated by the user to the switching unit 25c. Thereby, the switching control unit 36c causes the switching unit 25c to start switching of the imaging condition. The switching unit 25c starts focus switching on the basis of the control signal from the switching control unit 36c. Thereafter, the switching control unit 36c causes the switching unit 25c to complete the focus switching (step S105c). When the imaging condition is the focus indicated by the user in step S105c, the processing in step S105c is unnecessary. After step S105c, the processing in step S110 is executed.

After step S115, the control unit 340 determines whether or not to execute synthesis (step S120c). For example, when the user inputs a synthesis instruction by operating the operation unit 4, the control unit 340 determines to execute synthesis.

When the control unit 340 determines not to execute the synthesis in step S120c, the processing in step S105c is executed. The focus of the observation optical system 60c is maintained as the focus indicated by the user until the synthesis instruction is input. Until the synthesis instruction is input, the imaging device 22 sequentially outputs images and the display unit 5 sequentially updates and displays the images.

When the control unit 340 determines to execute the synthesis in step S120c, the switching control unit 36c outputs a focus switching control signal to the switching unit 25c. Thereby, the switching control unit 36c causes the switching unit 25c to start focus switching. The switching unit 25c starts switching from the focus indicated by the user to the first focus or switching from the second focus to the first focus on the basis of the control signal from the switching control unit 36c. Thereafter, the switching control unit 36c causes the switching unit 25c to complete the focus switching. Thereby, the switching control unit 36c sets the imaging condition to the first focus (a first imaging condition) (step S125c). After step S125c, the processing in step S130 is executed.

After step S135, the switching control unit 36c outputs the focus switching control signal to the switching unit 25c. Thereby, the switching control unit 36c causes the switching unit 25c to start the focus switching. The switching unit 25c starts switching from the first focus to the second focus on the basis of the control signal from the switching control unit 36c. Thereafter, the switching control unit 36c causes the switching unit 25c to complete the focus switching. Thereby, the switching control unit 36c sets the imaging condition to the second focus (a second imaging condition) (step S140c). After step S140c, the processing in step S145 is executed.

When the control unit 340 determines that the acquisition of a predetermined number of image sets has been completed in step S150, the image processing unit 342c executes image processing (step S155c). After step S155c, the processing in step S160 is executed.

Figure 22:
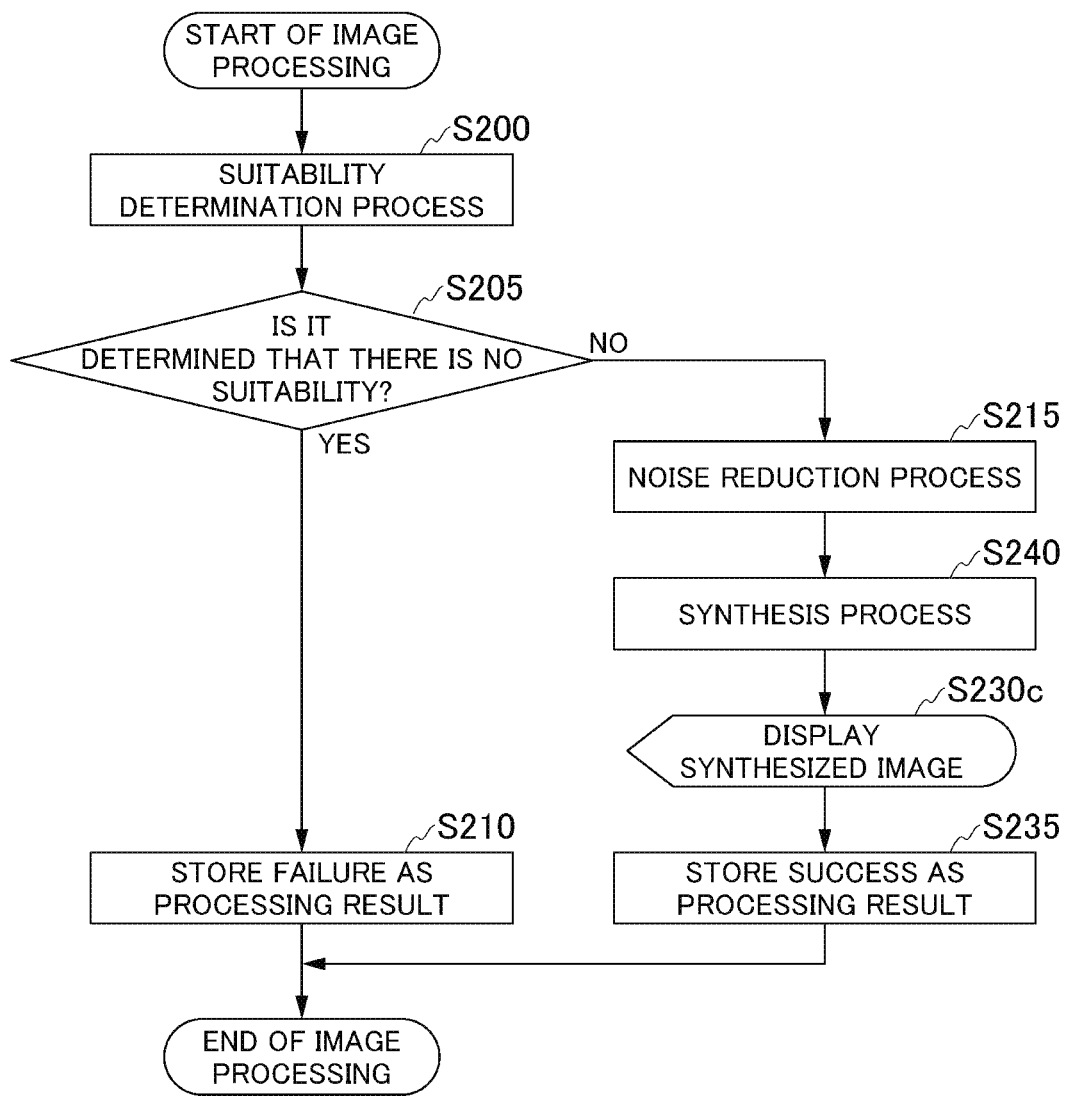
FIG. 22 is a flowchart showing a procedure of the operation of the endoscope device according to the fifth embodiment of the present invention.

FIG. 22 shows details of image processing in step S155c. The operation of the endoscope device 1c will be described with reference to FIG. 22. Descriptions of processing that is the same as that shown in FIG. 10 will be omitted.

When the suitability determination unit 345 determines that there is suitability in step S205, the noise reduction unit 346 executes a noise reduction process. In the noise reduction process, the noise reduction unit 346 generates a first NR image (a fourth image) on the basis of a first image of a set A and a first image of a set B. A pixel value of the first NR image is an addition average of pixel values between the two first images. In the noise reduction process, the noise reduction unit 346 generates a second NR image (a fifth image) on the basis of a second image of the set A and a second image of the set B. A pixel value of the second NR image is an addition average of pixel values between the two second images (step S215).

After step S215, the synthesis processing unit 348 executes a synthesis process. The synthesis processing unit 348 generates a first contrast map and a second contrast map in the synthesis process. The first contrast map includes a first value of contrast at each pixel of the first NR image. The second contrast map includes a second value of contrast at each pixel of the second NR image. The synthesis processing unit 348 compares the first value with the second value for each pixel in the synthesis process. The synthesis processing unit 348 selects a pixel value of the first NR image in a pixel in which the first value is greater than the second value. The synthesis processing unit 348 selects the pixel value of the second NR image in a pixel in which the second value is greater than the first value. In the synthesis process, the synthesis processing unit 348 generates a third image including the selected pixel values as a synthesized image (step S240).

After step S240, the display processing unit 341 causes the display unit 5 to display the synthesized image generated in step S240. The display unit 5 displays the synthesized image (step S230c). After step S230c, the processing in step S235 is executed.

When the noise reduction process in step S215 is not executed, the synthesis processing unit 348 executes the synthesis process using one image set. The synthesis processing unit 348 generates a third image by synthesizing the first image corresponding to the first focus and the second image corresponding to the second focus. One image set may be selected from a plurality of image sets and the synthesis processing unit 348 may execute the synthesis process using the selected image set.

The synthesis processing unit 348 may synthesize three or more images.

Focuses of the observation optical system 60c when the three or more images are generated are different from each other.

The endoscope device 1c can shorten a time interval between imaging in the first focus and imaging in the second focus. Thus, as in the first embodiment, the quality of the image processing result is improved. In the image, the occurrence of an unnatural edge due to movement of the subject while the focus is being changed or movement of a tip of an insertion unit 20 is suppressed. Furthermore, because the endoscope device 1c performs global exposure, it is possible to reduce the deterioration of the quality of the image processing result due to an influence of rolling distortion. Therefore, the quality of a depth synthesis result is improved.

Sixth Embodiment

Figure 23:
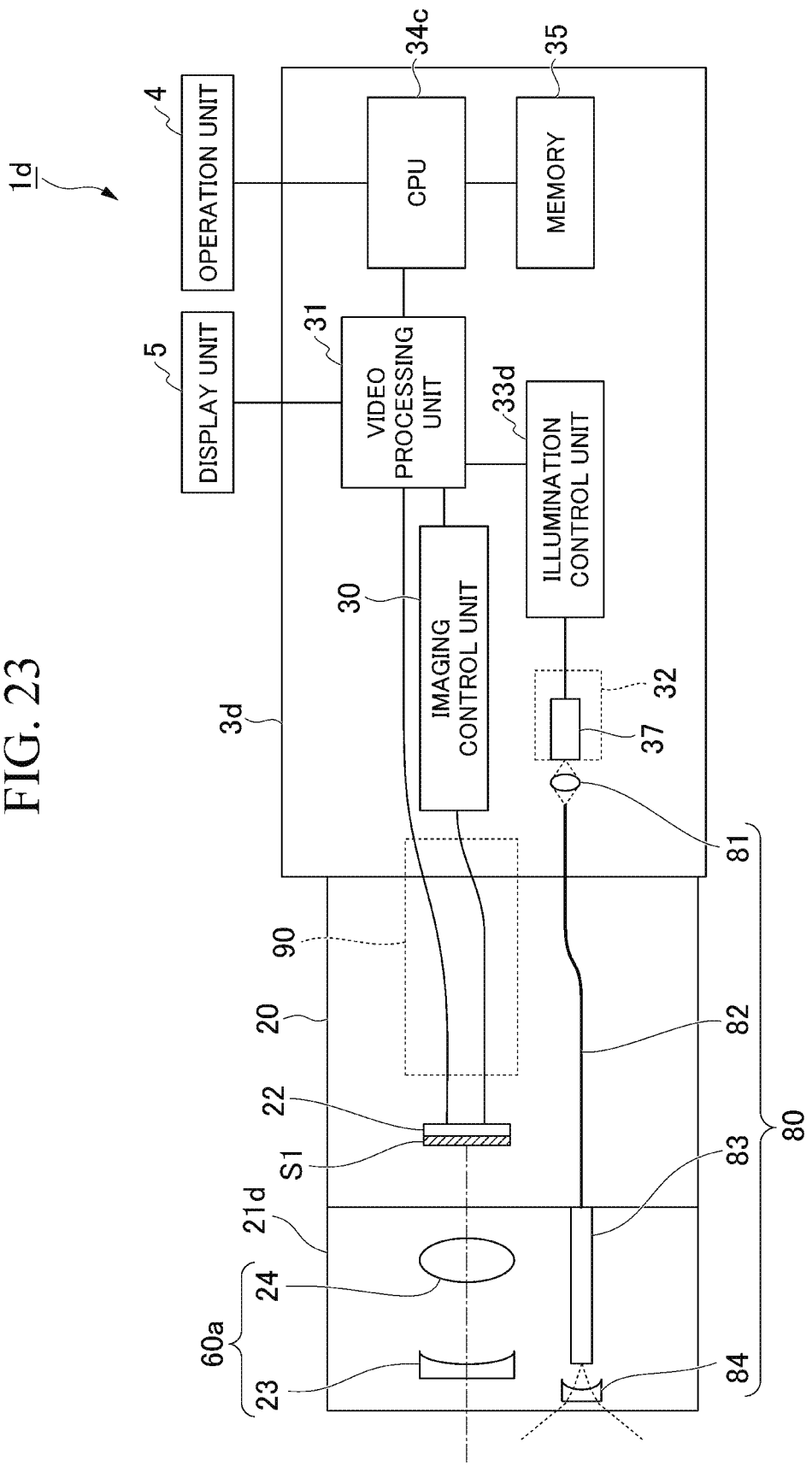
FIG. 23 is a block diagram showing a detailed configuration of an endoscope device according to a sixth embodiment of the present invention.

FIG. 23 shows a configuration of an endoscope device 1d according to a sixth embodiment of the present invention. Descriptions of parts that are the same as those shown in FIG. 2 will be omitted.

The main body unit 3 shown in FIG. 2 is changed to a main body unit 3d. The main body unit 3d does not have the switching control unit 36. In the main body unit 3d, the illumination control unit 33 shown in FIG. 2 is changed to an illumination control unit 33d. In the main body unit 3d, the CPU 34 shown in FIG. 2 is changed to a CPU 34c. The CPU 34c is the same as the CPU 34c shown in FIG. 19.

The optical adapter 21 shown in FIG. 2 is changed to an optical adapter 21d. In the optical adapter 21d, the observation optical system 60 shown in FIG. 2 is changed to an observation optical system 60a. The observation optical system 60a is the same as the observation optical system 60a shown in FIG. 12.

The outline of parts different from those of FIG. 2 will be described. The amount of light of the white light source 37 under a first imaging condition is different from the amount of light of the white light source 37 under a second imaging condition. The synthesis processing unit 348 of the image processing unit 342c generates a third image by synthesizing a first image and a second image.

The illumination control unit 33d functions as a switching unit and a switching control unit. The illumination control unit 33d starts switching of the imaging condition during the third period and completes the switching of the imaging condition during the third period. The illumination control unit 33d completes the switching of the imaging condition before the next second period is started. That is, the illumination control unit 33d completes the switching of the imaging conditions during the third period that is the same as the third period during which the switching of the imaging condition has been started.

The illumination control unit 33d sets a first imaging condition during a plurality of first frame periods. The illumination control unit 33d sets a second imaging condition during a plurality of second frame periods. Each second frame period of the plurality of second frame periods is different from each first frame period of the plurality of first frame periods. The noise reduction unit 346 generates a fourth image by executing a noise reduction process on the plurality of first images. The noise reduction unit 346 generates a fifth image by executing the noise reduction process on the plurality of second images. The synthesis processing unit 348 generates the third image by synthesizing the fourth image and the fifth image.

Details of parts different from those of FIG. 2 will be described. The illumination control unit 33d switches the imaging condition by switching the amount of light of the white light source 37. The brightness of illumination light under the first imaging condition is different from the brightness of illumination light under the second imaging condition. Thus, an exposure amount of the cell 54 under the first imaging condition is different from an exposure amount of the cell 54 under the second imaging condition. The synthesis processing unit 348 executes high dynamic range (HDR) synthesis by synthesizing a plurality of images having different amounts of exposure. The HDR synthesis widens a dynamic range of the image.

Figure 24:
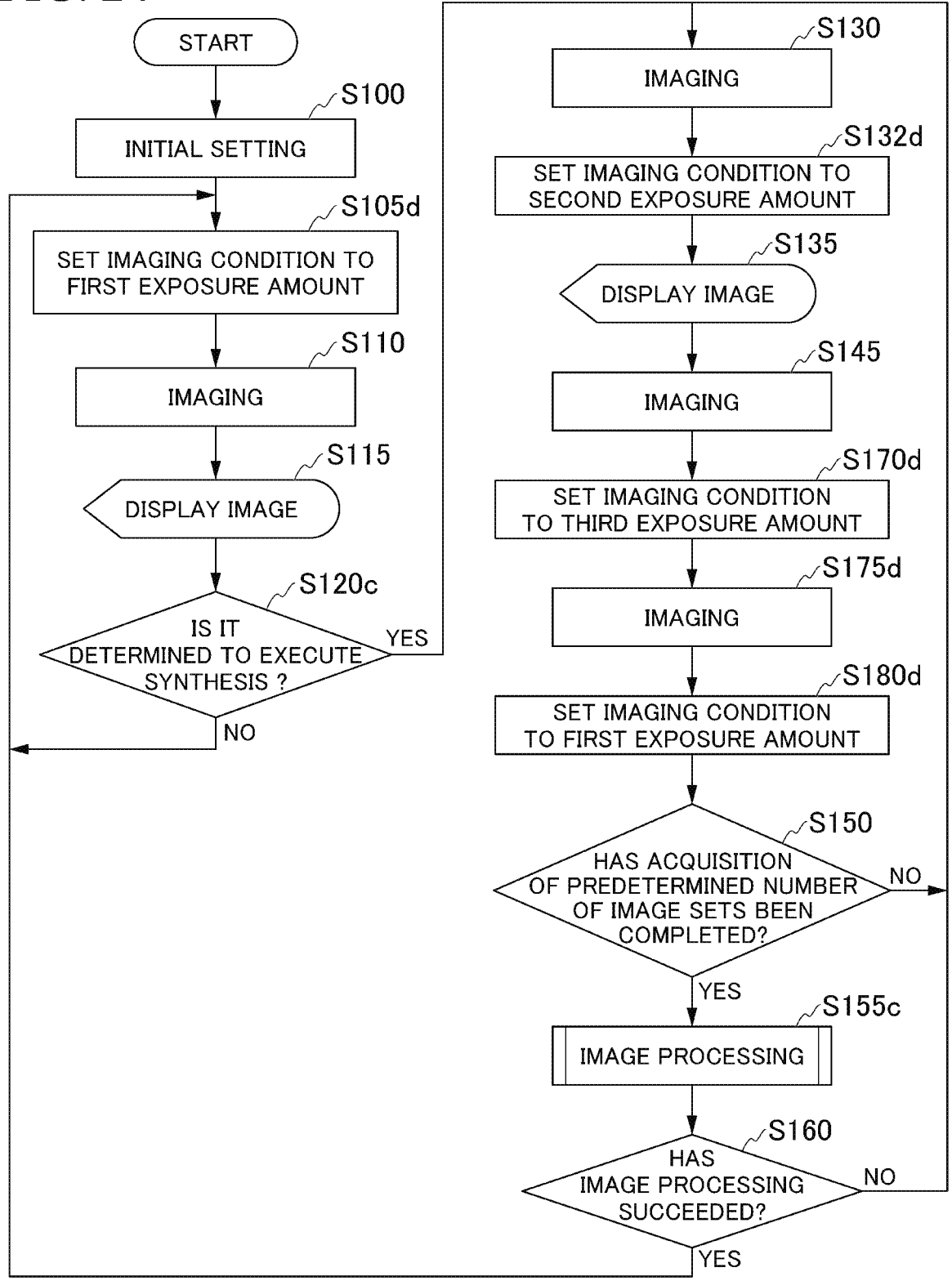
FIG. 24 is a flowchart showing a procedure of an operation of the endoscope device according to the sixth embodiment of the present invention.

FIG. 24 shows a procedure of the operation of the endoscope device 1d. The operation of the endoscope device 1d will be described with reference to FIG. 24. Descriptions of processing that is the same as that shown in FIG. 21 will be omitted.

After step S100, the illumination control unit 33d sets the amount of light of the white light source 37 to a predetermined suitable amount of light. Thereby, the illumination control unit 33d sets the imaging condition to a first exposure amount (step S105d). After step S105d, the processing in step S110 is executed.

After step S130, the illumination control unit 33d sets the amount of light of the white light source 37 to ¼ of a suitable amount of light. Thereby, the illumination control unit 33d sets the imaging condition to a second exposure amount (the second imaging condition) (step S132d). After step S132d, the processing in step S135 is executed.

After step S145, the illumination control unit 33d sets the amount of light of the white light source 37 to four times the suitable amount of light. Thereby, the illumination control unit 33d sets the imaging condition to a third exposure amount (the third imaging condition) (step S170d).

After step S170d, the imaging device 22 generates an image of one frame and outputs the generated image (step S175d).

After step S175d, the illumination control unit 33d sets the amount of light of the white light source 37 to a predetermined suitable amount of light. Thereby, the illumination control unit 33d sets the imaging condition to the first exposure amount (the first imaging condition) (step S180d). After step S180d, the processing in step S150 is executed.

The image processing in step S155c includes the processing shown in FIG. 22. Parts different from the image processing in the fifth embodiment will be described.

The image set A and the image set B are input to the CPU 34c. Each of the image set A and the image set B includes one first exposure image, one second exposure image, and one third exposure image. The first exposure image is an image generated when the imaging condition is the first exposure amount. The second exposure image is an image generated when the imaging condition is the second exposure amount. The third exposure image is an image generated when the imaging condition is the third exposure amount.

In the motion detection process (step S200), the suitability determination unit 345 calculates a first value indicating first motion between two frames on the basis of the first exposure image of the set A and the first exposure image of the set B. In the motion detection process, the suitability determination unit 345 calculates a second value indicating second motion between two frames on the basis of the second exposure image of the set A and the second exposure image of the set B. In the motion detection process, the suitability determination unit 345 calculates a third value indicating third motion between two frames on the basis of the third exposure image of the set A and the third exposure image of the set B. For example, the suitability determination unit 345 calculates an absolute value of the difference between the pixel values in each pixel between two images for each pixel of the image. The suitability determination unit 345 calculates a sum of absolute values of differences of pixel values in all the cells 54. The first value is a sum of absolute values of differences between pixel values calculated from the two first exposure images. The second value is a sum of absolute values of differences between pixel values calculated from the two second exposure images. The third value is a sum of absolute values of differences between pixel values calculated from the two third exposure images. The motion detection method may be another method.

In step S205, the suitability determination unit 345 determines whether or not motion has been detected. The suitability determination unit 345 determines whether or not each of the first value, the second value, and the third value is less than a predetermined value. When the suitability determination unit 345 determines that all of the first value, the second value, and the third value are less than the predetermined value, the suitability determination unit 345 determines that no motion has been detected (that no motion has occurred or that there is no motion). When the suitability determination unit 345 determines that at least one of the first value, the second value, and the third value is greater than or equal to the predetermined value, the suitability determination unit 345 determines that motion has been detected (that motion has occurred or that there is motion).

In the noise reduction process (step S215), the noise reduction unit 346 generates a first NR image (a fourth image) on the basis of the first exposure image of the set A and the first exposure image of the set B. A pixel value of the first NR image is an addition average of pixel values between the two first exposure images. In the noise reduction process, the noise reduction unit 346 generates a second NR image (a fifth image) on the basis of the second exposure image of the set A and the second exposure image of the set B. A pixel value of the second NR image is an addition average of pixel values between the two second exposure images. In the noise reduction process, the noise reduction unit 346 generates a third NR image (a sixth image) on the basis of the third exposure image of the set A and the third exposure image of the set B. A pixel value of the third NR image is an addition average of pixel values between the two third exposure images.

After step S215, the synthesis processing unit 348 executes a synthesis process. In the synthesis process, the synthesis processing unit 348 generates a third image as a synthesized image by synthesizing the first NR image, the second NR image, and the third NR image (step S240).

In the synthesized image, whiteout and blackout are suppressed. When the synthesized image is displayed in step S230c, a dark place within a visual field and a bright place within the visual field are displayed with appropriate brightness.

When the noise reduction process in step S215 is not executed, the synthesis processing unit 348 executes the synthesis process using one image set. The synthesis processing unit 348 generates the third image by synthesizing the first exposure image corresponding to the first exposure amount, the second exposure image corresponding to the second exposure amount, and the third exposure image corresponding to the third exposure amount. One image set may be selected from a plurality of image sets and the synthesis processing unit 348 may execute the synthesis process using the selected image set.

The suitability determination unit 345 may calculate only any one of the first value, the second value, and the third value in the motion detection process. The suitability determination unit 345 may determine whether or not motion has been detected on the basis of only any one of the first value, the second value, and the third value. The suitability determination unit 345 may calculate only any two of the first value, the second value, and the third value in the motion detection process. The suitability determination unit 345 may determine whether or not motion has been detected on the basis of only on any two of the first value, the second value, and the third value.

The imaging device 22 may generate a plurality of images under any one of three imaging conditions and generate one image under the remaining two imaging conditions. In this case, the suitability determination unit 345 calculates any one of the first value, the second value, and the third value on the basis of the plurality of images generated under the one imaging condition. The imaging device 22 may generate a plurality of images under any two of the three imaging conditions and generate one image under the remaining one imaging condition. In this case, the suitability determination unit 345 calculates any two of the first value, the second value, and the third value on the basis of the plurality of images generated under the two imaging conditions.

The synthesis processing unit 348 may synthesize the two images. Amounts of light of the white light source 37 when the two images are generated are different from each other. The synthesis processing unit 348 may synthesize four or more images. Amounts of light of the white light source 37 when the four or more images are generated are different from each other.

The endoscope device 1d can shorten time intervals between imaging in the first exposure amount, imaging in the second exposure amount and imaging in the third exposure amount. Thus, as in the first embodiment, the quality of the image processing result is improved. In an image, the occurrence of an unnatural edge due to the motion of the subject while the exposure amount is being changed or the movement of a tip of an insertion unit 20 is suppressed. Furthermore, because the endoscope device 1d performs global exposure, it is possible to reduce deterioration in the quality of the image processing result due to an influence of rolling distortion. Thus, the quality of an HDR synthesis result is improved.

Seventh Embodiment

Figure 25:
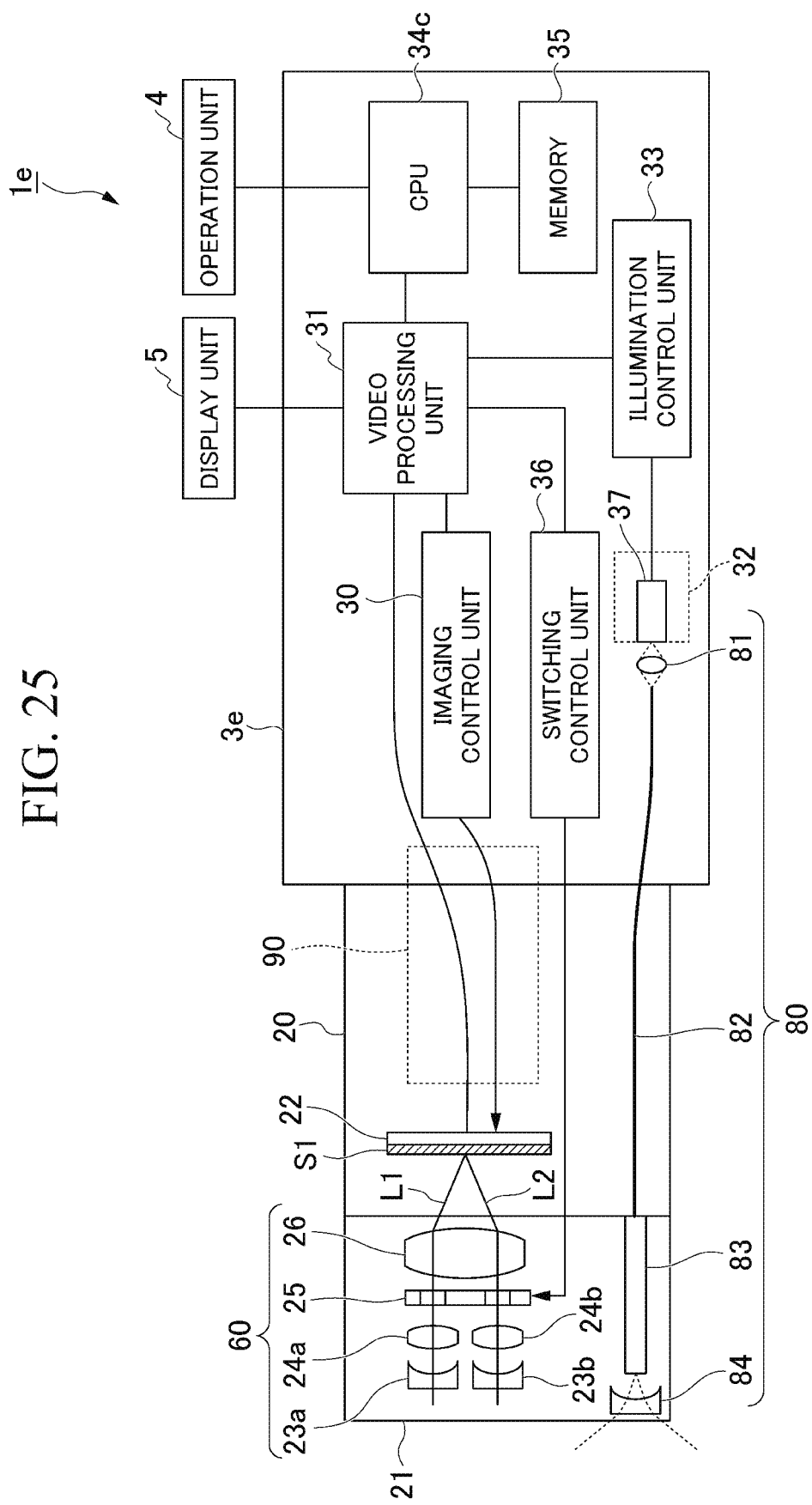
FIG. 25 is a block diagram showing a detailed configuration of an endoscope device according to a seventh embodiment of the present invention.

FIG. 25 shows a configuration of an endoscope device 1e according to a seventh embodiment of the present invention. Descriptions of parts that are the same as those shown in FIG. 2 will be omitted.

The main body unit 3 shown in FIG. 2 is changed to a main body unit 3e. In the main body unit 3e, the CPU 34 shown in FIG. 2 is changed to a CPU 34c. The CPU 34c is the same as the CPU 34c shown in FIG. 19.

The outline of parts different from those of FIG. 2 will be described. The observation optical system 60 includes a first optical system, a second optical system, and a switching unit 25. A concave lens 23a, a convex lens 24a, and an image forming optical system 26 are the first optical system. The first optical system is disposed on an optical front side (a subject side) of the imaging device 22 and forms a first optical image on the imaging device 22 based on light from the subject. A concave lens 23b, a convex lens 24b, and an image forming optical system 26 are the second optical system. The second optical system is disposed on an optical front side (a subject side) of the imaging device 22 and forms a second optical image on the imaging device 22 based on light from the subject. The switching unit 25 selects either one of the first optical system and the second optical system and causes only either one of the first optical image and the second optical image to be formed on the imaging device 22.

A visual field of the first optical system and a visual field of the second optical system have a common region. The switching control unit 36 switches an optical image formed on the imaging device 22 by controlling the switching unit 25. Under a first imaging condition, the first optical image is formed on the imaging device 22. Under a second imaging condition, the second optical image is formed on the imaging device 22. The synthesis processing unit 348 aligns a region of a first image corresponding to the common region and a region of a second image corresponding to the common region and generates a third image by synthesizing the first image and the second image.

The switching control unit 36 causes the switching unit 25 to set a first imaging condition during a plurality of first frame periods. The switching control unit 36 causes the switching unit 25 to set a second imaging condition during a plurality of second frame periods. Each second frame period of the plurality of second frame periods is different from each first frame period of the plurality of first frame periods. The noise reduction unit 346 generates a fourth image by performing a noise reduction process on a plurality of first images. The noise reduction unit 346 generates a fifth image by executing the noise reduction process on a plurality of second images. The synthesis processing unit 348 generates the third image by synthesizing the fourth image and the fifth image.

Details of parts different from those of FIG. 2 will be described. The first optical system and the second optical system have parallaxes with respect to each other. Thus, the visual field of the first optical system and the visual field of the second optical system are different from each other. An optical axis of the first optical system and an optical axis of the second optical system are substantially parallel to each other. A part of the visual field of the first optical system is the same as a part of the visual field of the second optical system. The visual field of the first optical system includes a first region and a common region. The visual field of the second optical system includes a second region and a common region. The second region is different from the first region.

The synthesis processing unit 348 executes panorama synthesis by synthesizing a plurality of images having visual fields different from each other. In the panorama synthesis, the synthesis processing unit 348 synthesizes a plurality of images after aligning common regions so that the common regions of images are included. The panorama synthesis widens the visual field in the image.

The endoscope device 1e executes the process shown in FIG. 9. The image processing in step S155 shown in FIG. 9 includes the process shown in FIG. 22. Parts different from the image processing in the first embodiment will be described.

In the synthesis process (step S240), the synthesis processing unit 348 generates a third image as a synthesized image by synthesizing the first NR image and the second NR image. In this process, the common regions of the images are aligned and the common region of the first NR image overlaps the common region of the second NR image.

When the noise reduction process in step S215 is not executed, the synthesis processing unit 348 executes a synthesis process using one image set. The synthesis processing unit 348 generates a third image by synthesizing the first image corresponding to the first optical system and the second image corresponding to the second optical system. One image set may be selected from a plurality of image sets and the synthesis processing unit 348 may execute the synthesis process using the selected image set.

The optical axis of the first optical system and the optical axis of the second optical system may not be parallel to each other. For example, the optical axis of the first optical system may extend toward an optical front side of the imaging device 22 and the first optical system may have a visual field of 120 degrees in left and right directions. The optical axis of the second optical system may be orthogonal to the optical axis of the first optical system and the second optical system may have a visual field of 120 degrees in the left and right directions. In this case, a region of 15 degrees on the right side in the visual field of the first optical system and a region of 15 degrees on the left side in the visual field of the second optical system are the common regions.

The endoscope device 1e can shorten a time interval between imaging in the first visual field and imaging in the second visual field. Thus, as in the first embodiment, the quality of the image processing result is improved. In an image, the occurrence of an unnatural edge due to motion of the subject while the visual field is being changed or movement of a tip of an insertion unit 20 is suppressed. Furthermore, because the endoscope device 1e performs global exposure, it is possible to reduce the deterioration of the quality of the image processing result due to an influence of rolling distortion. Thus, the quality of the result of the panorama synthesis is improved.

(Supplement)

According to an aspect of the present invention, a method of operating an endoscope device including a first step, a second step, and a third step is provided. The endoscope device includes a light source, an illumination optical system, an observation optical system, an imaging device, a switching unit, and a control unit. The light source generates illumination light. The illumination optical system radiates the illumination light to a subject. The observation optical system forms an optical image of the subject. The imaging device has a plurality of pixels disposed in a matrix, and images the subject. The imaging device sequentially reads pixel signals from at least some of the plurality of pixels row by row during a first period. The imaging device generates an image of the subject during each frame period of a plurality of frame periods on the basis of the pixel signals read from at least some of the plurality of pixels. The pixel signals are generated on the basis of the optical image of the subject. The switching unit performs switching between a plurality of imaging conditions so that the imaging device images the subject. In the first step, the control unit causes the light source to generate the illumination light during a second period. The second period is at least a part of a period other than the first period. In the second step, the control unit causes the light source to stop the generation of the illumination light during a third period. The third period is all of a period other than the second period and includes the first period. The second period and the third period are alternately iterated. In the third step, the control unit causes the switching unit to start switching of the imaging condition during the third period and complete the switching of the imaging condition during the third period.

According to an aspect of the present invention, a program for causing a processor of an endoscope device to execute a first step, a second step, and a third step is provided. The endoscope device includes the light source, the illumination optical system, the observation optical system, the imaging device, the switching unit, and the processor. In the first step, the processor causes the light source to generate the illumination light during a second period. The second period is at least a part of a period other than the first period. In the second step, the processor causes the light source to stop the generation of the illumination light during a third period. The third period is all of a period other than the second period and includes the first period. The second period and the third period are alternately iterated. In the third step, the processor causes the switching unit to start switching of the imaging condition during the third period and complete the switching of the imaging condition during the third period.

According to an aspect of the present invention, a computer-readable non-transitory recording medium recording a program for causing a processor of an endoscope device to execute a first step, a second step, and a third step is provided. The endoscope device includes the light source, the illumination optical system, the observation optical system, the imaging device, the switching unit, and the processor. In the first step, the processor causes the light source to generate the illumination light during a second period. The second period is at least a part of a period other than the first period. In the second step, the processor causes the light source to stop the generation of the illumination light during a third period. The third period is all of a period other than the second period and includes the first period. The second period and the third period are alternately iterated. In the third step, the processor causes the switching unit to start switching of the imaging condition during the third period and complete the switching of the imaging condition during the third period.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope device comprising:
a light source configured to generate illumination light;
an illumination optical system configured to radiate the illumination light to a subject;
an observation optical system configured to form an optical image of the subject;
an imaging device having a plurality of pixels disposed in a matrix and configured to image the subject, sequentially read pixel signals from at least some of the plurality of pixels row by row during a first period, and generate an image data of the subject during each frame period of a plurality of frame periods on the basis of the pixel signals read from at least some of the plurality of pixels, the pixel signals being generated on the basis of the optical image of the subject;
a switching unit configured to perform switching between a plurality of imaging conditions so that the imaging device images the subject; and
a control unit,
wherein the control unit causes the light source to generate the illumination light during a second period, the second period being at least a part of a period other than the first period,
the control unit causes the light source to stop the generation of the illumination light during a third period, the third period is all of a period other than the second period and includes the first period, and the second period and the third period are alternately iterated, and
the control unit causes the switching unit to start switching of the imaging condition during the third period and complete the switching of the imaging condition during the third period.

2. The endoscope device according to claim 1, wherein the imaging device reads the pixel signals in a time period that is less than or equal to half a length of each frame period of the plurality of frame periods during the first period.

3. The endoscope device according to claim 1, further comprising an image processing unit configured to execute image processing on a plurality of images generated during the plurality of frame periods,
wherein the plurality of imaging conditions include a first imaging condition and a second imaging condition,
the first imaging condition and the second imaging condition are different from each other,
the imaging device generates a first image of the subject by imaging the subject under the first imaging condition,
the imaging device generates a second image of the subject by imaging the subject under the second imaging condition, and
the image processing unit processes the first image and the second image.

4. The endoscope device according to claim 3,
wherein the imaging device generates a plurality of at least one of first images and second images,
when the imaging device generates the plurality of first images, the image processing unit calculates a value indicating whether or not the plurality of first images are suitable for image processing, and
when the imaging device generates the plurality of second images, the image processing unit calculates a value indicating whether or not the plurality of second images are suitable for image processing.

5. The endoscope device according to claim 3,
wherein the imaging device generates a plurality of first images by imaging the subject under the first imaging condition,
the imaging device generates a plurality of second images by imaging the subject under the second imaging condition,
the image processing unit generates a third image by executing a noise reduction process on the plurality of first images,
the image processing unit generates a fourth image by executing the noise reduction process on the plurality of second images, and
the image processing unit executes a process different from the noise reduction process on the third image and the fourth image.

6. The endoscope device according to claim 3, wherein the image processing unit calculates three-dimensional (3D) coordinates of at least one point on a surface of the subject on the basis of the first image and the second image.

7. The endoscope device according to claim 5, wherein the image processing unit calculates 3D coordinates of at least one point on a surface of the subject on the basis of the third image and the fourth image.

8. The endoscope device according to claim 6, further comprising a data generation unit,
wherein the illumination light is white light,
the imaging device includes a red color filter, a green color filter, and a blue color filter,
the imaging device generates a color image as the image of the subject,
the color image has information indicating each of brightness of red, brightness of green, and brightness of blue, and
the data generation unit generates data in which 3D coordinates of a plurality of points on the surface of the subject are associated with the information corresponding to the plurality of points.

9. The endoscope device according to claim 6,
wherein the observation optical system includes a first optical system and a second optical system,
the first optical system and the second optical system are disposed on an optical front side of the imaging device,
the first optical system forms a first optical image of the subject corresponding to a first viewpoint on the imaging device,
the second optical system forms a second optical image of the subject corresponding to a second viewpoint different from the first viewpoint on the imaging device,
the switching unit causes light that passes through the first optical system to be incident on the imaging device and blocks light that passes through the second optical system under the first imaging condition,
the switching unit causes light that passes through the second optical system to be incident on the imaging device and blocks light that passes through the first optical system under the second imaging condition,
the control unit switches the optical image to be formed on the imaging device between the first optical image and the second optical image by controlling the switching unit, and
the image processing unit calculates the 3D coordinates using a passive stereo method on the basis of the first image corresponding to the first optical image and the second image corresponding to the second optical image.

10. The endoscope device according to claim 1, further comprising:
an image processing unit configured to execute image processing on a plurality of images during each frame period of the plurality of frame periods;
a data generation unit;
a first light source serving as the light source; and
a second light source serving as the light source,
wherein the illumination light includes first illumination light and second illumination light,
the first light source generates white light serving as the first illumination light,
the second light source generates the second illumination light,
the illumination optical system includes a pattern generation unit configured to give a spatial pattern including a bright part and a dark part to the second illumination light,
the illumination optical system radiates the second illumination light to which the pattern is given to the subject,
the plurality of imaging conditions include a first imaging condition and a second imaging condition,
under the first imaging condition, the first illumination light is radiated to the subject and radiation of the second illumination light to the subject is stopped,
under the second imaging condition, the second illumination light is radiated to the subject and radiation of the first illumination light to the subject is stopped,
the imaging device generates a first image of the subject by imaging the subject under the first imaging condition,
the imaging device generates a second image of the subject by imaging the subject under the second imaging condition,
the image processing unit calculates 3D coordinates of a plurality of points on a surface of the subject using an active stereo method on the basis of the second image,
the imaging device includes a red color filter, a green color filter, and a blue color filter,
the imaging device generates a color image as the first image,
the color image has information indicating each of brightness of red, brightness of green, and brightness of blue, and
the data generation unit generates data in which the 3D coordinates of the plurality of points are associated with the information corresponding to the plurality of points.

11. The endoscope device according to claim 10,
wherein the imaging device generates a plurality of at least one of first images and second images,
when the imaging device generates the plurality of first images, the image processing unit calculates a value indicating whether or not the plurality of first images are suitable for image processing, and
when the imaging device generates the plurality of second images, the image processing unit calculates a value indicating whether or not the plurality of second images are suitable for image processing.

12. The endoscope device according to claim 10,
wherein the imaging device generates a plurality of second images by imaging the subject under the second imaging condition,
the image processing unit generates a third image by executing a noise reduction process on the plurality of second images, and
the image processing unit calculates the 3D coordinates of the plurality of points on the basis of the third image.

13. The endoscope device according to claim 3,
wherein the illumination optical system includes a pattern generation unit configured to give a spatial pattern including a bright part and a dark part to the illumination light,
the plurality of imaging conditions further include a third imaging condition,
the imaging device generates a third image of the subject by imaging the subject under the third imaging condition,
the switching unit performs switching between the first imaging condition, the second imaging condition, and the third imaging condition by causing a phase of the pattern of the illumination light to be shifted,
a pattern phase under the first imaging condition, a pattern phase under the second imaging condition, and a pattern phase under the third imaging condition are different from one another, and
the image processing unit calculates 3D coordinates of a plurality of points on a surface of the subject using a phase shift method on the basis of at least the first image, the second image, and the third image.

14. The endoscope device according to claim 13, further comprising:
a data generation unit;
a first light source serving as the light source; and
a second light source serving as the light source,
wherein the illumination light includes first illumination light and second illumination light,
the first light source generates white light serving as the first illumination light,
the second light source generates the second illumination light,
the pattern generation unit gives the pattern to the second illumination light, the plurality of imaging conditions further include a fourth imaging condition, under the first imaging condition, the second imaging condition, and the third imaging condition, the second illumination light is radiated to the subject and radiation of the first illumination light to the subject is stopped, under the fourth imaging condition, the first illumination light is radiated to the subject and radiation of the second illumination light to the subject is stopped, the imaging device generates a fourth image of the subject by imaging the subject under the fourth imaging condition, the imaging device includes a red color filter, a green color filter, and a blue color filter, the imaging device generates a color image as the fourth image, the color image has information indicating each of brightness of red, brightness of green, and brightness of blue, and the data generation unit generates data in which the 3D coordinates of the plurality of points on the surface of the subject are associated with the information corresponding to the plurality of points.

15. The endoscope device according to claim 14, wherein the imaging device generates a plurality of at least one of first images, second images, third images, and fourth images, when the imaging device generates the plurality of first images, the image processing unit calculates a value indicating whether or not the plurality of first images are suitable for image processing, when the imaging device generates the plurality of second images, the image processing unit calculates a value indicating whether or not the plurality of second images are suitable for image processing, when the imaging device generates the plurality of third images, the image processing unit calculates a value indicating whether or not the plurality of third images are suitable for image processing, and when the imaging device generates the plurality of fourth images, the image processing unit calculates a value indicating whether or not the plurality of fourth images are suitable for image processing.

16. The endoscope device according to claim 13, wherein the control unit causes the switching unit to set the first imaging condition during a plurality of first frame periods, the control unit causes the switching unit to set the second imaging condition during a plurality of second frame periods and each second frame period of the plurality of second frame periods is different from each first frame period of the plurality of first frame periods, the control unit causes the switching unit to set the third imaging condition during a plurality of third frame periods and each third frame period of the plurality of third frame periods is different from each first frame period of the plurality of first frame periods and is different from each of second frame period of the plurality of second frame periods, the image processing unit generates a fifth image by executing a noise reduction process on a plurality of first images, the image processing unit generates a sixth image by executing the noise reduction process on a plurality of second images, the image processing unit generates a seventh image by executing the noise reduction process on a plurality of third images, and the image processing unit calculates the 3D coordinates of the plurality of points on the basis of the fifth image, the sixth image, and the seventh image.

17. The endoscope device according to claim 3, wherein a focus of the observation optical system under the first imaging condition is different from a focus of the observation optical system under the second imaging condition, and the image processing unit generates a third image by synthesizing the first image and the second image.

18. The endoscope device according to claim 3, wherein the amount of light of the light source under the first imaging condition is different from the amount of light of the light source under the second imaging condition, and the image processing unit generates a third image by synthesizing the first image and the second image.

19. The endoscope device according to claim 3, wherein the observation optical system includes a first optical system disposed on an optical front side of the imaging device and configured to form a first optical image of the subject on the imaging device, a second optical system disposed on an optical front side of the imaging device and configured to form a second optical image of the subject on the imaging device, and the switching unit configured to select either one of the first optical system and the second optical system and cause only either one of the first optical image and the second optical image to be formed on the imaging device, a visual field of the first optical system and a visual field of the second optical system have a common region, the switching control unit switches the optical image formed on the imaging device by controlling the switching unit, the first optical image is formed on the imaging device under the first imaging condition, the second optical image is formed on the imaging device under the second imaging condition, and the image processing unit aligns a region of the first image corresponding to the common region and a region of the second image corresponding to the common region and generates a third image by synthesizing the first image and the second image.

20. The endoscope device according to claim 3, wherein a focus of the observation optical system under the first imaging condition is different from a focus of the observation optical system under the second imaging condition, the control unit causes the switching unit to set the first imaging condition during a plurality of first frame periods, the control unit causes the switching unit to set the second imaging condition during a plurality of second frame periods and each second frame period of the plurality of second frame periods is different from each first frame period of the plurality of first frame periods, the image processing unit generates a fourth image by executing a noise reduction process on a plurality of first images, the image processing unit generates a fifth image by executing the noise reduction process on a plurality of second images, and the image processing unit generates the third image by synthesizing the fourth image and the fifth image.

* * * * *